US012735425B2

(12) United States Patent
Han et al.

(10) Patent No.: US 12,735,425 B2
(45) Date of Patent: Sep. 15, 2026

(54) 6,7-DIHYDRO-PYRANO[2,3-D]PYRIMIDINE INHIBITORS OF KRAS G12C MUTANT

(71) Applicant: Merck Sharp & Dohme LLC, Rahway, NJ (US)

(72) Inventors: Yongxin Han, Needham, MA (US); Elisabeth Hennessy, Weston, MA (US); Andrew J. Hoover, Framingham, MA (US); Jesus Moreno, Dorchester Center, MA (US); Uma Swaminathan, Auburndale, MA (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 620 days.

(21) Appl. No.: 18/038,367

(22) PCT Filed: Nov. 23, 2021

(86) PCT No.: PCT/US2021/060601

§ 371 (c)(1),
(2) Date: May 23, 2023

(87) PCT Pub. No.: WO2022/109485

PCT Pub. Date: May 27, 2022

(65) Prior Publication Data

US 2023/0416266 A1 Dec. 28, 2023

Related U.S. Application Data

(60) Provisional application No. 63/117,168, filed on Nov. 23, 2020.

(51) Int. Cl.
*C07D 491/052* (2006.01)
*A61P 35/00* (2006.01)

(52) U.S. Cl.
CPC .......... *C07D 491/052* (2013.01); *A61P 35/00* (2018.01)

(58) Field of Classification Search
CPC .................................................. C07D 491/052
See application file for complete search history.

(56) References Cited

U.S. PATENT DOCUMENTS 4,034,075 A 7/1977 Bays et al.
9,840,516 B2 12/2017 Li et al.
10,125,134 B2 11/2018 Blake et al.
10,144,724 B2 12/2018 Li et al.
10,556,906 B2 2/2020 Kuramoto et al.
11,090,304 B2 8/2021 Allen et al.
11,453,683 B1 9/2022 Wang et al.
11,459,327 B1 10/2022 Lv et al.
11,697,657 B2 7/2023 Bharathan et al.
2006/0135532 A1 6/2006 Bryant et al.
2010/0331305 A1 12/2010 Bergeron et al.
2014/0275070 A1 9/2014 Grembecka et al.
2014/0288045 A1 9/2014 Ren et al.

(Continued)

FOREIGN PATENT DOCUMENTS

CN 104011054 A 8/2014
CN 107556289 A 1/2018

(Continued)

OTHER PUBLICATIONS

Hamarsheh (Nat Commun 11, 5439 (2020)) (Year: 2020).*
D.S. Hong, et al., "KRASG12C Inhibition with Sotorasib in Advanced Solid Tumors", The New England Journal of Medicine, vol. 383 No. 13 pp. 1207-1217 (2020).
D. Gentile, et al., "Ras Binder Induces a Modified Switch-II Pocket in GTP and GDP States", Cell Chemical Biology, 24, pp. 1455-1466 (2017).
D. Kessler, et al., "Drugging an undruggable pocket on KRAS", Proceedings of the National Academy of Sciences (PNAS), vol. 116, No. 32, pp. 15823-15829 (2019).
Y. Mao, et al., "Design, synthesis and biological evaluation of novel pyrimidine, 3-cyanopyridine and m-amino-N-phenylbenzamide based monocyclic EGFR tyrosine kinase inhibitors", Bioorganic & Medicinal Chemistry, 21, pp. 3090-3104 (2013).

(Continued)

*Primary Examiner* — Kortney L. Klinkel
*Assistant Examiner* — Richard Grant Peckham
(74) *Attorney, Agent, or Firm* — Venable LLP

(57) ABSTRACT

The disclosure provides compounds of Formula (I)

(I)

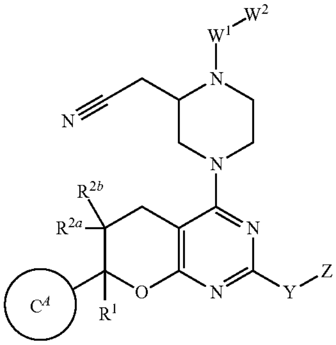

or a pharmaceutically acceptable salt thereof, wherein $W^1$, $W^2$, Y, Z, $C^A$, $R^1$, $R^{2a}$, and $R^{2b}$ are as described herein. The compounds or their pharmaceutically acceptable salts can inhibit the G12C mutant of Kirsten rat sarcoma (KRAS) protein and are expected to have utility as therapeutic agents, for example, for treating cancer. The disclosure also provides pharmaceutical compositions which comprise compounds of Formula (I) or pharmaceutically acceptable salts thereof. The disclosure also relates to methods for use of the compounds or their pharmaceutically acceptable salts in the therapy and prophylaxis of cancer and for preparing pharmaceuticals for this purpose.

18 Claims, No Drawings

Specification includes a Sequence Listing.

(56) References Cited

U.S. PATENT DOCUMENTS

| | | | |
|---|---|---|---|
| 2014/0371203 | A1 | 12/2014 | Madge et al. |
| 2015/0176010 | A1 | 6/2015 | Wersinger |
| 2015/0239900 | A1 | 8/2015 | Li et al. |
| 2015/0246934 | A1 | 9/2015 | Bensen et al. |
| 2016/0046647 | A1 | 2/2016 | Grembecka et al. |
| 2016/0108019 | A1 | 4/2016 | Li et al. |
| 2016/0137665 | A1 | 5/2016 | Grembecka et al. |
| 2016/0152634 | A1 | 6/2016 | Madge et al. |
| 2016/0159738 | A1 | 6/2016 | Ren et al. |
| 2016/0297774 | A1 | 10/2016 | Li et al. |
| 2016/0318866 | A1 | 11/2016 | Becker-Pelster et al. |
| 2017/0131278 | A1 | 5/2017 | Patricelli et al. |
| 2017/0197945 | A1 | 7/2017 | Li et al. |
| 2017/0253611 | A1 | 9/2017 | Grembecka et al. |
| 2018/0072723 | A1 | 3/2018 | Blake et al. |
| 2018/0118757 | A1 | 5/2018 | Li et al. |
| 2018/0127396 | A1 | 5/2018 | Li et al. |
| 2018/0141927 | A1 | 5/2018 | Li et al. |
| 2018/0162812 | A1 | 6/2018 | Ren et al. |
| 2018/0177767 | A1 | 6/2018 | Lanman et al. |
| 2018/0334454 | A1 | 11/2018 | Lanman et al. |
| 2019/0062313 | A1 | 2/2019 | Li et al. |
| 2019/0062330 | A1 | 2/2019 | Blake et al. |
| 2019/0127336 | A1 | 5/2019 | Li et al. |
| 2019/0144444 | A1 | 5/2019 | Blake et al. |
| 2019/0248767 | A1 | 8/2019 | Planken et al. |
| 2019/0270743 | A1 | 9/2019 | Marx et al. |
| 2019/0276432 | A1 | 9/2019 | Beaumont et al. |
| 2019/0284144 | A1 | 9/2019 | Li et al. |
| 2019/0292182 | A1 | 9/2019 | Kuramoto et al. |
| 2019/0343838 | A1 | 11/2019 | Allen et al. |
| 2019/0374542 | A1 | 12/2019 | Allen et al. |
| 2020/0055845 | A1 | 2/2020 | Lanman et al. |
| 2020/0069657 | A1 | 3/2020 | Lanman et al. |
| 2020/0115363 | A1 | 4/2020 | Li et al. |
| 2020/0115375 | A1 | 4/2020 | Barda et al. |
| 2020/0140437 | A1 | 5/2020 | Kuramoto et al. |
| 2020/0165231 | A1 | 5/2020 | Shin et al. |
| 2020/0181118 | A1 | 6/2020 | Malhotra et al. |
| 2020/0237771 | A1 | 7/2020 | Hallur et al. |
| 2020/0262837 | A1 | 8/2020 | Marx et al. |
| 2020/0289503 | A1 | 9/2020 | Huang |
| 2020/0331911 | A1 | 10/2020 | Marx et al. |
| 2021/0009577 | A1 | 1/2021 | Lanman et al. |
| 2021/0024501 | A1 | 1/2021 | Li et al. |
| 2021/0040089 | A1 | 2/2021 | Gao et al. |
| 2021/0047297 | A1 | 2/2021 | Schulze et al. |
| 2021/0122764 | A1 | 4/2021 | Bharathan et al. |
| 2021/0395234 | A1 | 12/2021 | Sakamoto et al. |
| 2022/0064141 | A1 | 3/2022 | Fang et al. |
| 2022/0298174 | A1 | 9/2022 | Guo et al. |
| 2022/0315597 | A1 | 10/2022 | Su et al. |
| 2022/0315598 | A1 | 10/2022 | Xu et al. |
| 2022/0370416 | A1 | 11/2022 | Chu et al. |
| 2022/0389029 | A1 | 12/2022 | Guo et al. |
| 2022/0402916 | A1 | 12/2022 | Hoover et al. |
| 2023/0023023 | A1 | 1/2023 | Shibata et al. |
| 2023/0049402 | A1 | 2/2023 | Sakamoto et al. |
| 2023/0174518 | A1 | 6/2023 | Kawai |
| 2023/0181536 | A1 | 6/2023 | Abe et al. |
| 2023/0348495 | A1 | 11/2023 | Kawai et al. |
| 2024/0043448 | A1 | 2/2024 | Bharathan et al. |
| 2024/0083913 | A1 | 3/2024 | Bharathan et al. |
| 2024/0124478 | A1 | 4/2024 | Han et al. |
| 2024/0239788 | A1 | 7/2024 | Sloman et al. |
| 2024/0246968 | A1 | 7/2024 | Shibata et al. |
| 2024/0262842 | A1 | 8/2024 | Shibata et al. |
| 2024/0317759 | A1 | 9/2024 | Kobayakawa et al. |

FOREIGN PATENT DOCUMENTS

| | | | |
|---|---|---|---|
| CN | 109843856 | A | 6/2019 |
| CN | 112430234 | A | 3/2021 |
| CN | 114615981 | A | 6/2022 |
| EP | 3871673 | A1 | 9/2021 |
| EP | 4053120 | A1 | 9/2022 |
| JP | 2016-519072 | A | 6/2016 |
| JP | 2016-532656 | A | 10/2016 |
| JP | 2017-528498 | A | 9/2017 |
| WO | 03/037898 | A1 | 5/2003 |
| WO | 2005/019177 | A1 | 3/2005 |
| WO | 2009/114575 | A1 | 9/2009 |
| WO | 2010/064705 | A1 | 6/2010 |
| WO | 2013/072694 | A1 | 5/2013 |
| WO | 2014/043272 | A1 | 3/2014 |
| WO | 2014/143659 | A1 | 9/2014 |
| WO | 2014/152588 | A1 | 9/2014 |
| WO | 2014/164543 | A1 | 10/2014 |
| WO | 2015/054572 | A1 | 4/2015 |
| WO | 2015/091415 | A1 | 6/2015 |
| WO | 2015/131005 | A1 | 9/2015 |
| WO | 2016/029454 | A1 | 3/2016 |
| WO | 2016/044772 | A1 | 3/2016 |
| WO | 2016/049524 | A1 | 3/2016 |
| WO | 2016/049565 | A1 | 3/2016 |
| WO | 2016/049568 | A1 | 3/2016 |
| WO | 2016/164675 | A1 | 10/2016 |
| WO | 2016/168540 | A1 | 10/2016 |
| WO | 2017/015562 | A1 | 1/2017 |
| WO | 2017/058728 | A1 | 4/2017 |
| WO | 2017/058768 | A1 | 4/2017 |
| WO | 2017/058792 | A1 | 4/2017 |
| WO | 2017/058805 | A1 | 4/2017 |
| WO | 2017/058807 | A1 | 4/2017 |
| WO | 2017/058902 | A1 | 4/2017 |
| WO | 2017/058915 | A1 | 4/2017 |
| WO | 2017/070256 | A2 | 4/2017 |
| WO | 2017/087528 | A1 | 5/2017 |
| WO | 2017/100546 | A1 | 6/2017 |
| WO | 2017/172979 | A1 | 10/2017 |
| WO | 2017/201161 | A1 | 11/2017 |
| WO | 2018/022897 | A1 | 2/2018 |
| WO | 2018/064510 | A1 | 4/2018 |
| WO | 2018/068017 | A1 | 4/2018 |
| WO | 2018/119183 | A2 | 6/2018 |
| WO | 2018/140512 | A1 | 8/2018 |
| WO | 2018/140513 | A1 | 8/2018 |
| WO | 2018/140514 | A1 | 8/2018 |
| WO | 2018/140598 | A1 | 8/2018 |
| WO | 2018/140599 | A1 | 8/2018 |
| WO | 2018/140600 | A1 | 8/2018 |
| WO | 2018/143315 | A1 | 8/2018 |
| WO | 2018/206539 | A1 | 11/2018 |
| WO | 2018/217651 | A1 | 11/2018 |
| WO | 2018/218069 | A1 | 11/2018 |
| WO | 2018/218070 | A2 | 11/2018 |
| WO | 2018/218071 | A1 | 11/2018 |
| WO | 2019/051291 | A1 | 3/2019 |
| WO | 2019/058132 | A1 | 3/2019 |
| WO | 2019/058393 | A1 | 3/2019 |
| WO | 2019/077631 | A1 | 4/2019 |
| WO | 2019/099524 | A1 | 5/2019 |
| WO | 2019/099703 | A1 | 5/2019 |
| WO | 2019/110751 | A1 | 6/2019 |
| WO | 2019/155399 | A1 | 8/2019 |
| WO | 2019/167000 | A1 | 9/2019 |
| WO | 2019/185525 | A1 | 10/2019 |
| WO | 2019/215203 | A1 | 11/2019 |
| WO | 2020/035031 | A1 | 2/2020 |
| WO | 2020/041331 | A1 | 2/2020 |
| WO | 2020/050890 | A2 | 3/2020 |
| WO | 2020/085493 | A1 | 4/2020 |
| WO | 2020/097537 | A2 | 5/2020 |
| WO | 2020/101736 | A1 | 5/2020 |
| WO | 2020/113071 | A1 | 6/2020 |
| WO | 2020/146613 | A1 | 7/2020 |
| WO | 2020/156285 | A1 | 8/2020 |
| WO | 2020/177629 | A1 | 9/2020 |
| WO | 2020/178282 | A1 | 9/2020 |
| WO | 2020/221239 | A1 | 11/2020 |
| WO | 2020/233592 | A1 | 11/2020 |
| WO | 2020/234103 | A1 | 11/2020 |
| WO | 2020/236940 | A1 | 11/2020 |
| WO | 2020/238791 | A1 | 12/2020 |

(56) References Cited

FOREIGN PATENT DOCUMENTS

| | | | |
|---|---|---|---|
| WO | 2020/239077 | A1 | 12/2020 |
| WO | 2020/239123 | A1 | 12/2020 |
| WO | 2020/244637 | A1 | 12/2020 |
| WO | 2020/259432 | A1 | 12/2020 |
| WO | 2020/259513 | A1 | 12/2020 |
| WO | 2020/259573 | A1 | 12/2020 |
| WO | 2021/000885 | A1 | 1/2021 |
| WO | 2021/023154 | A1 | 2/2021 |
| WO | 2021/027911 | A1 | 2/2021 |
| WO | 2021/027943 | A1 | 2/2021 |
| WO | 2021/031952 | A1 | 2/2021 |
| WO | 2021/037018 | A1 | 3/2021 |
| WO | 2021/041671 | A1 | 3/2021 |
| WO | 2021/043322 | A1 | 3/2021 |
| WO | 2021/052499 | A1 | 3/2021 |
| WO | 2021/055728 | A1 | 3/2021 |
| WO | 2021/057832 | A1 | 4/2021 |
| WO | 2021/058018 | A1 | 4/2021 |
| WO | 2021/063346 | A1 | 4/2021 |
| WO | 2021/078312 | A1 | 4/2021 |
| WO | 2021/081212 | A1 | 4/2021 |
| WO | 2021/083167 | A1 | 5/2021 |
| WO | 2021/084765 | A1 | 5/2021 |
| WO | 2021/085653 | A1 | 5/2021 |
| WO | 2021/086833 | A1 | 5/2021 |
| WO | 2021/088458 | A1 | 5/2021 |
| WO | 2021/093758 | A1 | 5/2021 |
| WO | 2021/098859 | A1 | 5/2021 |
| WO | 2021/104431 | A1 | 6/2021 |
| WO | 2021/106230 | A1 | 6/2021 |
| WO | 2021/106231 | A1 | 6/2021 |
| WO | 2021/107160 | A1 | 6/2021 |
| WO | 2021/109737 | A1 | 6/2021 |
| WO | 2021/113595 | A1 | 6/2021 |
| WO | 2021/118877 | A1 | 6/2021 |
| WO | 2021/121330 | A1 | 6/2021 |
| WO | 2021/121367 | A1 | 6/2021 |
| WO | 2021/121371 | A1 | 6/2021 |
| WO | 2021/124222 | A1 | 6/2021 |
| WO | 2021/127404 | A1 | 6/2021 |
| WO | 2021/129824 | A1 | 7/2021 |
| WO | 2021/147965 | A1 | 7/2021 |
| WO | 2021/147967 | A1 | 7/2021 |
| WO | 2021/215544 | A1 | 10/2021 |
| WO | 2021/215545 | A1 | 10/2021 |
| WO | 2021/219072 | A1 | 11/2021 |
| WO | 2022/066646 | A1 | 3/2022 |
| WO | 2022/105857 | A1 | 5/2022 |
| WO | 2022/109487 | A1 | 5/2022 |
| WO | 2022/132200 | A1 | 6/2022 |
| WO | 2022/133038 | A1 | 6/2022 |
| WO | 2022/173870 | A1 | 8/2022 |
| WO | 2022/177917 | A2 | 8/2022 |
| WO | 2022/221739 | A1 | 10/2022 |
| WO | 2022/232318 | A1 | 11/2022 |
| WO | 2022/232320 | A1 | 11/2022 |
| WO | 2022/250170 | A1 | 12/2022 |
| WO | 2022/251576 | A1 | 12/2022 |
| WO | 2022/256459 | A1 | 12/2022 |
| WO | 2023/046135 | A1 | 3/2023 |
| WO | 2023/097227 | A1 | 6/2023 |
| WO | 2023/103523 | A1 | 6/2023 |
| WO | 2024/009191 | A1 | 1/2024 |
| WO | 2024/015262 | A1 | 1/2024 |
| WO | 2024/032704 | A1 | 2/2024 |
| WO | 2024/041573 | A1 | 2/2024 |
| WO | 2024/044667 | A2 | 2/2024 |
| WO | 2024/063578 | A1 | 3/2024 |
| WO | 2024/083168 | A1 | 4/2024 |
| WO | 2024/103010 | A1 | 5/2024 |
| WO | 2024/120433 | A1 | 6/2024 |
| WO | 2024/209339 | A1 | 10/2024 |
| WO | 2024/213979 | A1 | 10/2024 |
| WO | 2024/233776 | A1 | 11/2024 |
| WO | 2024/238343 | A1 | 11/2024 |

OTHER PUBLICATIONS

PubChem CID 10121096, PubChem release Jun. 18, 2019, modify date Nov. 21, 2020, retrieved on Feb. 10, 2021 (9 pages).

G. Palfy, et al., "1H, 15N backbone assignment and comparative analysis of the wild type and G12C, G12D, G12V mutants of K-Ras bound to GDP at physiological pH", Biomolecular NMR Assignment, vol. 14, No. 1, pp. 1-7 (2019).

M.R. Janes, et al., "Targeting KRAS Mutant Cancers with a Covalent G12C-Specific Inhibitor", Cell, 172, pp. 578-589 (2018).

M.P. Patricelli, et al., "Selective Inhibition of Oncogenic KRAS Output with Small Molecules Targeting the Inactive State", Cancer Discovery, 6(3), pp. 316-329 (2016).

H. Chuang, et al., "Pharmacological strategies to target oncogenic KRAS signaling in pancreatic cancer", Pharmacological Research, 117, pp. 370-376 (2017).

Lopez-Tapia, F., et al., "Linker Variation and Structure-Activity Relationship Analyses of Carboxylic Acid-based Small Molecule STAT3 Inhibitors", ACS Med. Chem. Lett. 2018, 9, 250-255.

R.B. Kargbo, "Small Molecule Inhibitors of KRAS G12C Mutant", Acs Med. Chem. Lett., vol. 12, pp. 1210-1211 (2021).

PubChem SID 469710826, available Jul. 28, 2022.

J.G. Kettle, et al., "Structure-Based Design and Pharmacokinetic Optimization of Covalent Allosteric Inhibitors of the Mutant GTPase KRAS G12C", J. Med. Chem., vol. 63, pp. 4468-4483 (2020).

Q. Zheng, et al., "Drugging the Next Undruggable KRAS Allele-Gly12Asp", J. Med. Chem, vol. 65, pp. 3119-3122 (2022).

Examination Report in co-pending European Patent Application No. 21895829.6 dated Sep. 17, 2024 (5 pages).

International Search Report and Written Opinion in corresponding international application No. PCT/US21/60601 dated Mar. 9, 2022 (11 pages).

* cited by examiner

6,7-DIHYDRO-PYRANO[2,3-D]PYRIMIDINE INHIBITORS OF KRAS G12C MUTANT

CROSS REFERENCE TO RELATED APPLICATIONS

This application is a national-stage entry under 35 U.S.C. § 371 of International Application No. PCT/US2021/060601 filed on Nov. 23, 2021, and claims the benefit of priority of U.S. Provisional Application No. 63/117,168, filed Nov. 23, 2020.

FIELD OF THE INVENTION

The present disclosure relates to certain 6,7-dihydro-5H-pyrano[2,3-d]pyrimidines and pharmaceutically acceptable salts thereof that inhibit the G12C mutant of Kirsten rat sarcoma (KRAS) protein and are expected to have utility as therapeutic agents, for example, for treatment of cancer. The present application also relates to pharmaceutical compositions containing such compounds as well as methods of using the compounds for treating cancer.

BACKGROUND OF THE INVENTION

RAS proteins are membrane-associated guanine nucleotide-binding proteins which function as molecular switches. RAS proteins function as components of signaling pathways transmitting signals from cell-surface receptors to regulate cellular proliferation, survival and differentiation. RAS proteins cycle between an inactive GDP-bound state and an active GTP-bound state.

The most notable members of the RAS subfamily are HRAS, KRAS and NRAS, mainly being implicated in many types of cancer. However, there are many other members including DIRAS1; DIRAS2; DIRAS3; ERAS; GEM; MRAS; KIRAS1; KIRAS2; NRAS; RALA; RALB; RAPIA; RAPIB; RAP2A; RAP2B; RAP2C; RASD1; RASD2; RASL10A; RASL10B; RASL11A; RASL11B; RASL12; REM1; REM2; RERG; RERGL; RRAD; RRAS and RRAS2.

Mutations in any one of the three main isoforms of RAS (HRAS, NRAS, or KRAS) genes are among the most common events in human tumorigenesis. KRAS mutations are detected in 25-30% of tumors. By comparison, the rates of oncogenic mutation occurring in the NRAS and HRAS family members are much lower (8% and 3% respectively).

Exchange of a glycine for a cysteine at residue 12 of RAS (the G12C mutation) results from a mutation commonly found in RAS genes. Large-scale cancer sequencing studies indicate that the G12C mutation appeared most frequently in lung, colorectal and pancreatic cancers. Histological analysis of seven cancer types indicated non-small cell lung cancer contributed the most, 70-75%, to cancer cases having the KRAS G12C mutation. See Lindsay, C. R., et al., *Br J Cancer* 121, 197-198 (2019).

Accordingly, while progress has been made in this field, there remains a need in the art for improved compounds and methods for treatment of cancer, for example, by inhibition of a mutant KRAS, HRAS or NRAS protein (e.g., KRAS G12C). Embodiments of the present disclosure fulfill this need and provide further related advantages.

SUMMARY OF THE DISCLOSURE

The present disclosure provides 6,7-dihydro-5H-pyrano[2,3-d]pyrimidines which modulate mutant KRAS, HRAS, and/or NRAS proteins and may be valuable pharmaceutically active compounds for the treatment of cancer. In some embodiments the disclosed compounds selectively inhibit the KRAS (G12C) protein. The compounds of Formula (I)

(I)

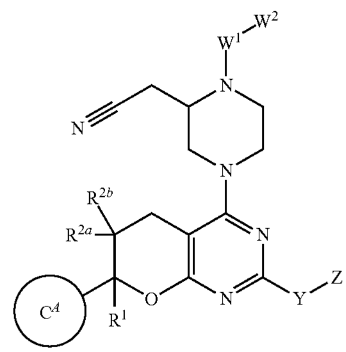

and their pharmaceutically acceptable salts, can modulate the activity of KRAS, HRAS and/or NRAS activity and thereby affect the signaling pathway which regulates cell growth, differentiation, and proliferation associated with oncological disorders. In certain embodiments, the compounds of Formula (I) can inhibit the KRAS (G12C) protein. The disclosure furthermore provides processes for preparing compounds of Formula (I), methods for using such compounds to treat oncological disorders, and pharmaceutical compositions which comprise compounds of Formula (I).

DETAILED DESCRIPTION OF THE INVENTION

Compounds of the Disclosure

In embodiment no. 1, the present disclosure provides a compound having structural Formula (I) as shown above wherein:

ring $C^A$ is
- (i) naphthyl;
- (ii) phenyl;
- (iii) a bicyclic 9- or 10-membered heteroaryl containing 1 to 3 ring atoms selected from N, O, or S; or
- (iv) a tricyclic 13- or 14-membered heteroaryl containing 1 to 3 ring atoms selected from N, O, or S;
  wherein ring $C^A$ is unsubstituted or substituted by 1 to 4 $R^{CA}$ substituents which are halo, $C_1$-$C_3$ alkyl, $C_1$-$C_3$ fluoroalkyl, $C_1$-$C_3$ alkoxy, hydroxy or cyano;

$R^1$ is H or $C_1$-$C_3$ alkyl;

$R^{2a}$ and $R^{2b}$ are independently H, F, $C_1$-$C_3$ alkyl, or $C_1$-$C_3$ fluoroalkyl;

$W^1$ is —C(O)— or —$S(O)_2$—;

$W^2$ is a group of the formula:

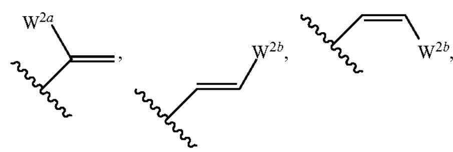

-continued

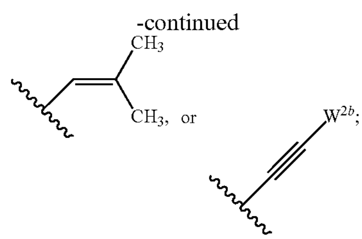

wherein $W^{2a}$ is H, $CH_3$, F, cyano, $CH_2OH$, $CH_2CH_2OH$, or $CH_2Br$;

$W^{2b}$ is $CH_3$, $CH_2NH_2$, $CH_2N(H)CH_3$, $CH_2N(CH_3)_2$, $CH_2$—NH-cyclopropyl,

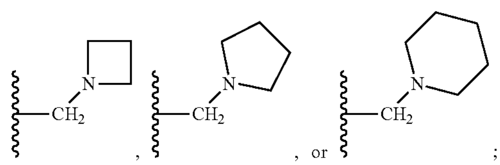

, , or ;

Y is —$O(C(R^y)_2)_m$— or —C(O)—N(H)—$(C(R^y)_2)_m$—;

each $R^y$ is independently H or $C_1$-$C_3$ alkyl, or alternatively two $R^y$ together with the carbon atom to which they are attached form a cyclopropyl, cyclobutyl, cyclopentyl or cyclohexyl ring;

the subscript m is 1, 2, or 3;

Z is (a)

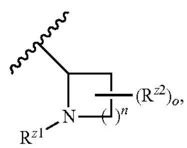

wherein $R^{z1}$ is $C_1$-$C_3$ alkyl;

each $R^{z2}$ is independently fluoro or $C_1$-$C_3$ alkyl;

the subscript n is 1, 2, or 3;

the subscript o is 0, 1, or 2; or (b) —$N(R^{z3})_2$, wherein each $R^{z3}$ is independently H or $C_1$-$C_3$ alkyl; or alternatively, two $R^{z3}$, together with the nitrogen atom to which they are attached, form an aziridinyl, azetidinyl, pyrrolidinyl, piperidinyl, or azepinyl ring, or a pharmaceutically acceptable salt thereof.

In embodiment no. 2, the present disclosure provides a compound of Formula (I) wherein the group

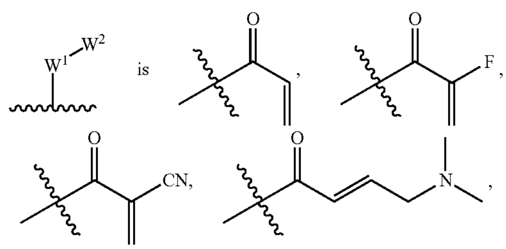

-continued

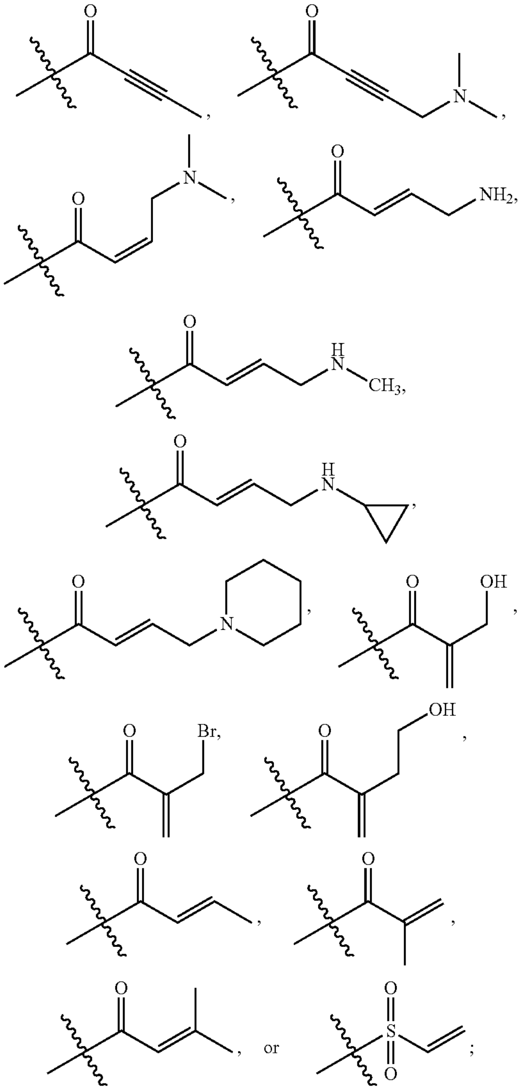

and the remaining variables are as set forth in embodiment no. 1.

In embodiment no. 3, the group —$W^1$—$W^2$ is —C(O)—C(H)═$CH_2$, and the remaining variables are as set forth in embodiment no. 1.

In embodiment no. 4, the present disclosure provides a compound of Formula (I) wherein ring $C^A$ is unsubstituted or substituted naphthyl, phenyl, indazolyl, or benzo[e]indazolyl, and the remaining variables are as set forth in embodiment no. 1.

In embodiment no. 5, ring $C^A$ is:

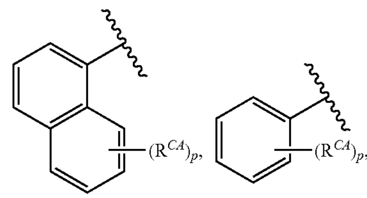

-continued

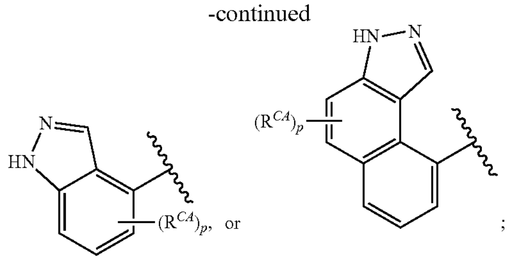

and the subscript p is 0, 1, or 2. In instances wherein ring $C^A$ is a bi- or tri-cyclic ring system, $R^{CA}$ can be substituted on any ring of the multicylic ring system.

In embodiment no. 6, the present disclosure provides a compound of Formula (I), wherein Y is $—OC(R^y)_2—$, and $R^y$ and the remaining variables are as set forth in embodiment no. 1.

In embodiment no. 7, Z is

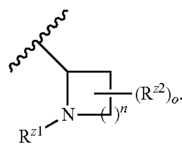

and $R^{z1}$, $R^{z2}$, and the subscripts n and o are as set forth in embodiment no. 1. In embodiment no. 8, the subscript n is 2.

In embodiment no. 9, the present disclosure provides a compound of Formula (I), wherein Y is —C(O)—N(H)—, and the remaining variables are as set forth in embodiment no. 1.

In embodiment no. 10, Y is as set forth in embodiment no. 9 and Z is $—N(R^{z3})_2$, and $R^{z3}$ is as set forth in embodiment no. 1.

In embodiment no. 11, the present disclosure provides a compound of Formula (I), wherein —Y—Z is

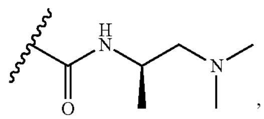 [SMILES: *C(=O)N[C@H](C)CN(C)C]

and the remaining variables are as set forth in embodiment no. 1.

In embodiment no. 12, the present disclosure provides a compound of Formula (I), wherein $R^1$ is H or methyl; and the remaining variables are as set forth in embodiment no. 1. In embodiment no. 13, $R^1$ is H.

In embodiment no. 14, the present disclosure provides a compound of Formula (I), wherein $R^{2a}$ and $R^{2b}$ are independently H, F, or methyl; and the remaining variables are as set forth in embodiment no. 1. In embodiment no. 15, $R^{2a}$ and $R^{2b}$ are H.

In embodiment no. 16, the present disclosure provides a compound of Formula (I), wherein the group $—W^1—W^2$ is $—C(O)—C(H)═CH_2$;

$R^1$ is H or methyl;

$R^{2a}$ and $R^{2b}$ are independently H, F, or methyl; and ring $C^A$ is as set forth in embodiment no. 5.

In embodiment no. 17, —Y—Z is:

(i)

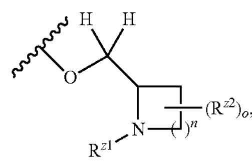

wherein $R^{z1}$, $R^{z2}$, and the subscripts n and o are as set forth in embodiment no. 1; or (ii)

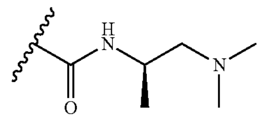

and the remaining variables are as set forth in embodiment no. 16.

In embodiment no. 18, the present disclosure provides a compound as described in any one of Examples 1-12 as set forth below, or a pharmaceutically acceptable salt thereof.

The present disclosure includes the pharmaceutically acceptable salts of the compounds defined herein, including the pharmaceutically acceptable salts of all structural formulas, embodiments and classes defined herein.

Definitions

Unless defined otherwise, all technical and scientific terms used herein have the same meaning as is commonly understood by one of skill in the art to which this invention belongs.

As used throughout this disclosure, "a compound of Formula (I)" is to be understood to include "a compound of Formula (I) or a pharmaceutically acceptable salt thereof".

"Alkyl", as well as other groups having the prefix "alk", such as alkoxy, and the like, means carbon chains which may be linear or branched, or combinations thereof, containing the indicated number of carbon atoms. In particular embodiments, linear alkyl groups have 1-6 carbon atoms and branched alkyl groups have 3-7 carbon atoms. Examples of alkyl groups include methyl, ethyl, propyl, isopropyl, butyl, sec- and tert-butyl, pentyl, hexyl, heptyl, octyl, nonyl and the like.

"Alkoxy" and "alkyl-O—" are used interchangeably and refer to an alkyl group linked to oxygen.

"Bicyclo-ring system" or "bicyclic ring system" refers to two joined rings. The rings may be fused, i.e., share two adjacent atoms, or "spirocyclic", i.e., share only a single atom.

"Cycloalkyl" means a saturated cyclic hydrocarbon radical. In particular embodiments, the cycloalkyl group has 3-12 carbon atoms, forming 1-3 carbocyclic rings that are fused. Examples of cycloalkyl include cyclopropyl, cyclobutyl, cyclopentyl, cyclohexyl, cycloheptyl, adamantyl, and the like.

"Fluoroalkyl" include mono-substituted as well as multiple fluoro-substituted alkyl groups, up to perfluoro substituted alkyl. For example, fluoromethyl, 1,1-difluoroethyl, trifluoromethyl or 1,1,1,2,2-pentafluorobutyl are included.

"Heteroaryl" refers to aromatic monocyclic, bicyclic and tricyclic ring structures in which one or more atoms in the ring, the heteroatom(s), is an element other than carbon.

Heteroatoms are typically O, S, or N atoms. Examples of heteroaromatic groups include pyridinyl, pyrimidinyl, pyrrolyl, pyridazinyl, isoxazolyl, thiazolyl, oxazolyl, indolyl, benzoxazolyl, benzothiazolyl, and imidazolyl.

"Halogen" or "halo" unless otherwise indicated, includes fluorine (fluoro), chlorine (chloro), bromine (bromo) and iodine (iodo). In one embodiment, halo is fluoro (—F) or chloro (—Cl).

"Tricyclo-ring system" or "tricyclic ring system" refers to three joined rings. The rings may be fused, i.e., share adjacent atoms, or "spirocyclic", i.e., share only a single atom.

When any variable (e.g., $R^y$) occurs more than one time in any constituent or in Formula (I) or other generic formulas herein, its definition on each occurrence is independent of its definition at every other occurrence. Combinations of substituents and/or variables are permissible only if such combinations result in stable compounds. In choosing compounds of the present disclosure, one of ordinary skill in the art will recognize that the various substituents, e.g., $R^y$, are to be chosen in conformity with well-known principles of chemical structure connectivity and stability. Unless expressly stated to the contrary, substitution by a named substituent is permitted on any atom in a ring (e.g., aryl, a heteroaryl ring, or a saturated heteroaryl ring) provided such ring substitution is chemically allowed and results in a stable compound. A "stable" compound is a compound which can be prepared and isolated and whose structure and properties remain or can be caused to remain essentially unchanged for a period of time sufficient to allow use of the compound for the purposes described herein (e.g., therapeutic or prophylactic administration to a subject).

The term "substituted" shall be deemed to include multiple degrees of substitution by a named substituent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

Unless expressly depicted or described otherwise, variables depicted in a structural formula with a "floating" bond, such as $R^{CA}$ in Formula (I), are permitted on any available carbon atom in the ring to which the variable is attached. When a moiety is noted as being "optionally substituted" in Formula (I) or any embodiment thereof, it means that Formula (I) or the embodiment thereof encompasses compounds that contain the noted substituent (or substituents) on the moiety and also compounds that do not contain the noted substituent (or substituents) on the moiety.

The wavy line 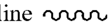, as used herein, indicates a point of attachment to the rest of the compound.

Compounds of Formula (I) may contain one or more asymmetric centers and can thus occur as racemates and racemic mixtures, single enantiomers, diastereoisomeric mixtures and individual diastereoisomers. Centers of asymmetry that are present in the compounds of Formula (I) can all independently of one another have S configuration or R configuration. The compounds of this disclosure include all possible enantiomers and diastereomers and mixtures of two or more stereoisomers, for example, mixtures of enantiomers and/or diastereomers, in all ratios. Thus, enantiomers are a subject of the disclosure in enantiomerically pure form, both as levorotatory and as dextrorotatory antipodes, in the form of racemates and in the form of mixtures of the two enantiomers in all ratios. In the case of a cis/trans isomerism, the disclosure includes both the cis form and the trans form as well as mixtures of these forms in all ratios. The present disclosure is meant to comprehend all such stereoisomeric forms of the compounds of Formula (I). Where a structural formula or chemical name specifies a particular configuration at a stereocenter, the enantiomer or stereoisomer of the compound resulting from that specified stereocenter is intended. Where a structural formula of the compounds of Formula (I) indicates a straight line at a chiral center, the structural formula includes both the S and R stereoisomers associated with the chiral center and mixtures thereof.

Compounds of Formula (I) may be separated into their individual diastereoisomers by, for example, fractional crystallization from a suitable solvent, for example, methanol or ethyl acetate or a mixture thereof, or via chiral chromatography using an optically active stationary phase. Absolute stereochemistry may be determined by X-ray crystallography of crystalline products or crystalline intermediates which are derivatized, if necessary, with a reagent containing an asymmetric center of known absolute configuration. Vibrational circular dichroism (VCD) may also be used to determine the absolute stereochemistry. Alternatively, any stereoisomer or isomers of a compound of Formula (I) may be obtained by stereospecific synthesis using optically pure starting materials or reagents of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereoisomeric mixture, followed by separation of the individual diastereoisomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

For compounds of Formula (I) described herein which contain olefinic double bonds, unless specified otherwise, they are meant to include both E and Z geometric isomers.

Some of the compounds described herein may exist as tautomers which have different points of attachment of hydrogen accompanied by one or more double bond shifts. For example, a ketone and its enol form are keto-enol tautomers. The individual tautomers as well as mixtures thereof are encompassed with compounds of Formula I of the present disclosure.

In the compounds of Formula (I), the atoms may exhibit their natural isotopic abundances, or one or more of the atoms may be artificially enriched in a particular isotope having the same atomic number, but an atomic mass or mass number different from the atomic mass or mass number predominantly found in nature. The present disclosure as described and claimed herein is meant to include all suitable isotopic variations of the compounds of Formula (I) and embodiments thereof. For example, different isotopic forms of hydrogen (H) include protium ($^1H$) and deuterium ($^2H$, also denoted herein as D). Protium is the predominant hydrogen isotope found in nature. Enriching for deuterium may afford certain therapeutic advantages, such as increasing in vivo half-life or reducing dosage requirements or may provide a compound useful as a standard for characterization of biological samples. Isotopically-enriched compounds of Formula (I), can be prepared without undue experimentation by conventional techniques well known to those skilled in the art or by processes analogous to those described in the Schemes and Examples herein using appropriate isotopically-enriched reagents and/or intermediates.

The term "pharmaceutically acceptable salts" refers to salts prepared from pharmaceutically acceptable non-toxic bases or acids. When the compound of the present disclosure is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Preferred are the ammonium, calcium, magnesium, potassium and sodium salts. Salts prepared from pharmaceutically acceptable organic non-toxic bases include salts of primary, secondary, and tertiary amines derived from both naturally occurring and synthetic sources. Pharmaceutically acceptable organic non-toxic bases from which salts can be formed include, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, dicyclohexylamine, lysine, methylglucamine, morpholine, piperazine, piperidine, polyamine resins, procaine, purines, theobromine, triethylamine, trimethylamine, tripropylamine, tromethamine and the like.

When the compound of the present disclosure is basic, its corresponding salt can be conveniently prepared from pharmaceutically acceptable non-toxic inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, hydrochloric, maleic, phosphoric, sulfuric, and tartaric acids. If the compounds of Formula (I) simultaneously contain acidic and basic groups in the molecule, the disclosure also includes, in addition to the salt forms mentioned, inner salts or betaines (zwitterions). Salts can be obtained from the compounds of Formula (I) by customary methods which are known to the person skilled in the art, for example, by combination with an organic or inorganic acid or base in a solvent or dispersant, or by anion exchange or cation exchange from other salts. The present disclosure also includes all salts of the compounds of Formula (I) which, owing to low physiological compatibility, are not directly suitable for use in pharmaceuticals but which can be used, for example, as intermediates for chemical reactions or for the preparation of pharmaceutically acceptable salts.

Furthermore, compounds of the present disclosure may exist in amorphous form and/or one or more crystalline forms, and as such all amorphous and crystalline forms and mixtures thereof of the compounds of Formula (I), including the Examples, are intended to be included within the scope of the present disclosure. In addition, some of the compounds of the instant disclosure may form solvates with water (i.e., a hydrate) or common organic solvents such as but not limited to ethyl acetate. Such solvates and hydrates, particularly the pharmaceutically acceptable solvates and hydrates, of the instant compounds are likewise encompassed within the scope of this disclosure, along with un-solvated and anhydrous forms.

Any pharmaceutically acceptable pro-drug modification of a compound of this disclosure which results in conversion in vivo to a compound within the scope of this disclosure is also within the scope of this disclosure.

The present disclosure also relates to processes for the preparation of the compounds of Formula (I) which are described in the following and by which the compounds of the disclosure are obtainable.

The terms "therapeutically effective (or efficacious) amount" and similar descriptions such as "an amount efficacious for treatment" are intended to mean that amount of a compound of Formula (I) that will elicit the biological or medical response of a tissue, a system, animal or human that is being sought by a researcher, veterinarian, medical doctor or other clinician. In a preferred embodiment, the term "therapeutically effective amount" means an amount of a compound of Formula (I) that alleviates at least one clinical symptom in a human patient. The terms "prophylactically effective (or efficacious) amount" and similar descriptions such as "an amount efficacious for prevention" are intended to mean that amount of a compound of Formula (I) that will prevent or reduce the risk of occurrence of the biological or medical event that is sought to be prevented in a tissue, a system, animal or human by a researcher, veterinarian, medical doctor or other clinician.

Dosages of the Compounds of Formula (I)

The dosage regimen utilizing a compound of the instant disclosure is selected in accordance with a variety of factors including type, species, age, weight, sex and medical condition of the patient; the severity of the condition to be treated; the potency of the compound chosen to be administered; the route of administration; and the renal and hepatic function of the patient. A consideration of these factors is well within the purview of the ordinarily skilled clinician for the purpose of determining the therapeutically effective or prophylactically effective dosage amount needed to prevent, counter, or arrest the progress of the condition. It is understood that a specific daily dosage amount can simultaneously be both a therapeutically effective amount, e.g., for treatment of an oncological condition, and a prophylactically effective amount, e.g., for prevention of an oncological condition.

While individual needs vary, determination of optimal ranges of effective amounts of the compound of the disclosure is within the skill of the art. For administration to a human in the curative or prophylactic treatment of the conditions and disorders identified herein, for example, typical dosages of the compounds of the present disclosure can be about 0.05 mg/kg/day to about 50 mg/kg/day, for example at least 0.05 mg/kg, at least 0.08 mg/kg, at least 0.1 mg/kg, at least 0.2 mg/kg, at least 0.3 mg/kg, at least 0.4 mg/kg, or at least 0.5 mg/kg, and preferably 50 mg/kg or less, 40 mg/kg or less, 30 mg/kg or less, 20 mg/kg or less, or 10 mg/kg or less, which can be about 2.5 mg/day (0.5 mg/kg×5 kg) to about 5000 mg/day (50 mg/kg×100 kg), for example. For example, dosages of the compounds can be about 0.1 mg/kg/day to about 50 mg/kg/day, about 0.05 mg/kg/day to about 10 mg/kg/day, about 0.05 mg/kg/day to about 5 mg/kg/day, about 0.05 mg/kg/day to about 3 mg/kg/day, about 0.07 mg/kg/day to about 3 mg/kg/day, about 0.09 mg/kg/day to about 3 mg/kg/day, about 0.05 mg/kg/day to about 0.1 mg/kg/day, about 0.1 mg/kg/day to about 1 mg/kg/day, about 1 mg/kg/day to about 10 mg/kg/day, about 1 mg/kg/day to about 5 mg/kg/day, about 1 mg/kg/day to about 3 mg/kg/day, about 3 mg/day to about 500 mg/day, about 5 mg/day to about 250 mg/day, about 10 mg/day to about 100 mg/day, about 3 mg/day to about 10 mg/day, or about 100 mg/day to about 250 mg/day. Such doses may be administered in a single dose or may be divided into multiple doses.

Pharmaceutical Compositions

The compounds of Formula (I) and their pharmaceutically acceptable salts can be administered to animals, preferably to mammals, and in particular to humans, as pharmaceuticals by themselves, in mixtures with one another or in the form of pharmaceutical compositions. The term "subject" or "patient" includes animals, preferably mammals and especially humans, who use the instant active agents for the prevention or treatment of a medical condition. Administering of the drug to the subject includes both self-administration and administration to the patient by another person. The subject may be in need of, or desire, treatment for an existing disease or medical condition, or may be in need of or desire prophylactic treatment to prevent or reduce the risk of occurrence of said disease or medical condition. As used herein, a subject "in need" of treatment of an existing condition or of prophylactic treatment encompasses both a determination of need by a medical professional as well as the desire of a patient for such treatment.

The present disclosure therefore also provides the compounds of Formula (I) and their pharmaceutically acceptable salts for use as pharmaceuticals, their use for modulating the activity of mutant KRAS, HRAS and/or NRAS proteins and in particular their use in the therapy and prophylaxis of the below-mentioned diseases or disorders as well as their use for preparing medicaments for these purposes. In certain embodiments, the compounds of Formula (I) and their pharmaceutically acceptable salts inhibit the KRAS G12C protein.

Furthermore, the present disclosure provides pharmaceutical compositions which comprise as active component an effective dose of at least one compound of Formula (I) and/or a pharmaceutically acceptable salt thereof and a customary pharmaceutically acceptable carrier, i.e., one or more pharmaceutically acceptable carrier substances and/or additives.

Thus, the present disclosure provides, for example, said compound and its pharmaceutically acceptable salts for use as pharmaceutical compositions which comprise as active component an effective dose of the compound of Formula (I) and/or a pharmaceutically acceptable salt thereof and a customary pharmaceutically acceptable carrier, and the uses of said compound and/or a pharmaceutically acceptable salt thereof in the therapy or prophylaxis of the below-mentioned diseases or disorders, e.g., cancer, as well as their use for preparing medicaments for these purposes.

The pharmaceutical compositions according to the disclosure can be administered orally, for example, in the form of pills, tablets, lacquered tablets, sugar-coated tablets, granules, hard and soft gelatin capsules, aqueous, alcoholic or oily solutions, syrups, emulsions or suspensions, or rectally, for example, in the form of suppositories. Administration can also be carried out parenterally, for example subcutaneously, intramuscularly or intravenously in the form of solutions for injection or infusion.

Other suitable administration forms are, for example, percutaneous or topical administration, for example, in the form of ointments, tinctures, sprays or transdermal therapeutic systems, or, for example, microcapsules, implants or rods. The preferred administration form depends, for example, on the disease to be treated and on its severity.

The amount of active compound of Formula (I) and/or its pharmaceutically acceptable salts in the pharmaceutical composition normally is from 0.01 to 200 mg, such as from 0.1 to 200 mg, preferably from 1 to 200 mg, per dose, but depending on the type of the pharmaceutical composition, it can also be higher. In some embodiments, the amount of active compound of Formula (I) and/or its pharmaceutically acceptable salts in the pharmaceutical composition is from 0.01 to 10 mg per dose. The pharmaceutical compositions usually comprise 0.5 to 90 percent by weight of the compound of Formula (I) and/or their pharmaceutically acceptable salts. The preparation of the pharmaceutical compositions can be carried out in a manner known per se. For this purpose, one or more compounds of Formula (I) and/or their pharmaceutically acceptable salts, together with one or more solid or liquid pharmaceutical carrier substances and/or additives (or auxiliary substances) and, if desired, in combination with other pharmaceutically active compounds having therapeutic or prophylactic action, are brought into a suitable administration form or dosage form which can then be used as a pharmaceutical in human or veterinary medicine.

For the production of pills, tablets, sugar-coated tablets and hard gelatin capsules, it is possible to use, for example, lactose, starch, for example, maize starch, or starch derivatives, talc, stearic acid or its salts, etc. Carriers for soft gelatin capsules and suppositories are, for example, fats, waxes, semisolid and liquid polyols, natural or hardened oils, etc. Suitable carriers for the preparation of solutions, for example, of solutions for injection, or of emulsions or syrups are, for example, water, physiologically acceptable sodium chloride solution, alcohols such as ethanol, glycerol, polyols, sucrose, invert sugar, glucose, mannitol, vegetable oils, etc. It is also possible to lyophilize the compounds of Formula (I) and their pharmaceutically acceptable salts and to use the resulting lyophilisates, for example, for preparing preparations for injection or infusion. Suitable carriers for microcapsules, implants or rods are, for example, copolymers of glycolic acid and lactic acid.

Besides the active compounds and carriers, the pharmaceutical compositions can also contain customary additives, for example, fillers, disintegrants, binders, lubricants, wetting agents, stabilizers, emulsifiers, dispersants, preservatives, sweeteners, colorants, flavorings, aromatizers, thickeners, diluents, buffer substances, solvents, solubilizers, agents for achieving a depot effect, salts for altering the osmotic pressure, coating agents or antioxidants.

Methods of Using the Compounds of Formula (I)

The present application provides a method of inhibiting RAS-mediated cell signaling comprising contacting a cell with a compound of Formula (I) or a pharmaceutically acceptable salt thereof. Inhibition of RAS-mediated signal transduction can be assessed and demonstrated by a wide variety of ways known in the art. Non-limiting examples include (a) a decrease in GTPase activity of RAS; (b) a decrease in GTP binding affinity or an increase in GDP binding affinity; (c) an increase in $K_{off}$ of GTP or a decrease in $K_{off}$ of GDP; (d) a decrease in the levels of signaling transduction molecules downstream in the RAS pathway, such as a decrease in pMEK, pERK, or pAKT levels; and/or (e) a decrease in binding of RAS complex to downstream signaling molecules including but not limited to Raf. Kits and commercially available assays can be utilized for determining one or more of the above.

The present application also provides methods of using the compounds of Formula (I) (or their pharmaceutically acceptable salts) or pharmaceutical compositions containing such compounds to treat disease conditions, including but not limited to, conditions implicated by mutant KRAS, HRAS and/or NRAS proteins (e.g., cancer), and in some embodiments the KRAS G12C mutant.

In some embodiments, a method for treatment of cancer is provided, the method comprising administering a therapeutically effective amount a compound of Formula (I) (or a pharmaceutically acceptable salt thereof) or any of the foregoing pharmaceutical compositions comprising such a compound to a subject in need of such treatment. In some embodiments, the cancer is mediated by a KRAS, HRAS or NRAS mutation, e.g., the KRAS G12C mutation. In various embodiments, the cancer is pancreatic cancer, colorectal cancer or lung cancer. In some embodiments, the cancer is gall bladder cancer, thyroid cancer, or bile duct cancer.

In some embodiments the present disclosure provides a method of treating a disorder in a subject in need thereof, wherein said method comprises determining if the subject has a KRAS, HRAS or NRAS mutation (e.g., KRAS G12C mutation) and if the subject is determined to have the KRAS, HRAS or NRAS mutation, then administering to the subject a therapeutically effective amount of a compound of Formula (I) or a pharmaceutically acceptable salt thereof.

The disclosed compounds inhibit anchorage-independent cell growth and therefore have the potential to inhibit tumor metastasis. Accordingly, another embodiment of the present disclosure provides a method for inhibiting tumor metastasis, the method comprising administering an effective amount a compound disclosed herein.

KRAS, HRAS or NRAS mutations have also been identified in hematological malignancies (e.g., cancers that affect blood, bone marrow and/or lymph nodes). Accordingly, certain embodiments are directed to administration of the compounds of Formula (I) (e.g., in the form of a pharmaceutical composition) to a subject in need of treatment of a hematological malignancy. Such malignancies include, but are not limited to leukemias and lymphomas. For example, the presently disclosed compounds can be used for treatment of diseases such as acute lymphoblastic leukemia (ALL), acute myelogenous leukemia (AML), chronic lymphocytic leukemia (CLL), small lymphocytic lymphoma (SLL), chronic myelogenous leukemia (CML), acute monocytic leukemia (AMoL) and/or other leukemias. In other embodiments, the compounds are useful for treatment of lymphomas such as Hodgkins lymphoma or non-Hodgkins lymphoma. In various embodiments, the compounds are useful for treatment of plasma cell malignancies such as multiple myeloma, mantle cell lymphoma, and Waldenstrom's macroglubunemia.

Determining whether a tumor or cancer comprises a KRAS, HRAS or NRAS mutation (e.g., the KRAS G12C mutation) can be undertaken by assessing the nucleotide sequence encoding the KRAS, HRAS or NRAS protein, by assessing the amino acid sequence of the KRAS, HRAS or NRAS protein, or by assessing the characteristics of a putative KRAS, HRAS or NRAS mutant protein. The sequences of wild-type human KRAS, HRAS or NRAS are known in the art.

Methods for detecting a mutation in a KRAS, HRAS or NRAS nucleotide sequence are also known by those of skill in the art. These methods include, but are not limited to, polymerase chain reaction-restriction fragment length polymorphism (PCR-RFLP) assays, polymerase chain reaction-single strand conformation polymorphism (PCR—SSCP) assays, real-time PCR assays, PCR sequencing, mutant allele-specific PCR amplification (MASA) assays, direct sequencing, primer extension reactions, electrophoresis, oligonucleotide ligation assays, hybridization assays, TaqMan assays, SNP genotyping assays, high resolution melting assays and microarray analyses. In some embodiments, samples are evaluated for KRAS, HRAS or NRAS mutations (e.g., the KRAS G12C mutation) by real-time PCR. In real-time PCR, fluorescent probes specific for the KRAS, HRAS or NRAS G12C mutation are used. When a mutation is present, the probe binds and fluorescence is detected. In some embodiments, the KRAS, HRAS or NRAS mutation is identified using a direct sequencing method of specific regions (e.g., exon 2 and/or exon 3) in the KRAS, HRAS or NRAS gene.

Methods for detecting a mutation in a KRAS, HRAS or NRAS protein (e.g., the KRAS G12C mutation) are known by those of skill in the art. These methods include, but are not limited to, detection of a KRAS, HRAS or NRAS mutant using a binding agent (e.g., an antibody) specific for the mutant protein, protein electrophoresis and Western blotting, and direct peptide sequencing.

A number of tissue samples can be assessed for determining whether a tumor or cancer comprises a KRAS, HRAS or NRAS mutation (e.g., the KRAS G12C mutation). In some embodiments, the sample is taken from a subject having a tumor or cancer. In some embodiments, the sample is a fresh tumor/cancer sample. In some embodiments, the sample is a frozen tumor/cancer sample. In some embodiments, the sample is a formalin-fixed paraffin-embedded sample. In some embodiments, the sample is a circulating tumor cell (CTC) sample. In some embodiments, the sample is processed to a cell lysate. In some embodiments, the sample is processed to DNA or RNA.

The present application also provides a method of treating a hyperproliferative disorder comprising administering a therapeutically effective amount of a compound of the disclosure, or a pharmaceutically acceptable salt thereof to a subject in need thereof. In some embodiments, said method relates to the treatment of a subject who suffers from a cancer such as acute myeloid leukemia, cancer in adolescents, adrenocortical carcinoma childhood, AIDS-related cancers (e.g., Lymphoma and Kaposi's Sarcoma), anal cancer, appendix cancer, astrocytomas, atypical teratoid, basal cell carcinoma, bile duct cancer, bladder cancer, bone cancer, brain stem glioma, brain tumor, breast cancer, bronchial tumors, Burkitt lymphoma, carcinoid tumor, atypical teratoid, embryonal tumors, germ cell tumor, primary lymphoma, cervical cancer, childhood cancers, chordoma, cardiac tumors, chronic lymphocytic leukemia (CLL), chronic myelogenous leukemia (CML), chronic myleoproliferative disorders, colon cancer, colorectal cancer, craniopharyngioma, cutaneous T-cell lymphoma, extrahepatic ductal carcinoma in situ (DCIS), embryonal tumors, CNS cancer, endometrial cancer, ependymoma, esophageal cancer, esthesioneuroblastoma, ewing sarcoma, extracranial germ cell tumor, extragonadal germ cell tumor, eye cancer, fibrous histiocytoma of bone, gall bladder cancer, gastric cancer, gastrointestinal carcinoid tumor, gastrointestinal stromal tumors (GIST), germ cell tumor, gestational trophoblastic tumor, hairy cell leukemia, head and neck cancer, heart cancer, liver cancer, Hodgkin lymphoma, hypopharyngeal cancer, intraocular melanoma, islet cell tumors, pancreatic neuroendocrine tumors, kidney cancer, laryngeal cancer, lip and oral cavity cancer, liver cancer, lobular carcinoma in situ (LCIS), lung cancer, lymphoma, metastatic squamous neck cancer with occult primary, midline tract carcinoma, mouth cancer; multiple endocrine neoplasia syndromes, multiple myeloma/plasma cell neoplasm, mycosis fungoides, myelodysplasia syndromes, myelodysplastic/myeloproliferative neoplasms, multiple myeloma, merkel cell carcinoma, malignant mesothelioma, malignant fibrous histiocytoma of bone and osteosarcoma, nasal cavity and paranasal sinus cancer, nasopharyngeal cancer, neuroblastoma, non-hodgkin lymphoma, non-small cell lung cancer (NSCLC), oral cancer, lip and oral cavity cancer, oropharyngeal cancer, ovarian cancer, pancreatic cancer, papillomatosis, paraganglioma, paranasal sinus and nasal cavity cancer, parathyroid cancer, penile cancer, pharyngeal cancer, pleuropulmonary blastoma, primary central nervous system (CNS) lymphoma, prostate cancer, rectal cancer, transitional cell cancer, retinoblastoma, rhabdomyosarcoma, salivary gland cancer, skin cancer, stomach (gastric) cancer, small cell lung cancer; small intestine cancer, soft tissue sarcoma, T-Cell lymphoma, testicular cancer, throat cancer, thymoma and thymic carcinoma, thyroid cancer, transitional cell cancer of the renal pelvis and ureter, trophoblastic tumor, unusual cancers of childhood, urethral cancer, uterine sarcoma, vaginal cancer, vulvar cancer, or viral-induced cancer. In some embodiments, said method relates to the treatment of a non-cancerous hyperproliferative disorder such as benign hyperplasia of the skin (e.g., psoriasis), restenosis, or prostate (e.g., benign prostatic hypertrophy (BPH)).

In some embodiments, the methods for treatment are directed to treating lung cancers, and the methods comprise administering a therapeutically effective amount of the compounds of the disclosure (or pharmaceutical composition comprising such compounds) to a subject in need thereof. In certain embodiments, the lung cancer is a non-small cell lung carcinoma (NSCLC), for example, adenocarcinoma, squamous-cell lung carcinoma or large-cell lung carcinoma. In some embodiments, the lung cancer is a small cell lung carcinoma. Other lung cancers which the compounds of Formula (I) may provide therapeutic benefit for include, but are not limited to, glandular tumors, carcinoid tumors and undifferentiated carcinomas.

The present disclosure also provides methods of modulating a mutant KRAS, HRAS or NRAS protein activity (e.g., activity resulting from the KRAS G12C mutation) by contacting the protein with an effective amount of a compound of Formula (I). Modulation can be inhibiting or activating protein activity. In some embodiments, the present disclosure provides methods of inhibiting protein activity by contacting the mutant KRAS, HRAS or NRAS protein (e.g., KRAS G12C mutant) with an effective amount of a compound of Formula (I) in solution. In some embodiments, the present disclosure provides methods of inhibiting the mutant KRAS, HRAS or NRAS protein activity by contacting a cell, tissue, or organ that expresses the protein of interest. In some embodiments, the disclosure provides methods of inhibiting protein activity in subjects including, but not limited to, rodents and mammals (e.g., humans) by administering into the subjects an effective amount of a compound of Formula (I).

Combination Therapies

One or more additional pharmacologically active agents may be administered in combination with a compound of Formula (I) (or a pharmaceutically acceptable salt thereof). An additional active agent (or agents) is intended to mean a pharmaceutically active agent (or agents) that is active in the body, including pro-drugs that convert to pharmaceutically active form after administration, which are different from the compound of Formula (I). The additional active agents also include free-acid, free-base and pharmaceutically acceptable salts of said additional active agents. Generally, any suitable additional active agent or agents, including chemotherapeutic agents or therapeutic antibodies, may be used in any combination with the compound of Formula (I) in a single dosage formulation (e.g., a fixed dose drug combination), or in one or more separate dosage formulations which allows for concurrent or sequential administration of the active agents (co-administration of the separate active agents) to subjects. In addition, the compounds of Formula (I) (or pharmaceutically acceptable salts thereof) can be administered in combination with radiation therapy, hormone therapy, surgery or immunotherapy.

The present application also provides methods for combination therapies in which the additional active agent is known to modulate other pathways, or other components of the same pathway, or even overlapping sets of target enzymes which are used in combination with a compound of Formula (I), or a pharmaceutically acceptable salt thereof. In one embodiment, such therapy includes, but is not limited to, the combination of one or more compounds of Formula (I) with chemotherapeutic agents, immunotherapeutic agents, hormonal and anti-hormonal agents, targeted therapy agents, and anti-angiogenesis agents, to provide a synergistic or additive therapeutic effect. In another embodiment, such therapy includes radiation treatment to provide a synergistic or additive therapeutic effect.

Examples of additional active agents (i.e., additional anti-cancer agents) include chemotherapeutic agents (e.g., cytotoxic agents), immunotherapeutic agents, hormonal and anti-hormonal agents, targeted therapy agents, and anti-angiogenesis agents. Many anti-cancer agents can be classified within one or more of these groups. While certain anti-cancer agents have been categorized within a specific group(s) or subgroup(s) herein, many of these agents can also be listed within one or more other group(s) or subgroup(s), as would be presently understood in the art. It is to be understood that the classification herein of a particular agent into a particular group is not intended to be limiting. Many anti-cancer agents are presently known in the art and can be used in combination with the compounds of the present disclosure.

Further, an agent can be an agonist, antagonist, allosteric modulator, toxin or, more generally, may act to inhibit or stimulate its target (e.g., receptor or enzyme activation or inhibition). For example, suitable for use are one or more agents (e.g., antibodies, antigen binding regions, or soluble receptors) that specifically bind and inhibit the activity of growth factors, such as antagonists of hepatocyte growth factor (HGF, also known as Scatter Factor), and antibodies or antigen binding regions that specifically bind its receptor "c-met".

In an embodiment, the additional anti-cancer agent is a chemotherapeutic agent, an immunotherapeutic agent, a hormonal agent, an anti-hormonal agent, a targeted therapy agent, or an anti-angiogenesis agent (or angiogenesis inhibitor). In an embodiment, the additional anti-cancer agent is selected from the group consisting of a chemotherapeutic agent, a mitotic inhibitor, a plant alkaloid, an alkylating agent, an anti-metabolite, a platinum analog, an enzyme, a topoisomerase inhibitor, a retinoid, an aziridine, an antibiotic, a hormonal agent, an anti-hormonal agent, an anti-estrogen, an anti-androgen, an anti-adrenal, an androgen, a targeted therapy agent, an immunotherapeutic agent, a biological response modifier, a cytokine inhibitor, a tumor vaccine, a monoclonal antibody, an immune checkpoint inhibitor, an anti-PD-1 agent, an anti-PD-L1 agent, a colony-stimulating factor, an immunomodulator, an immunomodulatory imide (IMiD), an anti-CTLA4 agent, an anti-LAG1 agent, an anti-OX40 agent, a GITR agonist, a CAR-T cell, a BiTE, a signal transduction inhibitor, a growth factor inhibitor, a tyrosine kinase inhibitor, an EGFR inhibitor, a histone deacetylase (HDAC) inhibitor, a proteasome inhibitor, a cell-cycle inhibitor, an anti-angiogenesis agent, a matrix-metalloproteinase (MMP) inhibitor, a hepatocyte growth factor inhibitor, a TOR inhibitor, a KDR inhibitor, a VEGF inhibitor, a HIF-1α inhibitor a HIF-2α inhibitor, a fibroblast growth factor (FGF) inhibitor, a RAF inhibitor, a MEK inhibitor, an ERK inhibitor, a PI3K inhibitor, an AKT inhibitor, an MCL-1 inhibitor, a BCL-2 inhibitor, an SHP2 inhibitor, a HER-2 inhibitor, a BRAF-inhibitor, a gene expression modulator, an autophagy inhibitor, an apoptosis inducer, an antiproliferative agent, and a glycolysis inhibitor.

In one embodiment, the additional anti-cancer agent(s) is a chemotherapeutic agent. Non-limiting examples of chemotherapeutic agents include mitotic inhibitors and plant alkaloids, alkylating agents, anti-metabolites, platinum analogs, enzymes, topoisomerase inhibitors, retinoids, aziridines, and antibiotics.

Non-limiting examples of mitotic inhibitors and plant alkaloids include taxanes such as cabazitaxel, docetaxel, larotaxel, ortataxel, paclitaxel, and tesetaxel; demecolcine; epothilone; eribulin; etoposide (VP-16); etoposide phosphate; navelbine; noscapine; teniposide; thaliblastine; vinblastine; vincristine; vindesine; vinflunine; and vinorelbine.

Non-limiting examples of alkylating agents include nitrogen mustards such as chlorambucil, chlornaphazine, cholophosphamide, cytophosphane, estramustine, ifosfamide, mannomustine, mechlorethamine, mechlorethamine oxide hydrochloride, melphalan, novembichin, phenesterine, prednimustine, tris(2-chloroethyl)amine, trofosfamide, and uracil mustard; alkyl sulfonates such as busulfan, improsulfan, and piposulfan; nitrosoureas such as carmustine, chlorozotocin, fotemustine, lomustine, nimustine, ranimustine, streptozotocin, and TA-07; ethylenimines and methylamelamines such as altretamine, thiotepa, triethylenemelamine, triethylenethiophosphaoramide, trietylenephosphoramide, and trimethylolomelamine; ambamustine; bendamustine; dacarbazine; etoglucid; irofulven; mafosfamide; mitobronitol; mitolactol; pipobroman; procarbazine; temozolomide; treosulfan; and triaziquone.

Non-limiting examples of anti-metabolites include folic acid analogues such as aminopterin, denopterin, edatrexate, methotrexate, pteropterin, raltitrexed, and trimetrexate; purine analogs such as 6-mercaptopurine, 6-thioguanine, fludarabine, forodesine, thiamiprine, and thioguanine; pyrimidine analogs such as 5-fluorouracil (5-FU), 6-azauridine, ancitabine, azacytidine, capecitabine, carmofur, cytarabine, decitabine, dideoxyuridine, doxifiuridine, doxifluridine, enocitabine, floxuridine, galocitabine, gemcitabine, and sapacitabine; 3-aminopyridine-2-carboxaldehyde thiosemicarbazone; broxuridine; cladribine; cyclophosphamide; cytarabine; emitefur; hydroxyurea; mercaptopurine; nelarabine; pemetrexed; pentostatin; tegafur; and troxacitabine.

Non-limiting examples of platinum analogs include carboplatin, cisplatin, dicycloplatin, heptaplatin, lobaplatin, nedaplatin, oxaliplatin, satraplatin, and triplatin tetranitrate.

Non-limiting examples of enzymes include asparaginase and pegaspargase.

Non-limiting examples of topoisomerase inhibitors include acridine carboxamide, amonafide, amsacrine, belotecan, elliptinium acetate, exatecan, indolocarbazole, irinotecan, lurtotecan, mitoxantrone, razoxane, rubitecan, SN-38, sobuzoxane, and topotecan.

Non-limiting examples of retinoids include alitretinoin, bexarotene, fenretinide, isotretinoin, liarozole, RH retinamide, and tretinoin.

Non-limiting examples of aziridines include benzodopa, carboquone, meturedopa, and uredopa.

Non-limiting examples of antibiotics include intercalating antibiotics; anthracenediones; anthracycline antibiotics such as aclarubicin, amrubicin, daunomycin, daunorubicin, doxorubicin, epirubicin, idarubicin, menogaril, nogalamycin, pirarubicin, and valrubicin; 6-diazo-5-oxo-L-norleucine; aclacinomysins; actinomycin; authramycin; azaserine; bleomycins; cactinomycin; calicheamicin; carabicin; carminomycin; carzinophilin; chromomycins; dactinomycin; detorubicin; esorubicin; esperamicins; geldanamycin; marcellomycin; mitomycins; mitomycin C; mycophenolic acid; olivomycins; novantrone; peplomycin; porfiromycin; potfiromycin; puromycin; quelamycin; rebeccamycin; rodorubicin; streptonigrin; streptozocin; tanespimycin; tubercidin; ubenimex; zinostatin; zinostatin stimalamer; and zorubicin.

In one embodiment, the additional anti-cancer agent(s) is a hormonal and/or anti-hormonal agent (i.e., hormone therapy). Non-limiting examples of hormonal and anti-hormonal agents include anti-androgens such as abiraterone, apalutamide, bicalutamide, darolutamide, enzalutamide, flutamide, goserelin, leuprolide, and nilutamide; anti-estrogens such as 4-hydroxy tamoxifen, aromatase inhibiting 4(5)-imidazoles, EM-800, fosfestrol, fulvestrant, keoxifene, LY 117018, onapristone, raloxifene, tamoxifen, toremifene, and trioxifene; anti-adrenals such as aminoglutethimide, dexaminoglutethimide, mitotane, and trilostane; androgens such as calusterone, dromostanolone propionate, epitiostanol, mepitiostane, and testolactone; abarelix; anastrozole; cetrorelix; deslorelin; exemestane; fadrozole; finasteride; formestane; histrelin (RL 0903); human chorionic gonadotropin; lanreotide; LDI 200 (Milkhaus); letrozole; leuprorelin; mifepristone; nafarelin; nafoxidine; osaterone; prednisone; thyrotropin alfa; and triptorelin.

In one embodiment, the additional anti-cancer agent(s) is an immunotherapeutic agent (i.e., immunotherapy). Non-limiting examples of immunotherapeutic agents include biological response modifiers, cytokine inhibitors, tumor vaccines, monoclonal antibodies, immune checkpoint inhibitors, colony-stimulating factors, and immunomodulators.

Non-limiting examples of biological response modifiers, including cytokine inhibitors (cytokines) such as interferons and interleukins, include interferon alfa/interferon alpha such as interferon alfa-2, interferon alfa-2a, interferon alfa-2b, interferon alfa-n1, interferon alfa-n3, interferon alfacon-1, peginterferon alfa-2a, peginterferon alfa-2b, and leukocyte alpha interferon; interferon beta such as interferon beta-1a, and interferon beta-1b; interferon gamma such as natural interferon gamma-1a, and interferon gamma-1b; aldesleukin; interleukin-1 beta; interleukin-2; oprelvekin; sonermin; tasonermin; and virulizin.

Non-limiting examples of tumor vaccines include APC 8015, AVICINE, bladder cancer vaccine, cancer vaccine (Biomira), gastrin 17 immunogen, Maruyama vaccine, melanoma lysate vaccine, melanoma oncolysate vaccine (New York Medical College), melanoma vaccine (New York University), melanoma vaccine (Sloan Kettering Institute), TICE® BCG (Bacillus Calmette-Guerin), and viral melanoma cell lysates vaccine (Royal Newcastle Hospital).

Non-limiting examples of monoclonal antibodies include abagovomab, adecatumumab, aflibercept, alemtuzumab, blinatumomab, brentuximab vedotin, CA 125 MAb (Biomira), cancer MAb (Japan Pharmaceutical Development), daclizumab, daratumumab, denosumab, edrecolomab, gemtuzumab zogamicin, HER-2 and Fc MAb (Medarex), ibritumomab tiuxetan, idiotypic 105AD7 MAb (CRC Technology), idiotypic CEA MAb (Trilex), ipilimumab, lintuzumab, LYM-1-iodine 131 MAb (Techni clone), mitumomab, moxetumomab, ofatumumab, polymorphic epithelial mucin-yttrium 90 MAb (Antisoma), ranibizumab, rituximab, and trastuzumab.

Non-limiting examples of immune checkpoint inhibitors include anti-PD-1 agents or antibodies such as cemiplimab, nivolumab, and pembrolizumab; anti-PD-L1 agents or antibodies such as atezolizumab, avelumab, and durvalumab; anti-CTLA-4 agents or antibodies such as ipilumumab; anti-LAG1 agents; and anti-OX40 agents.

Non-limiting examples of colony-stimulating factors include darbepoetin alfa, epoetin alfa, epoetin beta, filgrastim, granulocyte macrophage colony stimulating factor, lenograstim, leridistim, mirimostim, molgramostim, nartograstim, pegfilgrastim, and sargramostim.

Non-limiting examples of additional immunotherapeutic agents include BiTEs, CAR-T cells, GITR agonists, imiquimod, immunomodulatory imides (IMiDs), mismatched double stranded RNA (Ampligen), resiquimod, SRL 172, and thymalfasin.

In one embodiment, the additional anti-cancer agent(s) is a targeted therapy agent (i.e., targeted therapy). Targeted therapy agents include, for example, monoclonal antibodies and small molecule drugs. Non-limiting examples of targeted therapy agents include signal transduction inhibitors, growth factor inhibitors, tyrosine kinase inhibitors, EGFR inhibitors, histone deacetylase (HDAC) inhibitors, proteasome inhibitors, cell-cycle inhibitors, angiogenesis inhibitors, matrix-metalloproteinase (MMP) inhibitors, hepatocyte growth factor inhibitors, TOR inhibitors, KDR inhibitors, VEGF inhibitors, fibroblast growth factors (FGF) inhibitors, MEK inhibitors, ERK inhibitors, PI3K inhibitors, AKT inhibitors, MCL-1 inhibitors, BCL-2 inhibitors, SHP2 inhibitors, HER-2 inhibitors, BRAF-inhibitors, gene expression modulators, autophagy inhibitors, apoptosis inducers, antiproliferative agents, and glycolysis inhibitors.

Non-limiting examples of signal transduction inhibitors include tyrosine kinase inhibitors, multiple-kinase inhibitors, anlotinib, avapritinib, axitinib, dasatinib, dovitinib, imatinib, lenvatinib, lonidamine, nilotinib, nintedanib, pazopanib, pegvisomant, ponatinib, vandetanib, and EGFR inhibitory agents.

Non-limiting examples of EGFR inhibitory agents include small molecule antagonists of EGFR such as afatinib, brigatinib, erlotinib, gefitinib, lapatinib, and osimertinib; and antibody-based EGFR inhibitors, including any anti-EGFR antibody or antibody fragment that can partially or completely block EGFR activation by its natural ligand. Antibody-based EGFR inhibitory agents may include, for example, those described in Modjtahedi, H., et al., 1993, Br. J. Cancer 67:247-253; Teramoto, T., et al., 1996, Cancer 77:639-645; Goldstein et al, 1995, Clin. Cancer Res. 1: 1311-1318; Huang, S. M., et al., 1999, Cancer Res. 15:59(8): 1935-40; and Yang, X., et al., 1999, Cancer Res. 59: 1236-1243; monoclonal antibody Mab E7.6.3 (Yang, 1999 supra); Mab C225 (ATCC Accession No. HB-8508), or an antibody or antibody fragment having the binding specificity thereof; specific antisense nucleotide or siRNA; afatinib, cetuximab; matuzumab; necitumumab; nimotuzumab; panitumumab; and zalutumumab.

Non-limiting examples of histone deacetylase (HDAC) inhibitors include belinostat, panobinostat, romidepsin, and vorinostat.

Non-limiting examples of proteasome inhibitors include bortezomib, carfilzomib, ixazomib, marizomib (salinosporamide a), and oprozomib.

Non-limiting examples of cell-cycle inhibitors, including CDK inhibitors, include abemaciclib, alvocidib, palbociclib, and ribociclib.

In one embodiment, the additional anti-cancer agent(s) is an anti-angiogenic agent (or angiogenesis inhibitor) including, but not limited to, matrix-metalloproteinase (MMP) inhibitors; VEGF inhibitors; EGFR inhibitors; TOR inhibitors such as everolimus and temsirolimus; PDGFR kinase inhibitory agents such as crenolanib; HIF-1$\alpha$ inhibitors such as PX 478; HIF-2$\alpha$ inhibitors such as belzutifan and the HIF-2$\alpha$ inhibitors described in WO 2015/035223; fibroblast growth factor (FGF) or FGFR inhibitory agents such as B-FGF and RG 13577; hepatocyte growth factor inhibitors; KDR inhibitors; anti-Angl and anti-Ang2 agents; anti-Tie2 kinase inhibitory agents; Tek antagonists (US 2003/0162712; U.S. Pat. No. 6,413,932); anti-TWEAK agents (U.S. Pat. No. 6,727,225); ADAM distintegrin domain to antagonize the binding of integrin to its ligands (US 2002/0042368); anti-eph receptor and/or anti-ephrin antibodies or antigen binding regions (U.S. Pat. Nos. 5,981,245; 5,728,813; 6,596,852; 6,232,447; and 6,057,124); and anti-PDGF-BB antagonists as well as antibodies or antigen binding regions specifically binding to PDGF-BB ligands.

Non-limiting examples of matrix-metalloproteinase (MMP) inhibitors include MMP-2 (matrix-metalloproteinase 2) inhibitors, MMP-9 (matrix-metalloproteinase 9) inhibitors, prinomastat, RO 32-3555, and RS 13-0830. Examples of useful matrix metalloproteinase inhibitors are described, for example, in WO 96/33172, WO 96/27583, EP 1004578, WO 98/07697, WO 98/03516, WO 98/34918, WO 98/34915, WO 98/33768, WO 98/30566, EP 0606046, EP 0931788, WO 90/05719, WO 99/52910, WO 99/52889, WO 99/29667, WO 1999/007675, EP 1786785, EP 1181017, US 2009/0012085, U.S. Pat. Nos. 5,863,949, 5,861,510, and EP 0780386. Preferred MMP-2 and MMP-9 inhibitors are those that have little or no activity inhibiting MMP-1. More preferred, are those that selectively inhibit MMP-2 and/or MMP-9 relative to the other matrix-metalloproteinases (i.e., MAP-1, MMP-3, MMP-4, MMP-5, MMP-6, MMP-7, MMP-8, MMP-10, MMP-11, MMP-12, and MMP-13).

Non-limiting examples of VEGF and VEGFR inhibitory agents include bevacizumab, cediranib, CEP 7055, CP 547632, KRN 633, orantinib, pazopanib, pegaptanib, pegaptanib octasodium, semaxanib, sorafenib, sunitinib, VEGF antagonist (Borean, Denmark), and VEGF-TRAP™.

The additional anti-cancer agent(s) may also be another anti-angiogenic agent including, but not limited to, 2-methoxyestradiol, AE 941, alemtuzumab, alpha-D148 Mab (Amgen, US), alphastatin, anecortave acetate, angiocidin, angiogenesis inhibitors, (SUGEN, US), angiostatin, anti-Vn Mab (Crucell, Netherlands), atiprimod, axitinib, AZD 9935, BAY RES 2690 (Bayer, Germany, BC 1 (Genoa Institute of Cancer Research, Italy), beloranib, benefin (Lane Labs, US), cabozantinib, CDP 791 (Celltech Group, UK), chondroitinase AC, cilengitide, combretastatin A4 prodrug, CP 564959 (OSI, US), CV247, CYC 381 (Harvard University, US), E 7820, EHT 0101, endostatin, enzastaurin hydrochloride, ER-68203-00 (IVAX, US), fibrinogen-E fragment, Flk-1 (ImClone Systems, US), forms of FLT 1 (VEGFR 1), FR-111142, GCS-100, GW 2286 (GlaxoSmithKline, UK), IL-8, ilomastat, IM-862, irsogladine, KM-2550 (Kyowa Hakko, Japan), lenalidomide, lenvatinib, MAb alpha5beta3 integrin, second generation (Applied Molecular Evolution, USA and Medlmmune, US), MAb VEGF (Xenova, UK), marimastat, maspin (Sosei, Japan), metastatin, motuporamine C, M-PGA, ombrabulin, OX14503, PI 88, platelet factor 4, PPI 2458, ramucirumab, rBPI 21 and BPI-derived antiangiogenic (XOMA, US), regorafenib, SC-236, SD-7784 (Pfizer, US), SDX 103 (University of California at San Diego, US), SG 292 (Telios, US), SU-0879 (Pfizer, US), TAN-1120, TBC-1635, tesevatinib, tetrathiomolybdate, thalidomide, thrombospondin 1 inhibitor, Tie-2 ligands (Regeneron, US), tissue factor pathway inhibitors (EntreMed, US), tumor necrosis factor-alpha inhibitors, tumstatin, TZ 93, urokinase plasminogen activator inhibitors, vadimezan, vandetanib, vasostatin, vatalanib, VE-cadherin-2 antagonists, xanthorrhizol, XL 784 (Exelixis, US), ziv-aflibercept, and ZD 6126.

In embodiments, the additional anti-cancer agent(s) is an additional active agent that disrupts or inhibits RAS-RAF-ERK or PI3K-AKT-TOR signaling pathways or is a PD-1 and/or PD-L1 antagonist. In embodiments, the additional anti-cancer agent(s) is a RAF inhibitor, EGFR inhibitor, MEK inhibitor, ERK inhibitor, PI3K inhibitor, AKT inhibitor, TOR inhibitor, MCL-1 inhibitor, BCL-2 inhibitor, SHP2 inhibitor, proteasome inhibitor, or immune therapy, including monoclonal antibodies, immunomodulatory imides (IMiDs), anti-PD-1, anti-PDL-1, anti-CTLA4, anti-LAG1, and anti-OX40 agents, GITR agonists, CAR-T cells, and BiTEs.

Non-limiting examples of RAF inhibitors include dabrafenib, encorafenib, regorafenib, sorafenib, and vemurafenib.

Non-limiting examples of MEK inhibitors include binimetinib, CI-1040, cobimetinib, PD318088, PD325901, PD334581, PD98059, refametinib, selumetinib, and trametinib.

Non-limiting examples of ERK inhibitors include LY3214996, LTT462, MK-8353, SCH772984, ravoxertinib, ulixertinib, and an ERKi as described in WO 2017/068412.

Non-limiting examples of PI3K inhibitors include 17-hydroxywortmannin analogs (e.g., WO 06/044453); AEZS-136; alpelisib; AS-252424; buparlisib; CAL263; copanlisib; CUDC-907; dactolisib (WO 06/122806); demethoxyviridin; duvelisib; GNE-477; GSK1059615; IC87114; idelalisib; INK1117; LY294002; Palomid 529; paxalisib; perifosine; PI-103; PI-103 hydrochloride; pictilisib (e.g., WO 09/036,082; WO 09/055,730); PIK 90; PWT33597; SF1126; sonolisib; TGI 00-115; TGX-221; XL147; XL-765; wortmannin; and ZSTK474.

Non-limiting examples of AKT inhibitors include Akt-1-1 (inhibits Aktl) (Barnett et al. (2005) *Biochem. J.,* 385 (Pt. 2), 399-408); Akt-1-1,2 (Barnett et al. (2005) *Biochem. J.* 385 (Pt. 2), 399-408); API-59CJ-Ome (e.g., Jin et al. (2004) Br. J. Cancer 91, 1808-12); 1-H-imidazo[4,5-c]pyridinyl compounds (e.g., WO05011700); indole-3-carbinol and derivatives thereof (e.g., U.S. Pat. No. 6,656,963; Sarkar and Li (2004) *J Nutr.* 134 (12 Suppl), 3493 S-3498S); perifosine, Dasmahapatra et al. (2004) *Clin. Cancer Res.* 10(15), 5242-52, 2004); phosphatidylinositol ether lipid analogues (e.g., Gills and Dennis (2004) *Expert. Opin. Investig. Drugs* 13, 787-97); triciribine (Yang et al. (2004) Cancer Res. 64, 4394-9); imidazooxazone compounds including trans-3-amino-1-methyl-3-[4-(3-phenyl-5H-imidazo[1,2-c]pyrido [3,4-e][1,3]oxazin-2-yl)phenyl]-cyclobutanol hydrochloride (WO 2012/137870); afuresertib; capivasertib; MK2206; patasertib, and those disclosed in WO 2011/082270 and WO 2012/177844.

Non-limiting examples of TOR inhibitors include deforolimus; ATP-competitive TORC1/TORC2 inhibitors, including PI-103, PP242, PP30, and Torin 1; TOR inhibitors in FKBP12 enhancer, rapamycins and derivatives thereof, including temsirolimus, everolimus, WO 9409010; rapalogs, e.g. as disclosed in WO 98/02441 and WO 01/14387, e.g. AP23573, AP23464, or AP23841; 40-(2-hydroxyethyl) rapamycin, 40-[3-hydroxy(hydroxymethyl)methylpropanoate]-rapamycin; 40-epi-(tetrazolyl)-rapamycin (also called ABT578); 32-deoxorapamycin; 16-pentynyloxy-32(S)-dihydrorapanycin, and other derivatives disclosed in WO 05/005434; derivatives disclosed in U.S. Pat. No. 5,258,389, WO 94/090101, WO 92/05179, U.S. Pat. Nos. 5,118,677, 5,118,678, 5,151,413, 5,120,842, WO 93/111130, WO 94/02136, WO 94/02485, WO 95/14023, WO 94/02136, WO 95/16691, WO 96/41807, WO 96/41807 and U.S. Pat. No. 5,256,790; and phosphorus-containing rapamycin derivatives (e.g., WO 05/016252).

Non-limiting examples of MCL-1 inhibitors include AMG-176, MIK665, and S63845.

Non-limiting examples of SHP2 inhibitors include SHP2 inhibitors described in WO 2019/167000 and WO 2020/022323.

Additional non-limiting examples of anti-cancer agents that are suitable for use include 2-ethylhydrazide, 2,2',2"-trichlorotriethylamine, ABVD, aceglatone, acemannan, aldophosphamide glycoside, alpharadin, amifostine, aminolevulinic acid, anagrelide, ANCER, ancestim, anti-CD22 immunotoxins, antitumorigenic herbs, apaziquone, arglabin, arsenic trioxide, azathioprine, BAM 002 (Novelos), bcl-2 (Genta), bestrabucil, biricodar, bisantrene, bromocriptine, brostallicin, bryostatin, buthionine sulfoximine, calyculin, cell-cycle nonspecific antineoplastic agents, celmoleukin, clodronate, clotrimazole, cytarabine ocfosfate, DA 3030 (Dong-A), defofamine, denileukin diftitox, dexrazoxane, diaziquone, dichloroacetic acid, dilazep, discodermolide, docosanol, doxercalciferol, edelfosine, eflornithine, EL532 (Elan), elfomithine, elsamitrucin, eniluracil, etanidazole, exisulind, ferruginol, folic acid replenisher such as frolinic acid, gacytosine, gallium nitrate, gimeracil/oteracil/tegafur combination (S-1), glycopine, histamine dihydrochloride, HIT diclofenac, HLA-B7 gene therapy (Vical), human fetal alpha fetoprotein, ibandronate, ibandronic acid, ICE chemotherapy regimen, imexon, iobenguane, IT-101 (CRLX101), laniquidar, LC 9018 (Yakult), leflunomide, lentinan, levamisole+fluorouracil, lovastatin, lucanthone, masoprocol, melarsoprol, metoclopramide, miltefosine, miproxifene, mitoguazone, mitozolomide, mopidamol, motexafin gadolinium, MX6 (Galderma), naloxone+pentazocine, nitracrine, nolatrexed, NSC 631570 octreotide (Ukrain), olaparib, P-30 protein, PAC-1, palifermin, pamidronate, pamidronic acid, pentosan polysulfate sodium, phenamet, picibanil, pixantrone, platinum, podophyllinic acid, porfimer sodium, PSK (Polysaccharide-K), rabbit antithymocyte polyclonal antibody, rasburiembodiment, retinoic acid, rhenium Re 186 etidronate, romurtide, samarium (153 Sm) lexidronam, sizofiran, sodium phenylacetate, sparfosic acid, spirogermanium, strontium-89 chloride, suramin, swainsonine, talaporfin, tariquidar, tazarotene, tegafur-uracil, temoporfin, tenuazonic acid, tetrachlorodecaoxide, thrombopoietin, tin ethyl etiopurpurin, tirapazamine, TLC ELL-12, tositumomab-iodine 131, trifluridine and tipiracil combination, troponin I (Harvard University, US), urethan, valspodar, verteporfin, zoledronic acid, and zosuquidar.

The present disclosure further provides a method for using the compounds of Formula (I) or pharmaceutical compositions provided herein, in combination with radiation therapy to treat cancer. Techniques for administering radiation therapy are known in the art, and these techniques can be used in the combination therapy described herein. The administration of the compound of Formula (I) in this combination therapy can be determined as described herein.

Radiation therapy can be administered through one of several methods, or a combination of methods, including, without limitation, external-beam therapy, internal radiation therapy, implant radiation, stereotactic radiosurgery, systemic radiation therapy, radiotherapy and permanent or temporary interstitial brachy therapy. The term "brachytherapy," as used herein, refers to radiation therapy delivered by a spatially confined radioactive material inserted into the body at or near a tumor or other proliferative tissue disease site. The term is intended, without limitation, to include exposure to radioactive isotopes (e.g., At-211, I-131, I-125, Y-90, Re-186, Re-188, Sm-153, Bi-212, P-32, and radioactive isotopes of Lu). Suitable radiation sources for use as a cell conditioner of the present disclosure include both solids and liquids. By way of non-limiting example, the radiation source can be a radionuclide, such as I-125, I-131, Yb-169, Ir-192 as a solid source, I-125 as a solid source, or other radionuclides that emit photons, beta particles, gamma radiation, or other therapeutic rays. The radioactive material can also be a fluid made from any solution of radionuclide(s), e.g., a solution of I-125 or I-131, or a radioactive fluid can be produced using a slurry of a suitable fluid containing small particles of solid radionuclides, such as Au-198, Y-90. Moreover, the radionuclide(s) can be embodied in a gel or radioactive microspheres.

The present disclosure also provides methods for combination therapies in which the additional active agent is known to modulate other pathways, or other components of the same pathway, or even overlapping sets of target enzymes which are used in combination with a compound of Formula (I), or a pharmaceutically acceptable salt thereof. In one embodiment, such therapy includes, but is not limited to, the combination of one or more compounds of Formula (I) with chemotherapeutic agents, immunotherapeutic agents, hormonal therapy agents, therapeutic antibodies, targeted therapy agents, and radiation treatment, to provide a synergistic or additive therapeutic effect.

The compounds of the disclosure can be used in combination with the agents disclosed herein or other suitable agents, depending on the condition being treated. Hence, in some embodiments the one or more compounds of the disclosure will be co-administered with other agents as described above. When used in combination therapy, the compounds described herein are administered with the second agent simultaneously or separately. This administration in combination can include simultaneous administration of the two agents in the same dosage form, simultaneous administration in separate dosage forms, and separate administration. That is, a compound of Formula (I) and any of the agents described above can be formulated together in the same dosage form and administered simultaneously. Alternatively, a compound of Formula (I) and any of the agents described above can be simultaneously administered, wherein both the agents are present in separate formulations. In another alternative, a compound of Formula (I) can be administered just followed by and any of the agents described above, or vice versa. In some embodiments of the separate administration protocol, a compound of Formula (I) and any of the agents described above are administered a few minutes apart, or a few hours apart, or a few days apart.

As one aspect of the present disclosure contemplates the treatment of the disease/conditions with a combination of pharmaceutically active compounds that may be administered separately, the disclosure further relates to combining separate pharmaceutical compositions in kit form. The kit comprises two separate pharmaceutical compositions: a compound of Formula (I), and a second pharmaceutical compound. The kit comprises a container for containing the separate compositions such as a divided bottle or a divided foil packet. Additional examples of containers include syringes, boxes, and bags. In some embodiments, the kit comprises directions for the use of the separate components. The kit form is particularly advantageous when the separate components are preferably administered in different dosage forms (e.g., oral and parenteral), are administered at different dosage intervals, or when titration of the individual components of the combination is desired by the prescribing health care professional.

The present disclosure also provides for the compound of Formula (I), or the pharmaceutically acceptable salt thereof, for use in therapy, or use of the compound of Formula (I), or the pharmaceutically acceptable salt thereof, in therapy. The present disclosure also provides for the compound of Formula (I), or the pharmaceutically acceptable salt thereof, for use in treating cancer, or use of a compound of Formula (I), or the pharmaceutically acceptable salt thereof, for treating cancer. The present disclosure also provides for the compound of Formula (I), or the pharmaceutically acceptable salt thereof, for the preparation of a medicament for the treatment of cancer, or use of the compound of Formula (I), or the pharmaceutically acceptable salt thereof, for the preparation of a medicament for the treatment of cancer. The present disclosure also provides for the compound of Formula (I), or the pharmaceutically acceptable salt thereof, and an additional anti-cancer agent, for use in the treatment of cancer, or use of the compound of Formula (I), or the pharmaceutically acceptable salt thereof, and the additional anti-cancer agent for treating cancer. The disclosure also provides the compound of Formula (I), or the pharmaceutically acceptable salt thereof, and an additional anti-cancer agent, for the preparation of a medicament for the treatment of cancer, or use of the compound of Formula (I), or the pharmaceutically acceptable salt thereof, and the additional anti-cancer agent, for the preparation of a medicament for the treatment of cancer. The present disclosure also provides for a pharmaceutical composition comprising the compound of Formula (I), or the pharmaceutically acceptable salt thereof, for use in the treatment of cancer, or use of the pharmaceutical composition comprising the compound of Formula (I), or the pharmaceutically acceptable salt thereof, for treating cancer. The present disclosure also provides for a pharmaceutical composition comprising the compound of Formula (I), or the pharmaceutically acceptable salt thereof, and an additional anti-cancer agent, for use in the treatment of cancer, or use of the pharmaceutical composition comprising the compound of Formula (I), or the pharmaceutically acceptable salt thereof, and the additional anti-cancer agent, for treating cancer.

Methods of Preparing the Compounds of the Disclosure

Several methods for preparing the compounds of this disclosure are described in the following Examples. Starting materials and intermediates are purchased, made from known procedures, or as otherwise illustrated.

Throughout the synthetic schemes and examples, abbreviations and acronyms may be used with the following meanings unless otherwise indicated:

anhydr.=Anhydrous; aq.=aqueous; atm=atmosphere; Bodipy-GDP=mixture of ((2R,3S,4R,5R)-5-(2-amino-6-oxo-1,6-dihydro-9H-purin-9-yl)-3-(((2-(3-(5,5-difluoro-7,9-dimethyl-5H-414,514-dipyrrolo[1,2-c:2',1'4][1,3,2] diazaborinin-3-yl)propanamido)ethyl)carbamoyl)oxy)-4-hydroxytetrahydrofuran-2-yl)methyl hydrogen diphosphate and ((2R,3R,4R,5R)-5-(2-amino-6-oxo-1,6-dihydro-9H-purin-9-yl)-4-(((2-(3-(5,5-difluoro-7,9-dimethyl-5H-414,514-dipyrrolo[1,2-c:2',1'-f][1,3,2]diazaborinin-3-yl)propanamido)ethyl)carbamoyl)oxy)-3-hydroxytetrahydrofuran-2-yl)methyl hydrogen diphosphate (Invitrogen™, catalog number G22360); BOP=benzotriazol-1-yloxytris(dimethylamino)phosphonium hexafluorophosphate; brs=broad singlet; Bu=butyl; t-Bu=tert-butyl; cataCxium® C=trans-Di(μ-acetato)bis[o-(di-o-tolylphosphino)benzyl]dipalladium(II), C=$CDCl_3$=deuterated chloroform; Cbz=carbobenzyl; CDI=1,1'-carbonyldiimidazole, CELITE=diatomaceous earth; $CF_3$=trifluoromethyl; cGMP=cyclic guanosine monophosphate; $CH_3NO_2$=nitromethane; conc.=concentrated; DBU=1,8-diazabicyclo[5.4.0]undec-7-ene; DCM=dichloromethane; DETA-NO=Diethylenetriamine/nitric oxide adduct; DHP=3,4-dihydropyran; DIAD=Diisopropyl azodicarboxylate; DIEA/DIPEA=N,N-Diisopropylethylamine; DME=dimethoxyethane, DMEA=N,N-Dimethylethanamine, DMF=N,N-dimethylformamide; DMP=Dess-Martin periodinane; DMS=dimethylsulfide; DMSO=dimethylsulfoxide; DPPF or dppf=1,1'-bis(diphenylphosphino)ferrocene; DTT=dithiothreitol; EDTA=ethylenediaminetetraacetic acid; equiv, eq.=equivalent(s); Et=ethyl; $Et_3N$=triethylamine; EtOAc=ethyl acetate; EtOH=ethanol; Grubbs Catalyst=(1,3-Bis(2,4,6-trimethylphenyl)-2-imidazolidinylidene)dichloro(phenylmethylene)(tricyclohexylphosphine)ruthenium; GTP=guanosine triphosphate; h=hour; HATU=1-[bis(dimethylamino)methylene]-1H-1,2,3-triazolo[4,5-b]pyridinium 3-oxid hexafluorophosphate; HEPES=4-(2-hydroxyethyl)-1-piperazineethanesulfonic acid; HMDS=hexamethydisilazane; HPLC=High pressure liquid chromatography; Int.=intermediate; iPr=isopropyl; IP=inflection points; i-PrOH=Isopropanol; KHMDS=Potassium bis(trimethylsilyl)amide; LCMS, LC/MS=liquid chromatography-mass spectrometry; min, min.=minute; LDA=lithium diisopropylamide; M=Molar; mCPBA=3-chlorobenzoperoxoic acid; Me=methyl; MeCN, ACN=acetonitrile; MeOH=methanol; mp, m.p.=melting point; mpk=milligrams per kilogram; MsCl=Methanesulfonyl chloride; MOM=methoxymethyl; MPLC=medium pressure liquid chromatography; N=Normal; NaOMe=sodium methoxide; NMR=nuclear magnetic resonance; N.D.=not determined; PDA=photodiode array; Pet. ether=petroleum ether; Pd—C=palladium on carbon; $Pd_2(dba)_3$=tris(dibenzylideneacetone)dipalladium (0); Ph=phenyl; Pr=propyl; psi=pounds per square inch gauge; $POCl_3$=phosphorus(V) oxide chloride; PPTS=pyridinium p-toluenesulfonate; PTLC, prep TLC=preparative thin layer chromatography; pTsOH=p-toluenesulfonic acid; rac=racemic; RT=retention time; RP-HPLC=reverse phase HPLC; rt=room temperature; sat.=saturated; SFC=supercritical fluid chromatography; SOS=Son of Sevenless; Sphos Pd G3=(2-Dicyclohexylphosphino-2',6'-dimethoxybiphenyl) [2-(2'-amino-1,1'-biphenyl)]palladium(II) methanesulfonate; T3P=propanephosphonic acid anhydride; TBAF=tetra-n-butylammonium fluoride; TBSCl=tert-butyldimethylsilyl chloride; $Tf_2O$=triflic anhydride; TFA=trifluoroacetic acid; THP=tetrahydropyran; TLC=thin layer chromatography; THF=tetrahydrofuran; TMS=trimethylsilyl; TWEEN=polyoxyethylene (20) sorbitan monolaurate; VCD=vibrational circular dichroism; v, v/v=volume, volume to volume; w, w/w=weight, weight to weight, XPhos=2-dicyclohexylphosphino-2',4',6'-triisopropylbiphenyl; μm=micrometer.

EXAMPLES

The compounds described herein can be prepared according to the procedures of the following schemes and examples, using appropriate materials and are further exemplified by the following specific examples. The compounds illustrated in the examples are not, however, to be construed as forming the only genus that is considered as the disclosure. The examples further illustrate details for the preparation of the compounds of the present disclosure. Those skilled in the art will readily understand that known variations of the conditions and processes of the following preparative procedures can be used to prepare these compounds. These examples are provided for the purpose of further illustration only and are not intended to be limitations on the disclosure. Any intermediates described below may be referred to herein by their number preceded by "Int-."

Concentration refers to the removal of the volatile components at reduced pressure (e.g., by rotary evaporation) unless otherwise noted. All temperatures are in degrees Celsius unless otherwise noted. Mass spectra (MS) were measured by electrospray ion-mass spectroscopy (ESI) in positive ion detection mode and m/z refers to the $[M+H]^+$ ion unless otherwise noted. $^1H$ NMR spectra were recorded at 400-600 MHz at ambient temperature unless otherwise noted. Protons reported as 0.5 H are due to rotameric signals. RP-HPLC refers to reverse-phase HPLC on C18-functionalized preparative or semi-preparative columns with gradient elution using acetonitrile and water modified with trifluoroacetic acid or ammonium hydroxide as eluents and fractions were lyophilized or concentrated by rotary evaporation unless otherwise noted. Purification by column chromatography on silica gel was accomplished using a flash chromatography system (e.g., ISCO® or Biotage®) and commercial pre-packed silica gel columns with elution using the stated solvent systems. Compounds described herein were synthesized as the racemates unless otherwise noted in the experimental procedures and compound tables. Certain products/intermediates in the examples include indication of "Peak 1" and/or "Peak 2", which refer to the order of elution of the indicated product/intermediate from the chromatography column (e.g., an SFC column) used to isolate the compound under the specified conditions. Thus, for example, Peak 1 refers to the first eluting compound, e.g., first eluting stereoisomer, under the specified conditions.

SFC Columns used in the chiral resolution of stereoisomers are summarized in the following Table:

| SFC Column | SFC Column Abbreviation |
|---|---|
| CCC (21 mm × 250 mm, 5 um) | Column A |
| Daicel Chiralpak AD (30 mm × 250 mm, 10 um) | Column B |

-continued

| SFC Column | SFC Column Abbreviation |
|---|---|
| Phenomenex-Cellulose-2 (30 mm × 250 mm, 5 um) | Column C |
| Daicel Chiralcel OJ (30 mm × 250 mm, 10 um) | Column D |
| Daicel Chiralpak OD (150 mm × 4.6 mm, 3 um) | Column E |

Preparation of Int A4: Benzyl (2S)-2-(cyanomethyl)-4-(2-(methylsulfonyl)-7-(naphthalen-1-yl)-6,7-dihydro-5H-pyrano[2,3-d]pyrimidin-4-yl)piperazine-1-carboxylate (Int A4

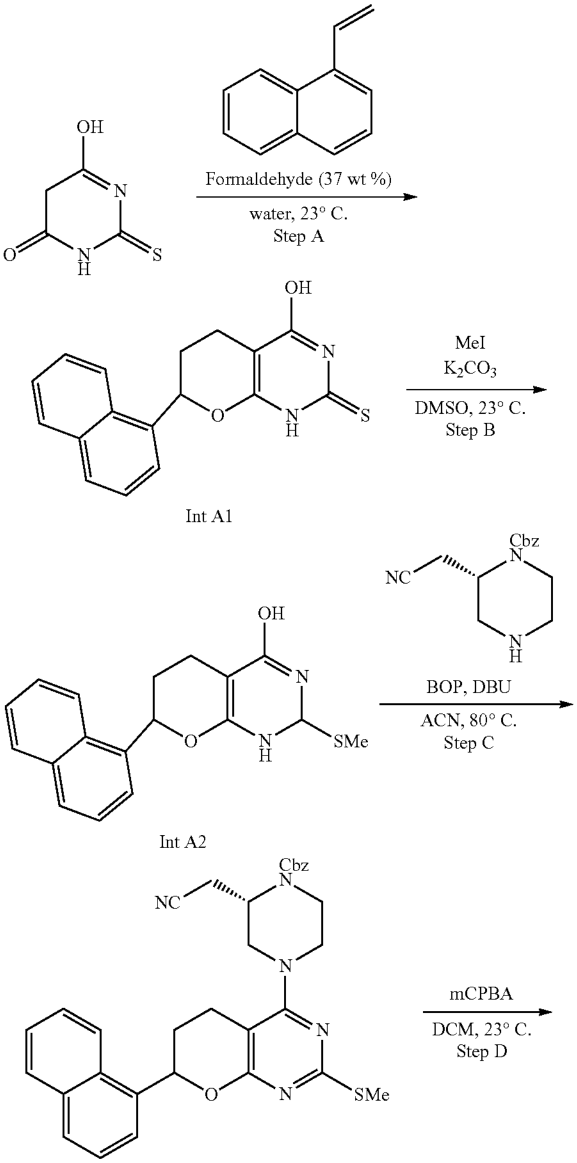

-continued

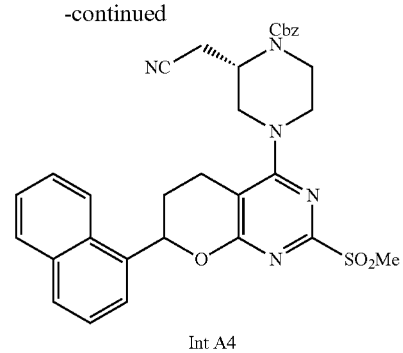

Int A4

Step A: 4-hydroxy-7-(naphthalen-1-yl)-1,5,6,7-tetrahydro-2H-pyrano[2,3-d]pyrimidine-2-thione (Int A1)

To a mixture of 1-vinylnaphthalene (1.44 mL, 9.73 mmol), 2-thioxodihydropyrimidine-4,6(1H,5H)-dione (2103 mg, 14.59 mmol), and formaldehyde (37 wt % in $H_2O$) (1.448 mL, 19.45 mmol) was added water (15 mL). The reaction mixture was stirred at room temperature overnight. The reaction was then filtered and the collected solid was dried under reduced pressure to yield 4-hydroxy-7-(naphthalen-1-yl)-1,5,6,7-tetrahydro-2H-pyrano[2,3-d]pyrimidine-2-thione (Int A1). MS (ESI) $[M+H]^+$ m/z: 311.

Step B: 2-(methylthio)-7-(naphthalen-1-yl)-6,7-dihydro-5H-pyrano[2,3-d]pyrimidin-4-ol (Int A2)

4-hydroxy-7-(naphthalen-1-yl)-1,5,6,7-tetrahydro-2H-pyrano[2,3-d]pyrimidine-2-thione (Int A1) (650 mg, 2.09 mmol) was dissolved in DMSO (8 mL) and potassium carbonate (347 mg, 2.51 mmol) and iodomethane (0.131 mL, 2.094 mmol) were added. The reaction mixture was stirred for minutes at room temperature. The reaction mixture was then diluted with 5 mL water and a fine white powder formed. The suspension was filtered using a F porosity frit to yield 2-(methylthio)-7-(naphthalen-1-yl)-6,7-dihydro-5H-pyrano[2,3-d]pyrimidin-4-ol (Int A2). MS (ESI) $[M+H]^+$ m/z: 325.

Step C: benzyl (2S)-2-(cyanomethyl)-4-(2-(methylthio)-7-(naphthalen-1-yl)-6,7-dihydro-5H-pyranor2,3-dipyrimidin-4-yl)piperazine-1-carboxylate (Int A3)

To a solution of 2-(methylthio)-7-(naphthalen-1-yl)-6,7-dihydro-5H-pyrano[2,3-d]pyrimidin-4-ol (Int A2) (260 mg, 0.801 mmol) in acetonitrile (3.5 mL) was added benzyl 2-(cyanomethyl)piperazine-1-carboxylate (416 mg, 1.60 mmol), BOP (461 mg, 1.04 mmol) followed by DBU (366 μL, 2.40 mmol). The resulting mixture were heated at 80° C. overnight. The reaction mixture was quenched with water (5 mL) and extracted with EtOAc (3×5 mL). The combined organic layers were concentrated and purified using 24 g silica gel column with 30% of EtOAc in hexanes to yield benzyl (2S)-2-(cyanomethyl)-4-(2-(methylthio)-7-(naphthalen-1-yl)-6,7-dihydro-5H-pyrano[2,3-d]pyrimidin-4-yl)piperazine-1-carboxylate (Int A3). MS (ESI): $[M+H]^+$ m/z: 566.

Step D: Benzyl (2S)-2-(cyanomethyl)-4-(2-(methylsulfonyl)-7-(naphthalen-1-yl)-6,7-dihydro-5H-pyrano[2,3-d]pyrimidin-4-yl)piperazine-1-carboxylate (Int A4)

A mixture of benzyl (2S)-2-(cyanomethyl)-4-(2-(methylthio)-7-(naphthalen-1-yl)-6,7-dihydro-5H-pyrano[2,3-d]pyrimidin-4-yl)piperazine-1-carboxylate (Int A3) (260 mg, 0.460 mmol) and 3-chlorobenzoperoxoic acid (238 mg, 1.38 mmol) in DCM (2.5 mL) was stirred at room temperature for 3 hrs. The reaction mixture was diluted with DCM, filtered and the filtrate was washed with saturated, aqueous $NaHCO_3$ solution. The combined organic layers were concentrated to yield benzyl (2S)-2-(cyanomethyl)-4-(2-(methylsulfonyl)-7-(naphthalen-1-yl)-6,7-dihydro-5H-pyrano[2,3-d]pyrimidin-4-yl)piperazine-1-carboxylate (Int A4). MS (ESI): $[M+H]^+$ m/z: 598.

Preparation of Int B1: 1-methyl-8-vinylnaphthalene

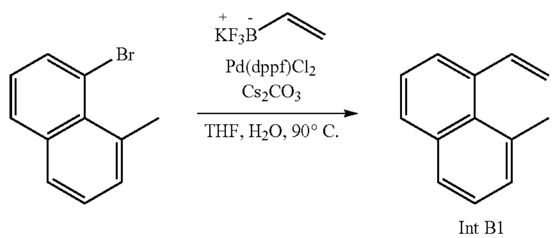

Int B1

1-Methyl-8-vinylnaphthalene (Int B1)

To a solution of 1-bromo-8-methylnaphthalene (5.0 g, 22.61 mmol) in THF (45.0 mL) and water (5.0 mL) was added $Cs_2CO_3$ (22.11 g, 67.8 mmol), potassium trifluoro (vinyl)borate (4.54 g, 33.9 mmol) and [1,1'-bis(diphenylphosphino)ferrocene]dichloropalladium(II) (1.655 g, 2.261 mmol) at 25° C. under $N_2$ atmosphere. The mixture was stirred at 90° C. for 15 h. The mixture was cooled, filtered and the solvent was diluted with water (50 mL), extracted with EtOAc (3×60 mL), washed with brine (2×100 mL), dried over $Na_2SO_4$, filtered and the solvent was evaporated under reduced pressure to give the crude product. The crude product was purified by flash silica gel chromatography using an eluent of 100% petroleum ether gradient to give 1-methyl-8-vinylnaphthalene (Int B1). $^1H$ NMR (500 MHz, $CDCl_3$) δ: 7.62 (dd, J=1.8, 7.8 Hz, 1H), 7.57-7.48 (m, 2H), 7.29-7.22 (m, 2H), 7.21-7.16 (m, 1H), 7.16-7.12 (m, 1H), 5.33 (dd, J=1.8, 17.1 Hz, 1H), 5.18 (dd, J=1.9, 10.8 Hz, 1H), 2.73 (s, 3H).

Preparation of Int C1: 3-fluoro-2-vinylphenol

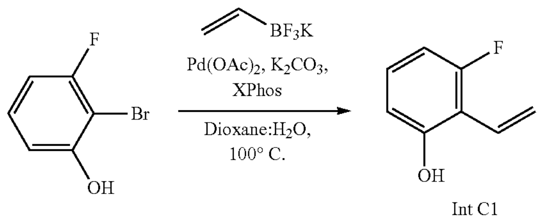

Int C1

3-Fluoro-2-vinylphenol (Int C1)

To a stirred solution of 2-bromo-3-fluorophenol (10 g, 52.4 mmol), potassium vinyltrifluoroborate (28.1 g, 209 mmol), potassium carbonate (21.71 g, 157 mmol) in 1,4-dioxane (50 mL) and water (250 mL) were added $Pd(OAc)_2$ (0.588 g, 2.62 mmol) and XPhos (2.496 g, 5.24 mmol) at 25° C. under $N_2$ atmosphere, and the mixture was stirred at 100° C. for 12 h under $N_2$ atmosphere. TLC ($SiO_2$, Pet. ether: EtOAc=5:1) showed the starting material was consumed. The reaction mixture was quenched with water (25 mL), and the resulting mixture was extracted with EtOAc (100 mL×3). The combined organic phase was dried over anhydrous $Na_2SO_4$, filtered and concentrated in vacuo. The residue was further purified by flash silica gel chromatography using an eluent of 0~20% EtOAc/Pet. ether gradient to give 3-fluoro-2-vinylphenol (Int C1). $^1H$ NMR (500 MHz, $CDCl_3$) δ 7.27 (dt, J=6.5, 8.2 Hz, 1H), 7.00 (dd, J=11.9, 18.2 Hz, 1H), 6.88-6.80 (m, 2H), 6.20-6.10 (m, 2H), 5.80 (dd, J=1.0, 11.8 Hz, 1H).

Preparation of Int D5: 5-chloro-6-methyl-1-(tetrahydro-2H-pyran-2-yl)-4-vinyl-1H-indazole

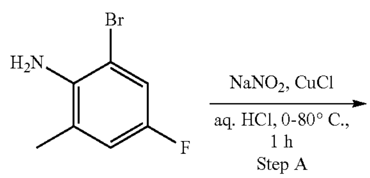

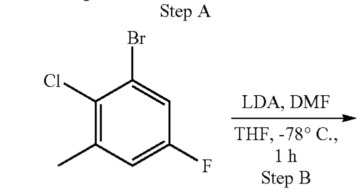

Int D1

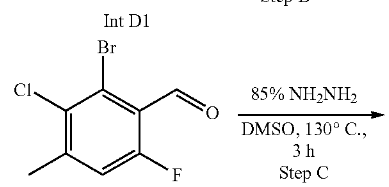

Int D2

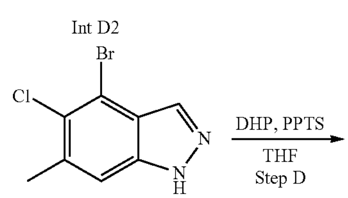

Int D3

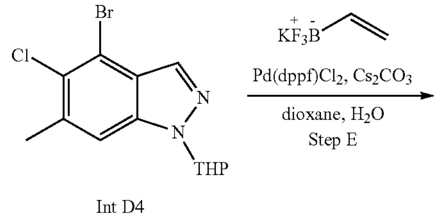

Int D4

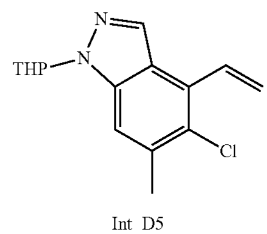

Int D5

Step A:
1-Bromo-2-chloro-5-fluoro-3-methylbenzene (Int D1)

2-Bromo-4-fluoro-6-methylaniline (18 g, 88 mmol) was added to a solution of water (108 mL) and conc. HCl (108 mL), and the resulting mixture was stirred at 70° C. for 1 h. The mixture was cooled to 0-5° C., a solution of sodium nitrite (9.13 g, 132 mmol) in water (18 mL) was added, and the mixture was stirred at this temperature for 15 min. The mixture was added into a solution of copper(I) chloride (13.10 g, 132 mmol) in conc. HCl (180 mL), and stirred at 70-80° C. for 30 min. The crude reaction mixture was cooled to room temperature, and extracted with DCM (100 mL×3). The combined organic layer was dried over sodium sulfate, filtered and concentrated in vacuo. The residue was purified by flash silica gel chromatography with an eluent of pure Pet. ether gradient to give 1-bromo-2-chloro-5-fluoro-3-methylbenzene (Int D1) $^1$H NMR (500 MHz, $CDCl_3$) δ 7.25 (br dd, J=1.8, 5.2 Hz, 1H), 6.96 (br dd, J=2.1, 5.8 Hz, 1H), 2.46 (s, 3H).

Step B:
2-Bromo-3-chloro-6-fluoro-4-methylbenzaldehyde (Int D2)

To a stirred solution of 1-bromo-2-chloro-5-fluoro-3-methylbenzene (Int D1) (19.3 g, 86 mmol) in THF (190 mL) was added LDA (51.8 mL, 104 mmol, 2 M in THF) at −78° C., and the mixture was stirred at −78° C. for 30 min, and then DMF (13.37 mL, 173 mmol) was added. The resulting mixture was stirred at −78° C. for 1 h. TLC showed the starting material was consumed. The reaction mixture was poured into aqueous NH4C1 (100 mL), and extracted with EtOAc (100 mL×3). The combined organic layer was dried over sodium sulfate, filtered and concentrated in vacuo. The residue was purified by flash silica gel chromatography with an eluent of 0~10% EtOAc/Pet. ether gradient to give 2-bromo-3-chloro-6-fluoro-4-methylbenzaldehyde (Int D2) $^1$H NMR (500 MHz, $CDCl_3$) δ 10.45 (s, 1H), 7.25 (d, J=10.7 Hz, 1H), 2.68 (s, 3H).

Step C: 4-Bromo-5-chloro-6-methyl-1H-indazole (Int D3)

To a mixture of 2-bromo-3-chloro-6-fluoro-4-methylbenzaldehyde (Int D2) (13.4 g, 53.3 mmol) in DMSO (200 mL) was added hydrazine (23.61 mL, 639 mmol) (85% in water), and the mixture was stirred at 130° C. for 3 h. The reaction mixture was quenched with water (300 mL), and extracted with EtOAc (200 mL×3). The combined organic layer was washed with brine (100 mL), dried over sodium sulfate, filtered and concentrated in vacuo. The residue was purified by flash silica gel chromatography with an eluent of 0~20% EtOAc/Pet. ether gradient to give 4-bromo-5-chloro-6-methyl-1H-indazole (Int D3) MS (ESI): m/z $(M+H)^+$ 244.7, 246.7

Step D: 4-Bromo-5-chloro-6-methyl-1-(tetrahydro-2H-pyran-2-yl)-1H-indazole (Int D4)

To a solution of 4-bromo-5-chloro-6-methyl-1H-indazole (Int D3) (9.3 g, 37.9 mmol) and PPTS (0.952 g, 3.79 mmol) in DCM (100 mL) was added 3,4-dihydro-2H-pyran (9.56 g, 114 mmol), and the mixture was stirred at 25° C. for 16 h. The reaction mixture was diluted with water (30 mL) and extracted with DCM (30 mL×3). The combined organic layer was dried over sodium sulfate, filtered and concentrated in vacuo. The residue was purified by flash silica gel chromatography with an eluent of 0~10% EtOAc/Pet. ether gradient to give 4-bromo-5-chloro-6-methyl-1-(tetrahydro-2H-pyran-2-yl)-1H-indazole (Int D4) MS (ESI): m/z $(M+H)^+$ 328.9, 330.9 (M+H) $^1$H NMR (400 MHz, $CDCl_3$) δ 7.94 (s, 1H), 7.43 (s, 1H), 5.66 (dd, J=2.7, 9.0 Hz, 1H), 4.04-3.96 (m, 1H), 3.79-3.70 (m, 1H), 2.57 (d, J=0.8 Hz, 3H), 2.55-2.47 (m, 1H), 2.21-2.12 (m, 1H), 2.11-2.03 (m, 1H), 1.83-1.66 (m, 3H).

Step E: 5-chloro-6-methyl-1-(tetrahydro-2H-pyran-2-yl)-4-vinyl-1H-indazole (Int D5)

To a solution of 4-bromo-5-chloro-6-methyl-1-(tetrahydro-2H-pyran-2-yl)-1H-indazole (Int D4) (4.0 g, 12.14 mmol) in 1,4-dioxane (32 mL) and water (8 mL) was added $Cs_2CO_3$ (11.86 g, 36.4 mmol), potassium trifluoro(vinyl) borate (2.438 g, 18.20 mmol) and [1,1'-bis(diphenylphosphino)ferrocene]dichloropalladium (II) (0.888 g, 1.214 mmol) at 25° C. under $N_2$ atmosphere. The mixture was stirred at 90° C. for 3 h. The mixture was cooled, filtered and the solvent was diluted with water (30 mL), extracted with EtOAc (3×40 mL), washed with brine (2×50 mL), dried over $Na_2SO_4$, filtered and the solvent was evaporated under reduced pressure to give the crude product. The crude product was purified by flash silica gel chromatography with an eluent of 0~10% petroleum ether/ethyl acetate gradient to give 5-chloro-6-methyl-1-(tetrahydro-2H-pyran-2-yl)-4-vinyl-1H-indazole (Int D5). MS (ESI): m/z $(M+H)^+$ 277. $^1$H NMR (400 MHz, $CDCl_3$) δ 8.13 (d, J=0.8 Hz, 1H), 7.40 (s, 1H), 7.22 (dd, J=11.3, 18.0 Hz, 1H), 5.90 (dd, J=1.4, 17.8 Hz, 1H), 5.71-5.65 (m, 2H), 4.06-3.99 (m, 1H), 3.79-3.71 (m, 1H), 2.52 (s, 3H), 2.21-2.13 (m, 1H), 2.11-2.04 (m, 1H), 1.83-1.72 (m, 3H), 1.70-1.64 (m, 1H).

Preparation of Int E1: 1-fluoro-5-vinylnaphthalene

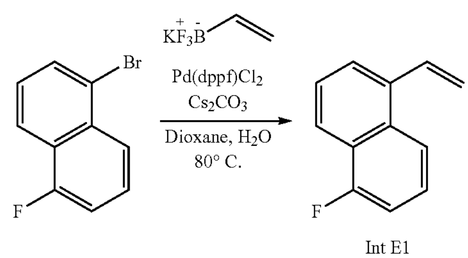

Int E1

1-Fluoro-5-vinylnaphthalene (Int E1)

To a solution of 1-bromo-5-fluoronaphthalene (1 g, 4.44 mmol), potassium vinyltrifluoroborate (0.714 g, 5.33 mmol) and cesium carbonate (2.90 g, 8.89 mmol) in dioxane (10 mL) and water (2 mL) was added $PdCl_2$ (dppf) (0.163 g, 0.222 mmol) at room temperature (20° C.) under $N_2$ atmosphere. The mixture was stirred at 80° C. for 15 h. The mixture was cooled, diluted with water (5 mL), extracted with EtOAc (10 mL), dried over $Na_2SO_4$, filtered and the solvent was evaporated under reduced pressure. The residue was purified by flash silica gel chromatography with an eluent of 100% Pet.ether gradient to give 1-fluoro-5-vinylnaphthalene (Int E1). $^1$H NMR (500 MHz, $CDCl_3$) δ=7.90 (d, J=8.4 Hz, 1H), 7.71 (d, J=8.7 Hz, 1H), 7.49 (d, J=7.2 Hz, 1H), 7.40-7.19 (m, 3H), 6.98 (dd, J=8.0, 10.1 Hz, 1H), 5.62 (dd, J=1.4, 17.2 Hz, 1H), 5.32 (dd, J=1.3, 10.9 Hz, 1H).

Preparation of Int F1: 1-(prop-1-en-2-yl)naphthalene

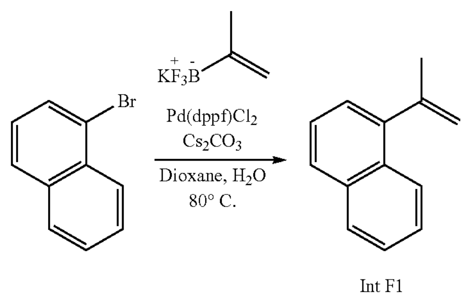

Int F1

1-(prop-1-en-2-yl)naphthalene (Int F1)

To a mixture of 1-bromonaphthalene (8 g, 38.6 mmol) in dioxane (80 mL) and water (15 mL) was added 4,4,5,5-tetramethyl-2-(prop-1-en-2-yl)-1,3,2-dioxaborolane (9.74 g, 58.0 mmol), [1,1'-bis(diphenylphosphino)ferrocene]dichloropalladium(II) (2.83 g, 3.86 mmol) and $Cs_2CO_3$ (25.2 g, 77 mmol), and the mixture was stirred at 80° C. for 15 h. The mixture was evaporated under reduced pressure to give the crude product. The crude product was purified by flash silica gel chromatography with an eluent of Pet. ether gradient to give 1-(prop-1-en-2-yl)naphthalene (Int F1). $^1$H NMR (400 MHz, Methanol-$d_4$) δ=8.02-7.98 (m, 1H), 7.88-7.79 (m, 2H), 7.47-7.43 (m, 3H), 7.28 (d, J=6.3 Hz, 1H), 5.41 (s, 1H), 5.42-5.39 (m, 1H), 4.99 (d, J=0.8 Hz, 1H), 2.18 (s, 3H).

Preparation of Int G1: 1-(2,2-difluorovinyl)naphthalene

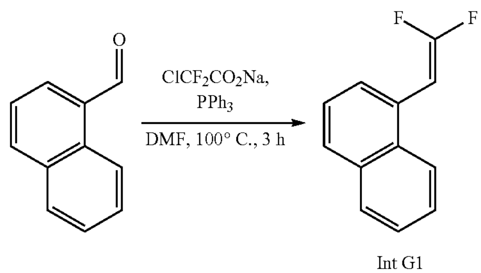 [SMILES: O=Cc1cccc2ccccc12 ; FC(F)=Cc1cccc2ccccc12]

Int G1

1-(2,2-Difluorovinyl)naphthalene (Int G1)

To a three-necked round-bottom flask equipped with a magnetic stir bar and charged with 1-naphthaldehyde (12.5 g, 80 mmol), triphenylphosphine (25.2 g, 96 mmol) in DMF (164 mL) was added a solution of sodium 2-chloro-2,2-difluoroacetate (18.30 g, 120 mmol) in DMF (25 mL) dropwisely at 100° C. over 30 min. After the addition was completed, the reaction mixture was heated additionally at the same temperature for 10 h. After cooling to 0° C., to the reaction mixture was added water (150 mL) and extracted with ethyl acetate (2×160 mL). The combined organic layers were washed with brine (150 mL), dried over $Na_2SO_4$, filtered and the solvent was evaporated under reduced pressure. The residue was purified by silica-gel column chromatography with an eluent of Pet. ether) to give 1-(2,2-difluorovinyl)naphthalene (Int G1). $^1$H NMR (400 MHz, $CDCl_3$) δ 7.96 (d, J=7.6 Hz, 1H), 7.87 (d, J=7.2 Hz, 1H), 7.80 (d, J=8.1 Hz, 1H), 7.64-7.44 (m, 4H), 5.85 (dd, J=24.4, 3.2 Hz, 1H).

Preparation of Int H4: 6-(Methoxymethoxy)-1-vinylnaphthalene

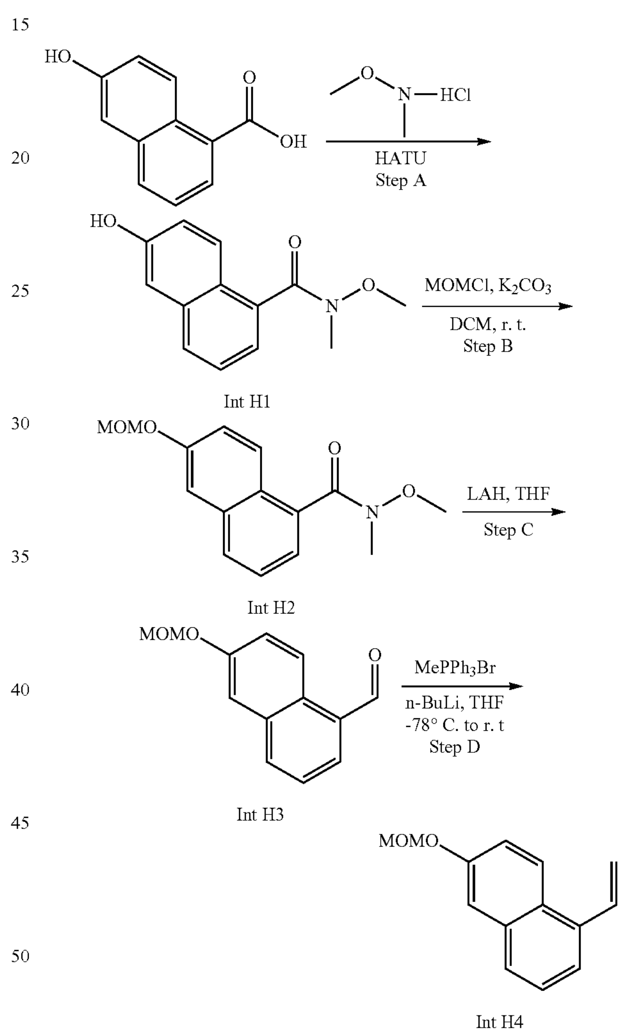

Int H4

Step A: 6-Hydroxy-N-methoxy-N-methyl-1-naphthamide (Int H1)

A solution of 6-hydroxy-1-naphthoic acid (15 g, 80 mmol), N,O-dimethylhydroxylamine hydrochloride (9.33 g, 96.0 mmol), DMA (41.8 mL, 239 mmol) and HATU (45.5 g, 120 mmol) in DMF (150 mL) was prepared. The mixture was stirred at 20° C. for 8 h. The reaction mixture was quenched with water (100 mL), and extracted with ethyl acetate (3×150 mL). The combined organic layers were washed with brine (50 mL), dried over $Na_2SO_4$, filtered and the solvent was evaporated under reduced pressure. The residue was purified by column chromatography on silica gel (petroleum ether:ethyl acetate=2:1 to 1:1) to give 6-hydroxy-N-methoxy-N-methyl-1-naphthamide (Int H1). MS (ESI): m/z $[M+H]^+$ 232.

Step B: N-Methoxy-6-(methoxymethoxy)-N-methyl-1-naphthamide (Int H2)

To a solution of 6-hydroxy-N-methoxy-N-methyl-1-naphthamide (Int H1) (6.00 g, 25.9 mmol) in acetone (70 mL) was added $K_2CO_3$ (7.17 g, 51.9 mmol) and chloro(methoxy)methane (2.37 mL, 31.1 mmol) at 25° C. The mixture was stirred at 15° C. for 8 h. The mixture was diluted with water (100 mL), extracted with EtOAc (3×150 mL), dried over $Na_2SO_4$, filtered and the solvent was evaporated under reduced pressure to give the crude product. The residue was purified by column chromatography on silica gel (Pet. ether:ethyl acetate=1:1) to give N-methoxy-6-(methoxymethoxy)-N-methyl-1-naphthamide (Int H2). MS (ESI): m/z $[M+H]^+$ 276.

Step C: 6-(Methoxymethoxy)-1-naphthaldehyde (Int H3)

To a solution of N-methoxy-6-(methoxymethoxy)-N-methyl-1-naphthamide (Int H2) (1.00 g, 3.63 mmol) in THF (10 mL) was added lithium aluminum hydride (0.414 g, 10.9 mmol) at 0° C. under $N_2$ protection. The reaction mixture stirred at 0° C. for 2 h. The reaction mixture was quenched with 3 mL of $H_2O$ and 3 mL of NaOH (10%) at 0° C. in sequence. Then $Na_2SO_4$ and $MgSO_4$ were added. The mixture was filtered and the filtrate was concentrated under reduced pressure to give the residue, which was purified by chromatography on silica gel (EtOAc:Pet. ether, 1:10 to 1:5) to give 6-(methoxymethoxy)-1-naphthaldehyde (Int H3). $^1H$ NMR (400 MHz, $CDCl_3$) δ 10.32 (s, 1H), 9.19 (d, J=9.3 Hz, 1H), 7.99 (d, J=8.1 Hz, 1H), 7.84 (dd, J=1.2, 7.1 Hz, 1H), 7.58 (dd, J=7.2, 8.2 Hz, 1H), 7.48-7.36 (m, 2H), 5.35-5.27 (m, 2H), 3.51 (s, 3H).

Step D: 6-(Methoxymethoxy)-1-vinylnaphthalene (Int H4)

Methyltriphenylphosphonium bromide (2.31 g, 6.47 mmol) was suspended in dry THF (10 mL) at −78° C. n-BuLi (2.59 mL, 6.47 mmol, 2.5 M in hexane) was added to the suspension, and a bright yellow color was observed. The mixture was stirred at −78° C. for 30 min. 6-(methoxymethoxy)-1-naphthaldehyde (Int H3) (700 mg, 3.24 mmol) in THF (2 mL) was added, and the reaction mixture was stirred at 25° C. for 2 h. The mixture was quenched by 20 mL of saturated $NH_4Cl$. The solvent was removed under reduced pressure, and the residue was dissolved in water (50 mL) and EtOAc (30 mL). The organic layer was separated and the aqueous layer was re-extracted with EtOAc (3×50 mL), and the combined organic layers were washed with brine (50 mL), dried over anhydrous $Na_2SO_4$, filtered and concentrated under reduced pressure. The residue was purified by chromatography on silica gel (EtOAc:Pet. ether=1:10 to 1:5) to give 6-(methoxymethoxy)-1-vinylnaphthalene (Int H4). $^1H$ NMR (400 MHz, $CDCl_3$) δ 8.04 (d, J=9.0 Hz, 1H), 7.67 (d, J=8.3 Hz, 1H), 7.51-7.37 (m, 4H), 7.25-7.20 (m, 1H), 5.76 (dd, J=1.5, 17.4 Hz, 1H), 5.48-5.40 (m, 1H), 5.29 (s, 2H), 3.51 (s, 3H).

Preparation of Int I1: 1-(prop-1-en-1-yl)naphthalene

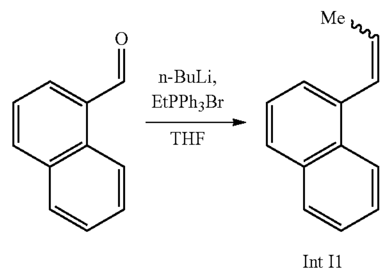

Int I1

1-(Prop-1-en-1-yl)naphthalene (Int I1)

Ethyltriphenylphosphonium bromide (17.83 g, 48.0 mmol) was suspended in dry THF (500 mL) at −78° C. n-BuLi (19.21 mL, 48.0 mmol, 2.5 M in n-hexane) was added to the suspension. The mixture was stirred at −78° C. for 30 min. 1-Naphthaldehyde (5 g, 32.0 mmol) was added, and the reaction mixture was stirred at 25° C. for 16 h. The mixture was quenched by 100 mL of saturated $NH_4Cl$. The solvent was removed under reduced pressure, and the residue was dissolved in water (200 mL) and EtOAc (200 mL). The organic layer was separated, and the aqueous layer was re-extracted with EtOAc (200 mL×3), and the combined organic layers were washed with brine (600 mL), dried over anhydrous $Na_2SO_4$, filtered and concentrated under reduced pressure. The residue was chromatographed on silica gel (EtOAc/Pet. ether, 0:100 to 5:95) to give 1-(prop-1-en-1-yl)naphthalene (Int I1) as a 10:1 mixture of cis:trans isomers. $^1H$ NMR (400 MHz, CHLOROFORM-d) δ 8.19-7.96 (m, 1H), 7.91-7.82 (m, 1H), 7.78 (d, J=8.2 Hz, 1H), 7.59-7.42 (m, 3H), 7.38 (d, J=7.0 Hz, 1H), 7.19-6.87 (m, 1H), 6.33-6.01 (m, 1H), 2.05-1.74 (m, 3H).

Preparation of Int J2: (E)-1-(prop-1-en-1-yl)naphthalene

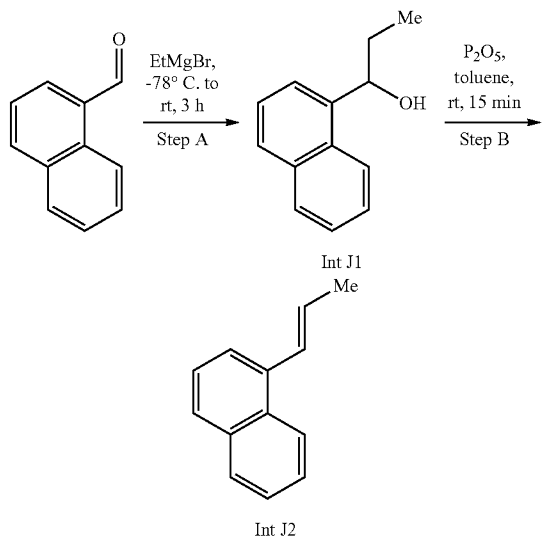

Int J1

Int J2

Step A: 1-(naphthalen-1-yl)propan-1-ol (Int. J1)

To a solution of 1-naphthaldehyde (5 g, 32.0 mmol) in THF (50 mL) was added ethylmagnesium bromide (2.5 M in THF) (38.4 mL, 96 mmol) at −78° C. under $N_2$ atmosphere. The mixture was stirred at −78° C. for 1 h. The mixture was cooled, diluted with saturated aqueous $NH_4Cl$ (20 mL), extracted with ethyl acetate (25×3 mL), dried over $Na_2SO_4$, filtered and the solvent was evaporated under reduced pressure to give crude 1-(naphthalen-1-yl)propan-1-ol (Int J1) as only the trans isomer. $^1H$ NMR (400 MHz, Methanol-d4) δ 7.90 (d, J=8.0 Hz, 1H), 7.68-7.65 (m, 1H), 7.56 (d, J=8.0 Hz, 1H), 7.42 (d, J=7.2 Hz, 1H), 7.31-7.24 (m, 3H), 5.18 (dd, J=5.2, 7.5 Hz, 1H), 1.86-1.75 (m, 2H), 0.82 (t, J=7.2 Hz, 3H).

Step B: (E)-1-(prop-1-en-1-yl)naphthalene (Int J2)

To a solution of 1-(naphthalen-1-yl)propan-1-ol (Int. J1) (5 g, 26.8 mmol) in toluene (40 mL) was added phosphorus pentoxide (3.81 g, 26.8 mmol) at 0° C. The mixture was stirred at 0° C. for 0.5 h. The mixture was cooled, diluted with saturated aqueous $NaHCO_3$ (15 mL), extracted with Pet. ether (20×3 mL), dried over $Na_2SO_4$, filtered and the solvent was evaporated under reduced pressure to give the crude product. The crude product was purified by flash silica gel chromatography with an eluent of 0-30% EtOAc/Pet. ether gradient to give (E)-1-(prop-1-en-1-yl)naphthalene (Int J2). $^1H$ NMR (400 MHz, Methanol-$d_4$) δ 8.18-8.07 (m, 1H), 7.87-7.80 (m, 1H), 7.72 (d, J=8.0 Hz, 1H), 7.54-7.40 (m, 4H), 7.20-7.13 (m, 1H), 6.24 (qd, J=6.4, 15.4 Hz, 1H), 1.99 (dd, J=1.6, 6.6 Hz, 3H).

Int K5: 3-(Tetrahydro-2H-pyran-2-yl)-9-vinyl-3H-benzo[e]indazole

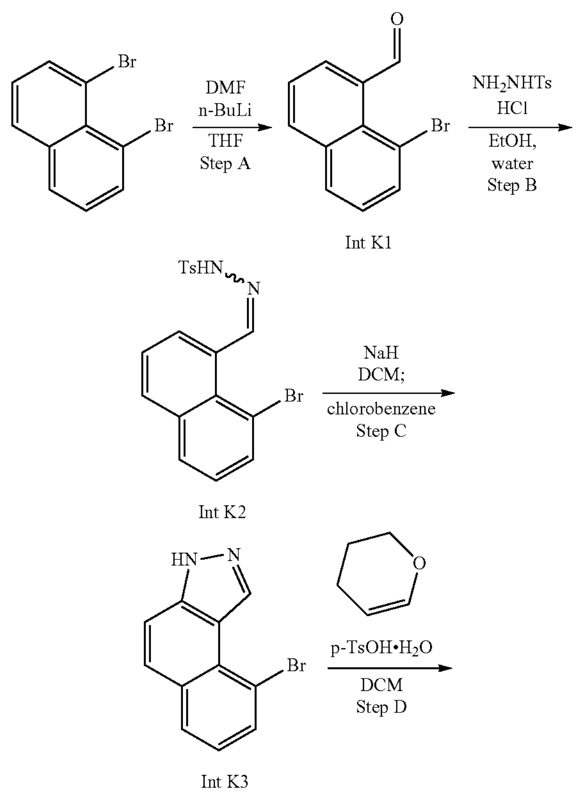

Int K1

Int K2

Int K3

-continued

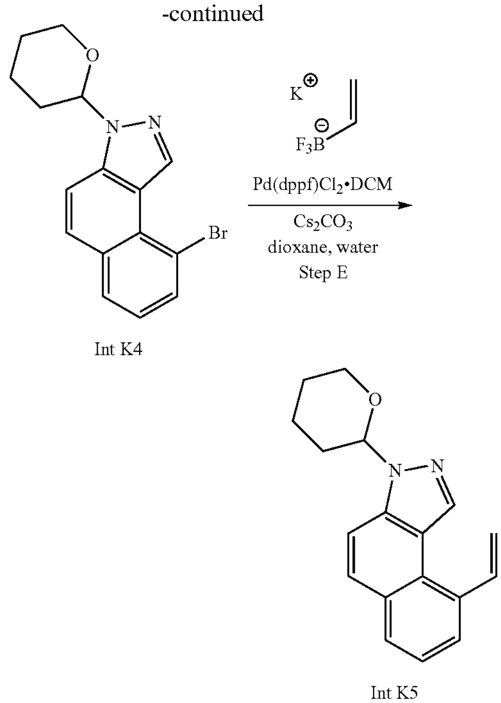

Int K4

Int K5

Step A: 8-Bromo-1-naphthaldehyde (Int K1)

n-BuLi (1.6 M in hexanes, 19.5 mL, 31.2 mmol) was added to a solution of 1,8-dibromonaphthalene (5.95 g, 20.8 mmol) in degassed THF (63.1 mL) at −78° C. The reaction stirred vigorously at −78° C. for 15 min, at which point, DMF (2.90 mL, 37.5 mmol) was added. The reaction stirred vigorously at −78° C. for 1 hour. The reaction was diluted with sat. aq. $NH_4Cl$ (15 mL) and water (15 mL), and extracted with DCM (3×25 mL). The combined organic layers were dried over anhydrous $MgSO_4$, filtered, and concentrated under reduced pressure. The crude residue was purified by silica gel chromatography (gradient elution: 0-10% EtOAc/hexanes) to provide 8-bromo-1-naphthaldehyde (Int K1). MS (ESI) $[M+H]^+$ m/z: 235; $^1H$ NMR (600 MHz, $CDCl_3$) δ 11.44 (s, 1H), 8.04-7.98 (m, 1H), 7.97-7.84 (m, 3H), 7.57 (t, J=7.6 Hz, 1H), 7.39 (t, J=7.8 Hz, 1H).

Step B: N-((8-Bromonaphthalen-1-yl)methylene)-4-methylbenzenesulfonohydrazide (Int K2)

HCl (37%, 57 μL, 0.69 mmol) was added to a solution of 8-bromo-1-naphthaldehyde (Int K1) (3.28 g, 13.9 mmol) and $NH_2NHTs$ (2.65 g, 14.2 mmol) in EtOH (19.8 mL) and water (1.04 mL) at 75° C. The reaction stirred vigorously at 75° C. for 5 min. The reaction was cooled to room temperature, filtered, and washed with EtOH (5×10 mL). The resulting solid was dried under reduced pressure to provide N-((8-bromonaphthalen-1-yl)methylene)-4-methylbenzenesulfonohydrazide (Int K2), which was used in the subsequent step without further purification. MS (ESI) $[M+H]^+$ m/z: 403.

Step C: 9-Bromo-3H-benzo[e]indazole (Int K3)

NaH (60 wt % in mineral oil, 588 mg, 14.7 mmol) was added to a suspension of N-((8-bromonaphthalen-1-yl)methylene)-4-methylbenzenesulfonohydrazide (Int K2) (5.39 g, 13.4 mmol) in DCM (44.6 mL). The reaction stirred vigorously at room temperature for 30 min. The reaction was concentrated under reduced pressure. The concentrated mixture was re-suspended in chlorobenzene (44.6 mL) and stirred vigorously at 120° C. for 30 min. The reaction was cooled to room temperature, filtered, and washed with chlorobenzene (3×10 mL). The resulting solid was dried under reduced pressure to provide 9-bromo-3H-benzo[e]indazole (Int K3), which was used in the subsequent step without further purification. MS (ESI) $[M+H]^+$ m/z: 247.

Step D: 9-Bromo-3-(tetrahydro-2H-pyran-2-yl)-3H-benzo[e]indazole (Int K4)

p-TsOH·$H_2O$ (636 mg. 3.34 mmol) was added to a suspension of 9-bromo-3H-benzo[e]indazole (Int K3) (3.31 g, 13.4 mmol) and 3,4-dihydro-2H-pyran (3.66 mL, 40.1 mmol) in DCM (53.5 mL). The reaction stirred vigorously at 50° C. for 21 h. The reaction was cooled to room temperature, diluted with sat. aq. $NaHCO_3$ (25 mL) and extracted with DCM (3×50 mL). The combined organic layers were dried over anhydrous $MgSO_4$, filtered, and concentrated under reduced pressure. The crude residue was purified by silica gel chromatography (gradient elution: 0-50% EtOAc/Hexanes) to provide 9-bromo-3-(tetrahydro-2H-pyran-2-yl)-3H-benzo[e]indazole (Int K4). MS (ESI) $[M+H]^+$ m/z: 331.

Step E: 3-(Tetrahydro-2H-pyran-2-yl)-9-vinyl-3H-benzo[e]indazole (Int K5)

Potassium vinyltrifluoroborate (1.72 g, 12.9 mmol), $Cs_2CO_3$ (5.59 g, 17.2 mmol), and $PdCl_2(dppf)·CH_2Cl_2$ (0.350 g, 0.429 mmol) were combined. The reaction vessel was sealed and flushed with nitrogen for 5 min, evacuated for 1 min, and backfilled with nitrogen for 1 min. A degassed solution of 9-bromo-3-(tetrahydro-2H-pyran-2-yl)-3H-benzo[e]indazole (Int K4) (2.84 g, 8.58 mmol) in dioxane (13.7 mL) and water (3.43 mL) was added, and the reaction was degassed by sparging with nitrogen for an additional 5 min, then backfilled with nitrogen for 1 min. The reaction stirred vigorously at 100° C. for 16 h. The reaction was cooled to room temperature, diluted with water (25 mL), and extracted with EtOAc (3×25 mL). The combined organic layers were dried over anhydrous $MgSO_4$, filtered, and concentrated under reduced pressure. The crude residue was purified by silica gel chromatography (gradient elution: 0-50% EtOAc/Hexanes) to provide 3-(tetrahydro-2H-pyran-2-yl)-9-vinyl-3H-benzo[e]indazole (Int K5). MS (ESI) $[M+H]^+$ m/z: 279.

Example 1a/b: 2-((2S)-1-acryloyl-4-(2-4(S)-1-methylpyrrolidin-2-yl)methoxy)-7-(naphthalen-1-yl)-6,7-dihydro-5H-pyrano[2,3-d]pyrimidin-4-yl)piperazin-2-yl)acetonitrile

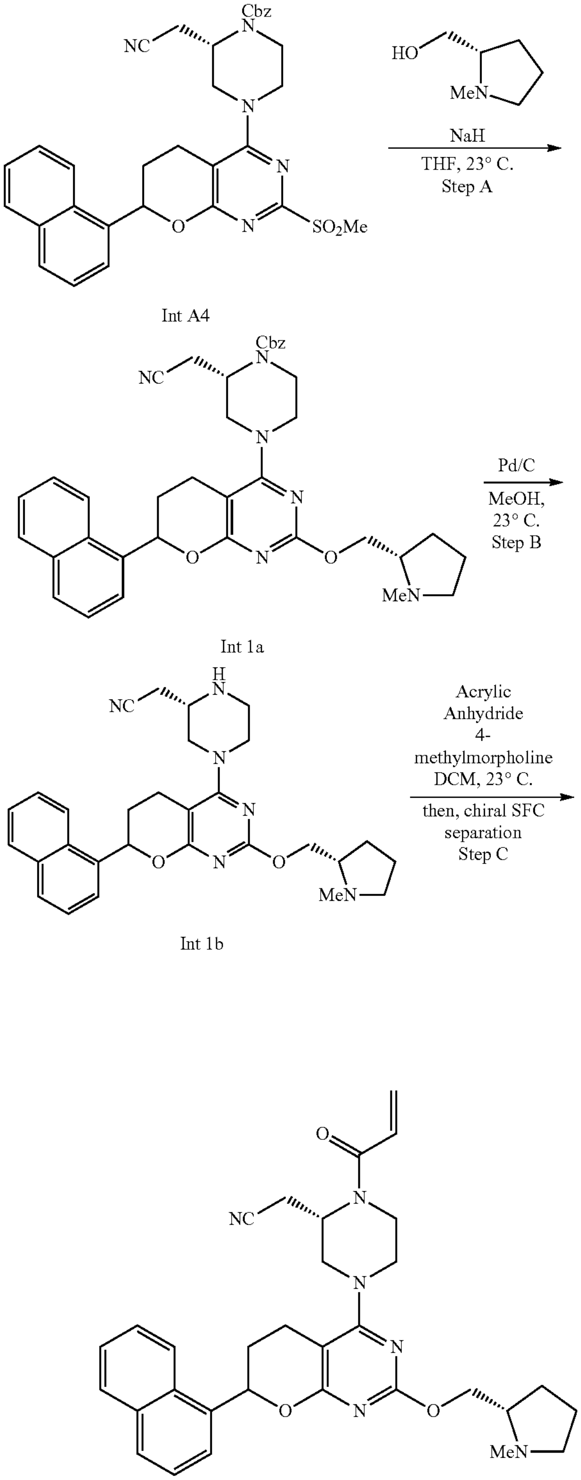

Ex. 1a
Ex. 1b

Step A: benzyl (2S)-2-(cyanomethyl)-4-(2-(((S)-1-methylpyrrolidin-2-yl)methoxy)-7-(naphthalen-1-yl)-6,7-dihydro-5H-pyrano[2,3-d]pyrimidin-4-yl)piperazine-1-carboxylate (Int 1a)

Benzyl (2S)-2-(cyanomethyl)-4-(2-(methylsulfonyl)-7-(naphthalen-1-yl)-6,7-dihydro-5H-pyrano[2,3-d]pyrimidin-4-yl)piperazine-1-carboxylate (Int A4) (244 mg, 0.408 mmol), sodium hydride (49.0 mg, 1.23 mmol, 60% dispersion in mineral oil), and (5)-(1-methylpyrrolidin-2-yl) methanol (146 μL, 1.23 mmol) were combined in THF (2.1 mL). The reaction was stirred for 15 minutes. The reaction was carefully quenched with methanol and concentrated. The residual oil was loaded directly onto a 24 g silica gel column, eluting from 0-20% MeOH in DCM to yield benzyl (2S)-2-(cyanomethyl)-4-(2-(((S)-1-methylpyrrolidin-2-yl) methoxy)-7-(naphthalen-1-yl)-6,7-dihydro-5H-pyrano[2,3-d]pyrimidin-4-yl)piperazine-1-carboxylate (Int 1a). MS (ESI) $[M+H]^+$ m/z: 633.

Step B: 2-((2S)-4-(2-(((S)-1-methylpyrrolidin-2-yl) methoxy)-7-(naphthalen-1-yl)-6,7-dihydro-5H-pyrano[2,3-d]pyrimidin-4-yl)piperazin-2-yl)acetonitrile (Int 1b)

An 8 mL vial was charged with Pd/C (10 wt. % loading, 15 mg, 0.014 mmol) and benzyl (2S)-2-(cyanomethyl)-4-(2-(((S)-1-methylpyrrolidin-2-yl)methoxy)-7-(naphthalen-1-yl)-6,7-dihydro-5H-pyrano[2,3-d]pyrimidin-4-yl)piperazine-1-carboxylate (Int 1a) (89 mg, 0.14 mmol) in MeOH (890 μL) was added under nitrogen. The reaction mixture was degassified with vacuum and back filled with nitrogen thrice and stirred under hydrogen balloon at room temperature for 4 hrs. The reaction mixture was filtered over Celite and the filtrate was concentrated to yield 2-((2S)-4-(2-(((S)-1-methylpyrrolidin-2-yl)methoxy)-7-(naphthalen-1-yl)-6,7-dihydro-5H-pyrano[2,3-d]pyrimidin-4-yl)piperazin-2-yl)acetonitrile (Int 1b). MS (ESI): $[M+H]^+$ m/z: 499.

Step C: 2-((2S)-1-acryloyl-4-(2-(((S)-1-methylpyrrolidin-2-yl)methoxy)-7-(naphthalen-1-yl)-6,7-dihydro-5H-pyrano[2,3-d]pyrimidin-4-yl)piperazin-2-yl)acetonitrile (Ex. 1a/b)

To a solution of 2-((2S)-4-(2-(((S)-1-methylpyrrolidin-2-yl)methoxy)-7-(naphthalen-1-yl)-6,7-dihydro-5H-pyrano[2,3-d]pyrimidin-4-yl)piperazin-2-yl)acetonitrile (Int 1b) (63 mg, 0.13 mmol) in DCM (1.2 mL) was added 4-methylmorpholine (42 μL, 0.38 mmol)) and acrylic anhydride (17 μL, 0.15 mmol) under nitrogen. The reaction mixture was stirred at room temperature for 30 minutes. The reaction mixture was then diluted with DCM, washed with brine solution and concentrated. The crude material was purified by 24 g silica gel column with 20% of methanol in DCM to yield racemic product. The racemic material was resolved by SFC (Column A; $CH_3CN$/MeOH and 45% MeOH (with 0.1% $NH_4OH$)) to provide 2-((2S)-1-acryloyl-4-(2-(((S)-1-methylpyrrolidin-2-yl)methoxy)-7-(naphthalen-1-yl)-6,7-dihydro-5H-pyrano[2,3-d]pyrimidin-4-yl)piperazin-2-yl)acetonitrile; Peak 1 (Ex. 1a). MS (ESI): $[M+H]^+$ m/z: 553. $^1$H NMR (499 MHz, DMSO-$d_6$) δ 8.17 (d, J=8.1 Hz, 1H), 8.07-7.92 (m, 2H), 7.66 (d, J=7.0 Hz, 1H), 7.65-7.54 (m, 3H), 6.88 (s, 1H), 6.20 (dd, J=16.6, 2.2 Hz, 1H), 6.11 (d, J=9.6 Hz, 1H), 5.78 (dd, J=10.5, 2.0 Hz, 1H), 4.20 (dd, J=10.6, 5.0 Hz, 1H), 4.04 (dd, J=10.6, 6.3 Hz, 2H), 3.96-3.76 (m, 2H), 3.60 (d, J=22.0 Hz, 1H), 3.29-3.21 (m, 2H), 3.18 (s, 2H), 3.10-2.85 (m, 5H), 2.74 (d, J=55.5 Hz, 2H), 2.38 (d, J=13.3 Hz, 2H), 2.33 (s, 3H), 2.16 (q, J=8.8 Hz, 1H), 2.05-1.85 (m, 2H), 1.72-1.49 (m, 3H). And 2-((2S)-1-acryloyl-4-(2-(((S)-1-methylpyrrolidin-2-yl)methoxy)-7-(naphthalen-1-yl)-6,7-dihydro-5H-pyrano[2,3-d]pyrimidin-4-yl)piperazin-2-yl)acetonitrile; Peak 2 (Ex. 1b). MS (ESI): $[M+H]^+$ m/z: 553. $^1$H NMR (499 MHz, DMSO-$d_6$) δ 8.15 (d, J=8.2 Hz, 1H), 8.04-7.91 (m, 2H), 7.65-7.59 (m, 2H), 7.59-7.54 (m, 2H), 6.89 (s, 1H), 6.37-6.08 (m, 2H), 5.79 (d, J=11.6 Hz, 1H), 4.52 (dd, J=20.1, 12.8 Hz, 3H), 4.17-3.71 (m, 3H), 3.66 (d, J=40.2 Hz, 1H), 3.15-2.89 (m, 7H), 2.82 (s, 3H), 2.38 (d, J=13.8 Hz, 2H), 2.29-2.08 (m, 2H), 2.12-1.61 (m, 6H).

Example 2: 2-((2S)-1-acryloyl-4-(7-(8-methylnaphthalen-1-yl)-2-(((S)-1-methylpyrrolidin-2-yl) methoxy)-6,7-dihydro-5H-pyrano[2,3-d]pyrimidin-4-yl)piperazin-2-yl)acetonitrile

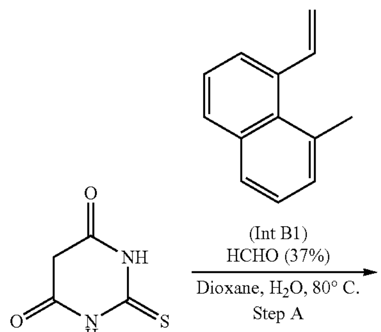

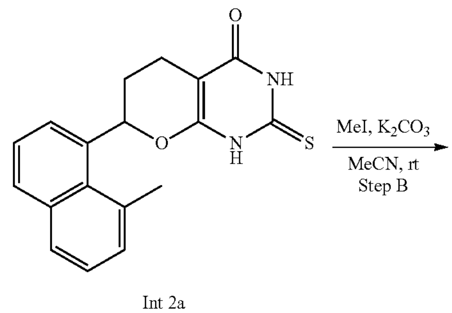

Int 2a

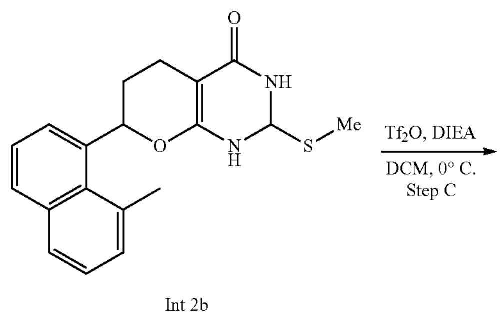

Int 2b

-continued

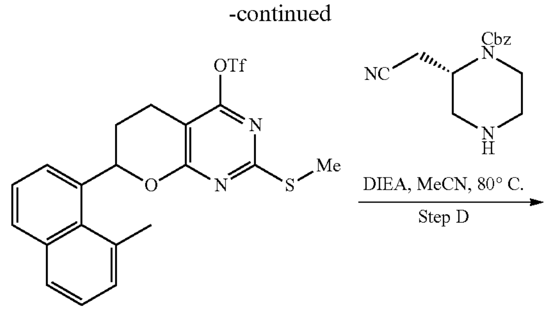

Int 2c

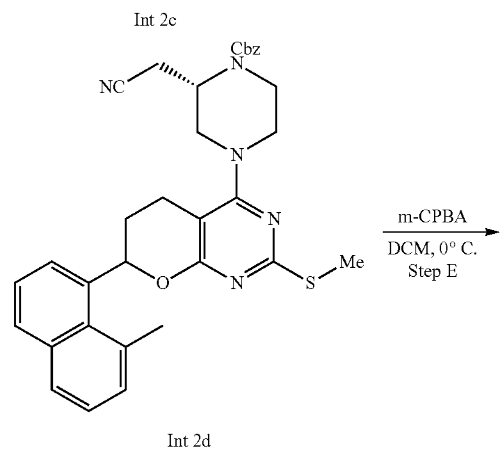

Int 2d

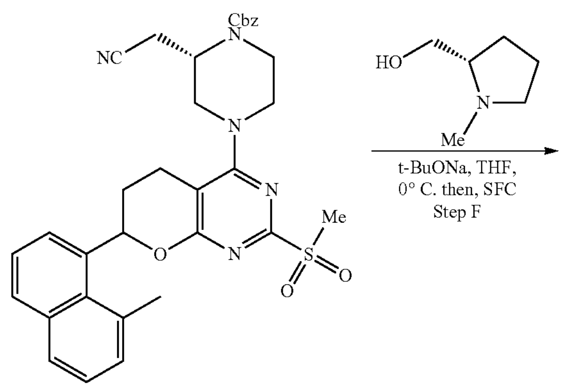

Int 2e

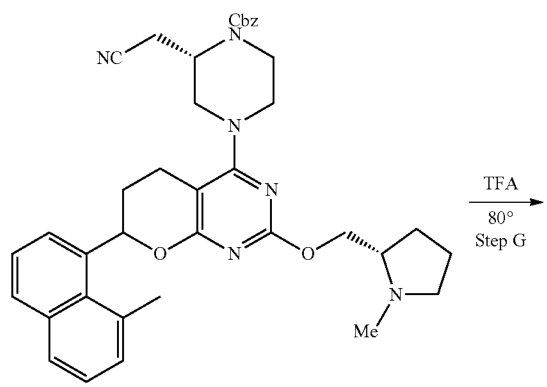

Int 2f

-continued

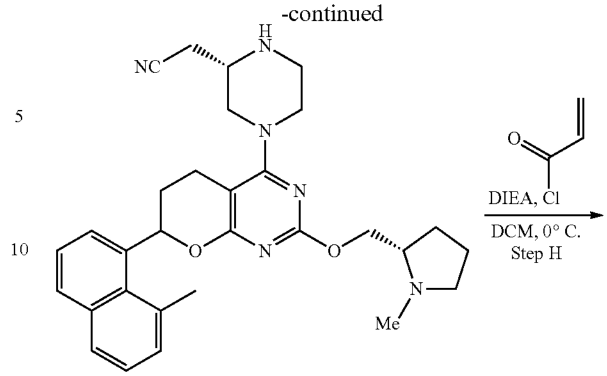

Int 2g

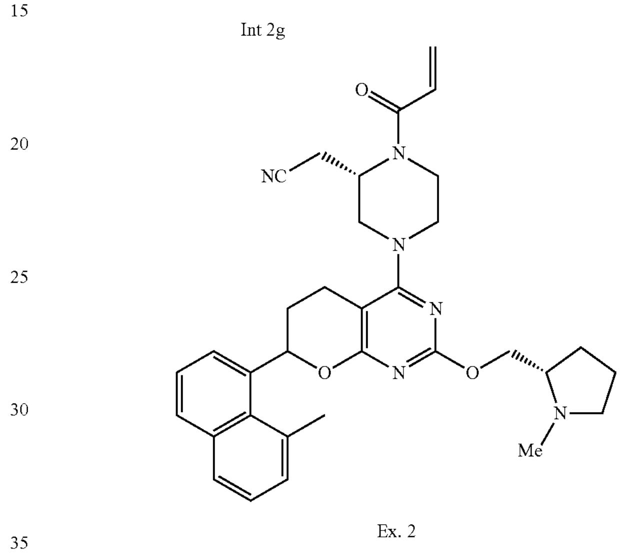

Ex. 2

Step A: 7-(8-methylnaphthalen-1-yl)-2-thioxo-1,2,3,5,6,7-hexahydro-4H-pyrano[2,3-d]pyrimidin-4-one (Int 2a)

To a solution of 1-methyl-8-vinylnaphthalene (Int B1) (1.0 g, 5.9 mmol) in water (5.0 mL) and MeCN (5.0 mL) was added 2-thioxodihydropyrimidine-4,6(1H,5H)-dione (1.29 g, 8.92 mmol) and formaldehyde (0.904 mL, 11. 9 mmol) (37% in water) at 25° C. The mixture was stirred at 80° C. for 2 h. The mixture was filtered and the solid was dried under reduced pressure to give 7-(8-methylnaphthalen-1-yl)-2-thioxo-1,2,3,5,6,7-hexahydro-4H-pyrano[2,3-d]pyrimidin-4-one (Int 2a) which was used directly in the next step without further purification. MS (ESI): m/z $[M+H]^+$ 325.

Step B: 7-(8-methylnaphthalen-1-yl)-2-(methylthio)-3,5,6,7-tetrahydro-4H-pyrano[2,3-d]pyrimidin-4-one (Int 2b)

To a solution of 7-(8-methylnaphthalen-1-yl)-2-thioxo-1,2,3,5,6,7-hexahydro-4H-pyrano[2,3-d]pyrimidin-4-one (Int 2a) (500 mg, 1.54 mmol) in acetonitrile (5.0 mL) was added $K_2CO_3$ (320 mg, 2.31 mmol). The mixture was stirred at 25° C. for 1 h under $N_2$ atmosphere. Then iodomethane (0.048 mL, 0.77 mmol) was added. The mixture was stirred at 25° C. for 1 h. From LCMS, the starting material was remained. Then iodomethane (0.048 mL, 0.77 mmol) was added. And the mixture was stirred at 25° C. for 30 min. The mixture was diluted with water (10 mL), extracted with DCM/

MeOH (10:1) (3×10 mL), dried over $Na_2SO_4$, filtered and the solvent was evaporated under reduced pressure to give crude 7-(8-methylnaphthalen-1-yl)-2-(methylthio)-3,5,6,7-tetrahydro-4H-pyrano[2,3-d]pyrimidin-4-one (Int 2b). MS (ESI): m/z $[M+H]^+$ 339.

Step C: 7-(8-methylnaphthalen-1-yl)-2-(methylthio)-6,7-dihydro-5H-pyrano[2,3-d]pyrimidin-4-yl tri fluoromethanesulfonate (Int 2c)

To a solution of 7-(8-methylnaphthalen-1-yl)-2-(methylthio)-3,5,6,7-tetrahydro-4H-pyrano[2,3-d]pyrimidin-4-one (Int 2b) (374 mg, 1.11 mmol) in DCM (4.0 mL) was added DIEA (0.579 mL, 3.32 mmol) at 25° C. The mixture was cooled to 0° C., then trifluoromethanesulfonic anhydride (0.279 mL, 1.66 mmol) was added. And the mixture was stirred at 25° C. for 30 min. LCMS showed the starting material was remained. Then trifluoromethanesulfonic anhydride (0.120 mL, 0.713 mmol) was added at 25° C. And then the mixture was stirred at 25° C. for 10 min. The mixture was evaporated under reduced pressure to give the crude product, which was purified by flash silica gel chromatography (eluent of 0~10% ethyl acetate/petroleum ether) to give 7-(8-methylnaphthalen-1-yl)-2-(methylthio)-6,7-dihydro-5H-pyrano[2,3-d]pyrimidin-4-yl trifluoromethanesulfonate (Int 2c). MS (ESI): m/z $[M+H]^+$ 471.

Step D: benzyl (2S)-2-(cyanomethyl)-4-(7-(8-methylnaphthalen-1-yl)-2-(methylthio)-6,7-dihydro-5H-pyrano[2,3-d]pyrimidin-4-yl)piperazine-1-carboxylate (Int 2d)

To a solution of 7-(8-methylnaphthalen-1-yl)-2-(methylthio)-6,7-dihydro-5H-pyrano[2,3-d]pyrimidin-4-yl trifluoromethanesulfonate (Int 2c) (150 mg, 0.319 mmol) in MeCN (2.0 mL) was add ed DIEA (0.167 mL, 0.956 mmol) and (S)-benzyl 2-(cyanomethyl)piperazine-1-carboxylate (174 mg, 0.671 mmol) at 25° C. under $N_2$ atmosphere. The mixture was stirred at 80° C. for 15 h. The mixture was cooled, evaporated under reduced pressure to give the crude product, which was purified by preparative TLC ($SiO_2$, petroleum ether:ethyl acetate=2:1) to give benzyl (2S)-2-(cyanomethyl)-4-(7-(8-methylnaphthalen-1-yl)-2-(methylthio)-6,7-dihydro-5H-pyrano[2,3-d]pyrimidin-4-yl)piperazine-1-carboxylate (Int 2d). MS (ESI): m/z $[M+H]^+$ 580.

Step E: benzyl (2S)-2-(cyanomethyl)-4-(7-(8-methylnaphthalen-1-yl)-2-(methylsulfinyl)-6,7-dihydro-5H-pyrano[2,3-d]pyrimidin-4-yl)piperazine-1-carboxylate (Int 2e)

To a solution of benzyl (2S)-2-(cyanomethyl)-4-(7-(8-methylnaphthalen-1-yl)-2-(methylthio)-6,7-dihydro-5H-pyrano[2,3-d]pyrimidin-4-yl)piperazine-1-carboxylate (Int 2d) (140 mg, 0.241 m mol) in DCM (1.5 mL) was added m-CPBA (77 mg, 0.45 mmol) at 0° C. under $N_2$ atmosphere. The mixture was stirred at 0° C. for 3 h. The reaction was purified by preparative TLC ($SiO_2$, petroleum ether:ethyl acetate=1:1) to give benzyl (2S)-2-(cyanomethyl)-4-(7-(8-methylnaphthalen-1-yl)-2-(methylsulfinyl)-6,7-dihydro-5H-pyrano[2,3-d]pyrimidin-4-yl)piperazine-1-carboxylate (Int 2e). MS (ESI): m/z $[M+H]^+$ 596.

Step F: benzyl (2S)-2-(cyanomethyl)-4-(7-(8-methylnaphthalen-1-yl)-2-(((S)-1-methylpyrrolidin-2-yl)methoxy)-6,7-dihydro-5H-pyrano[2,3-d]pyrimidin-4-yl)piperazine-1-carboxylate (Int 2f)

To a solution of (S)-(1-methylpyrrolidin-2-yl)methanol (69.6 mg, 0.604 mmol) in THF (1.0 mL) was added sodium 2-methylpropan-2-olate (0.252 mL, 0.504 mmol) (2.0 M in THF) at 0° C. under $N_2$ atmosphere. The mixture was stirred at 0° C. for 10 min. Then benzyl (2S)-2-(cyanomethyl)-4-(7-(8-methylnaphthalen-1-yl)-2-(methylsulfinyl)-6,7-dihydro-5H-pyrano[2,3-d]pyrimidin-4-yl)piperazine-1-carboxylate (Int 2e) (120 mg, 0.201 mmol) in THF (2.0 mL) was added. The mixture was stirred at 0° C. for 1 h. The residue was purified by preparative TLC ($SiO_2$, petroleum ether:ethyl acetate=10:1) to give benzyl (2S)-2-(cyanomethyl)-4-(7-(8-methylnaphthalen-1-yl)-2-(((S)-1-methylpyrrolidin-2-yl)methoxy)-6,7-dihydro-5H-pyrano[2,3-d]pyrimidin-4-yl)piperazine-1-carboxylate (Int 2f). MS (ESI): m/z $[M+H]^+$ 647.

Step G: 2-((2S)-4-(7-(8-methylnaphthalen-1-yl)-2-(((S)-1-methylpyrrolidin-2-yl)methoxy)-6,7-dihydro-5H-pyrano[2,3-d]pyrimidin-4-yl)piperazin-2-yl)acetonitrile (Int 2g)

A solution of benzyl (2S)-2-(cyanomethyl)-4-(7-(8-methylnaphthalen-1-yl)-2-(((S)-1-methylpyrrolidin-2-yl)methoxy)-6,7-dihydro-5H-pyrano[2,3-d]pyrimidin-4-yl)piperazine-1-carboxylate (Int 2f) (87 mg, 0.14 mmol) in TFA (0.3 mL) was stirred at 80° C. for 30 min under nitrogen atmosphere. The mixture was cooled, and the solvent was evaporated under reduced pressure to give the crude product. A portion of the residue was used directly in the next step, and the other portion was purified by preparative HPLC (Column: Boston Green ODS 150 mm×30 mm, 5 μm; Condition: water (0.1% TFA)-MeCN Begin B 23, End B 43; Gradient Time (min): 10; 100% B Hold Time (min): 2; FlowRate (mL/min) 25) to give 2-((2S)-4-(7-(8-methylnaphthalen-1-yl)-2-(((S)-1-methylpyrrolidin-2-yl)methoxy)-6,7-dihydro-5H-pyrano[2,3-d]pyrimidin-4-yl)piperazin-2-yl)acetonitrile (Int 2g). MS (ESI): m/z $[M+H]^+$ 513.

Step H: 2-((2S)-1-acryloyl-4-(7-(8-methylnaphthalen-1-yl)-2-(((S)-1-methylpyrrolidin-2-yl)methoxy)-6,7-dihydro-5H-pyrano[2,3-d]pyrimidin-4-yl)piperazin-2-yl)acetonitrile (Ex. 2)

To a solution of 2-((2S)-4-(7-(8-methylnaphthalen-1-yl)-2-(((S)-1-methylpyrrolidin-2-yl)methoxy)-6,7-dihydro-5H-pyrano[2,3-d]pyrimidin-4-yl)piperazin-2-yl)acetonitrile (Int 2g) (46 mg, 0.090 mmol) in $CH_2Cl_2$ (0.5 mL) was added DIEA (0.016 mL, 0.090 mmol) and acryloyl chloride (8.1 mg, 0.090 mmol) at 0° C. The mixture was stirred at 0° C. for 5 min. The reaction was concentrated in vacuo, and the residue was purified by preparative HPLC (Column: Agela DuraShell C18 150 mm×25 mm, 5 μm; Condition: water (0.04% $NH_3H_2O$+10 mM $NH_4HCO_3$)-MeCN Begin B 43, End B 73; Gradient Time (min): 10; 100% B Hold Time (min): 2; FlowRate (mL/min) 25) to give 2-((2S)-1-acryloyl-4-(7-(8-methylnaphthalen-1-yl)-2-(((S)-1-methylpyrrolidin-2-yl)methoxy)-6,7-dihydro-5H-pyrano[2,3-d]pyrimidin-4-yl)piperazin-2-yl)acetonitrile as a racemic mixture. (Ex. 2) MS (ESI): m/z $[M+H]^+$ 567. $^1$H NMR (400 MHz, Methanol-$d_4$) δ 7.87 (d, J=7.8 Hz, 1H), 7.83-7.75 (m, 2H), 7.48 (dt, J=3.7, 7.7 Hz, 1H), 7.38-7.32 (m, 2H), 6.80 (br s, 1H), 6.44 (br d, J=10.6 Hz, 1H), 6.28 (br d, J=17.2 Hz, 1H), 5.83 (br d, J=10.2 Hz, 1H), 4.34 (br d, J=5.9 Hz, 2H), 4.26 (br d, J=14.1 Hz, 1H), 4.16 (br d, J=13.3 Hz, 1H), 4.12-3.95 (m, 2H), 3.46 (br s, 1H), 3.18-2.97 (m, 5H), 2.91 (s, 3H), 2.86 (br s, 2H), 2.69 (br d, J=13.3 Hz, 1H), 2.55 (d, J=4.3 Hz, 3H), 2.46 (br d, J=7.0 Hz, 2H), 2.11 (br dd, J=8.8, 12.3 Hz, 1H), 1.97-1.90 (m, 1H), 1.89-1.81 (m, 2H), 1.77-1.68 (m, 1H).
Example 3: 2-((2S)-1-acryloyl-4-(7-(2-fluoro-6-hydroxyphenyl)-2-(((S)-1-methylpyrrolidin-2-yl)methoxy)-6,7-dihydro-5H-pyrano[2,3-d]pyrimidin-4-yl)piperazin-2-yl)acetonitrile
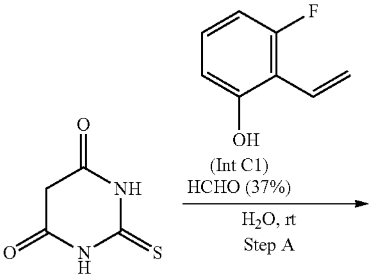
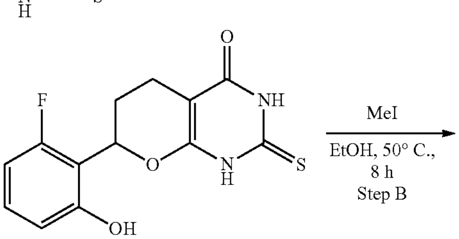
Int 3a
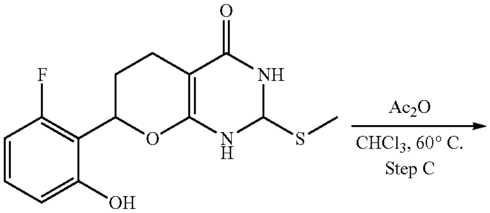
Int 3b
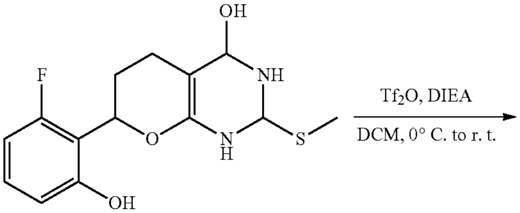
Int 3c
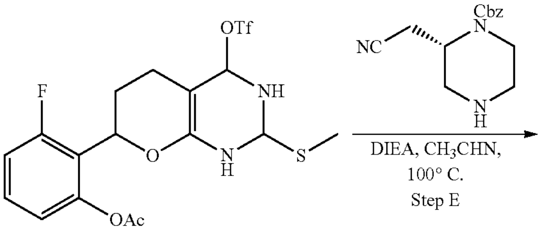
Int 3d
-continued
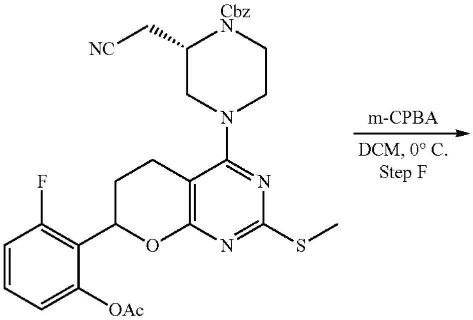
Int 3e
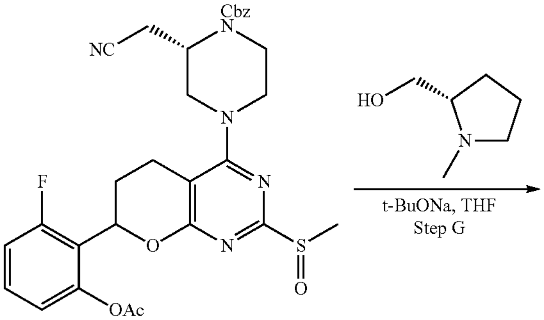
Int 3f
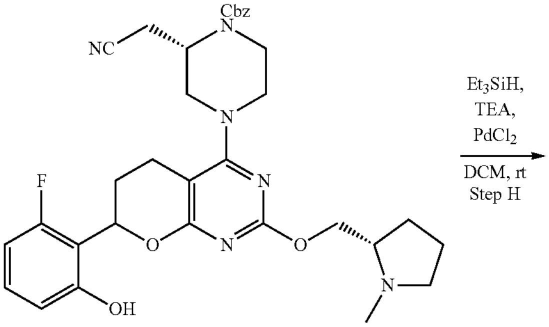
Int 3g
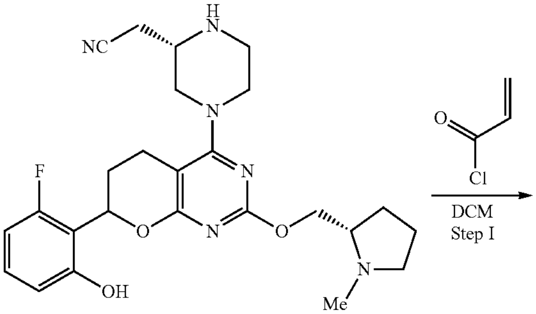
Int 3h -continued

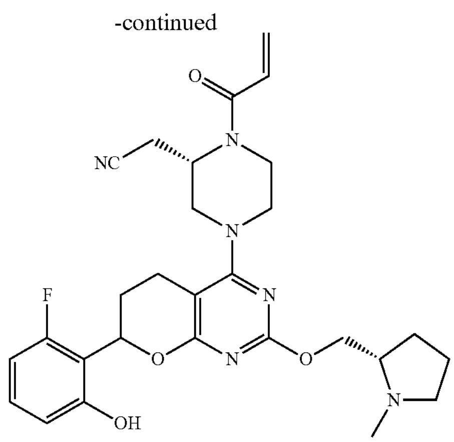

Ex. 3

Step A: 7-(2-fluoro-6-hydroxyphenyl)-2-thioxo-1,2,3,5,6,7-hexahydro-4H-pyrano[2,3-d]pyrimidin-4-one (Int 3a)

A mixture of 3-fluoro-2-vinylphenol (Int C1) (9.00 g, 65.2 mmol), 2-thioxodihydropyrimidine-4,6(1H,5H)-dione (14.1 g, 98.0 mmol) and formaldehyde (37% in water) (9.70 mL, 130 mmol) in dioxane (5 mL) and water (15 mL) was stirred at 25° C. for 17 h. The heterogeneous mixture was filtered and the solid was collected and dried in vacuo to give 7-(2-fluoro-6-hydroxyphenyl)-2-thioxo-1,2,3,5,6,7-hexahydro-4H-pyrano[2,3-d]pyrimidin-4-one (Int 3a). The solid was used directly without further purification. MS (ESI) $[M+H]^+$ m/z: 295.

Step B: 7-(2-fluoro-6-hydroxyphenyl)-2-(methylthio)-6,7-dihydro-3H-pyrano[2,3-d]pyrimidin-4(5H)-one (Int 3b)

A mixture of 7-(2-fluoro-6-hydroxyphenyl)-2-thioxo-1,2,3,5,6,7-hexahydro-4H-pyrano[2,3-d]pyrimidin-4-one (Int 3a) (15.0 g, 51.0 mmol) and iodomethane (3.20 mL, 51.0 mmol) in ethanol (5 mL) was stirred at 60° C. for 8 h. The reaction mixture was quenched with brine (20 mL) and extracted with DCM:MeOH=10:1 (80 mL×3). The combined organic layers were washed with brine (100 mL), dried over $Na_2SO_4$, filtered and the solvent was evaporated under reduced pressure to yield 7-(2-fluoro-6-hydroxyphenyl)-2-(methylthio)-6,7-dihydro-3H-pyrano[2,3-d]pyrimidin-4(5H)-one (Int 3b). The crude product was used directly without further purification. MS (ESI) $[M+H]^+$ m/z: 309.

Step C: 3-fluoro-2-(4-hydroxy-2-(methylthio)-6,7-dihydro-5H-pyrano[2,3-d]pyrimidin-7-yl)phenyl acetate (Int 3c)

A mixture of 7-(2-fluoro-6-hydroxyphenyl)-2-(methylthio)-6,7-dihydro-3H-pyrano[2,3-d]pyrimidin-4(5H)-one (Int 3b) (10 g, 32 mmol) in $CHCl_3$ (5 mL) and $Ac_2O$ (3 mL) was stirred at 60° C. for 4 h. The solvent was removed under reduced pressure, and the residue was dissolved in water (5 mL) and EtOAc (15 mL). The organic layer was separated and the aqueous layer was re-extracted with EtOAc (15 mL×3). The combined organic layers were washed with saturated aqueous $NaHCO_3$ (30 mL) and brine (30 mL), dried over anhydrous $Na_2SO_4$, filtered and concentrated under reduced pressure to yield 3-fluoro-2-(4-hydroxy-2-(methylthio)-6,7-dihydro-5H-pyrano[2,3-d]pyrimidin-7-yl)phenyl acetate (Int 3c). Crude product was used directly without further purification. MS (ESI) $[M+H]^+$ m/z: 351.

Step D: 3-fluoro-2-(2-(methylthio)-4-(((trifluoromethyl)sulfonyl)oxy)-6,7-dihydro-5H-pyrano[2,3-d]pyrimidin-7-yl)phenyl acetate (Int 3d)

To a mixture of 3-fluoro-2-(4-hydroxy-2-(methylthio)-6,7-dihydro-5H-pyrano[2,3-d]pyrimidin-7-yl)phenyl acetate (Int 3c) (1.0 g, 2.9 mmol) and DIEA (1.5 mL, 8.6 mmol) in DCM (20 mL) was added trifluoromethanesulfonic anhydride (0.97 g, 3.4 mmol). After addition, the mixture was stirred at 0° C. for 0.5 h. The solvent was removed under reduced pressure, and the residue was dissolved in water (15 mL) and EtOAc (50 mL). The organic layer was separated, and the aqueous layer was re-extracted with EtOAc (50 mL×3) and the combined organic layers were washed with brine (150 mL), dried over anhydrous $Na_2SO_4$, filtered and concentrated under reduced pressure. The residue was purified by column chromatography on silica gel (ethyl acetate: Pet. ether=1:3, v:v) to yield 3-fluoro-2-(2-(methylthio)-4-(((trifluoromethyl)sulfonyl)oxy)-6,7-dihydro-5H-pyrano[2,3-d]pyrimidin-7-yl)phenyl acetate (Int 3d). MS (ESI) $[M+H]^+$ m/z: 483.

Step E: (2S)-benzyl 4-(7-(2-acetoxy-6-fluorophenyl)-2-(methylthio)-6,7-dihydro-5H-pyrano[2,3-d]pyrimidin-4-yl)-2-(cyanomethyl)piperazine-1-carboxylate (Int 3e)

A mixture of 3-fluoro-2-(2-(methylthio)-4-(((trifluoromethyl)sulfonyl)oxy)-6,7-dihydro-5H-pyrano[2,3-d]pyrimidin-7-yl)phenyl acetate (Int 3d) (60 mg, 0.12 mmol), (S)-benzyl 2-(cyanomethyl)piperazine-1-carboxylate (70.7 mg, 0.273 mmol) and DIEA (0.087 mL, 0.497 mmol) in $CH_3CN$ (3 mL) was stirred at 80° C. for 17 h. The solvent was removed under reduced pressure, and the residue was dissolved in water (15 mL) and EtOAc (15 mL). The organic layer was separated, and the aqueous layer was re-extracted with EtOAc (25 mL×3). The combined organic layers were washed with brine (30 mL), dried over anhydrous $Na_2SO_4$, filtered and concentrated under reduced pressure. The residue was purified by Prep-TLC ($SiO_2$, ethyl acetate:Pet. ether=1:1) to yield (2S)-benzyl 4-(7-(2-acetoxy-6-fluorophenyl)-2-(methylthio)-6,7-dihydro-5H-pyrano[2,3-d]pyrimidin-4-yl)-2-(cyanomethyl)piperazine-1-carboxylate (Int 3e). MS (ESI) $[M+H]^+$ m/z: 592.

Step F: (2S)-benzyl 4-(7-(2-acetoxy-6-fluorophenyl)-2-(methylsulfinyl)-6,7-dihydro-5H-pyrano[2,3-d]pyrimidin-4-yl)-2-(cyanomethyl)piperazine-1-carboxylate (Int 3f)

A mixture of (2S)-benzyl 4-(7-(2-acetoxy-6-fluorophenyl)-2-(methylthio)-6,7-dihydro-5H-pyrano[2,3-d]pyrimidin-4-yl)-2-(cyanomethyl)piperazine-1-carboxylate (Int 3e) (28 mg, 0.047 mmol) and m-CPBA (10 mg, 0.047 mmol) in DCM (3 mL) was stirred at 25° C. for 1 h. The mixture was concentrated in vacuo to give (2S)-benzyl 4-(7-(2-acetoxy-6-fluorophenyl)-2-(methylsulfinyl)-6,7-dihydro-5H-pyrano[2,3-d]pyrimidin-4-yl)-2-(cyanomethyl)piperazine-1-carboxylate (Int 3f), which was used driectly without further purification. MS (ESI) $[M+H]^+$ m/z: 608.

Step G: (2S)-benzyl 2-(cyanomethyl)-4-(7-(2-fluoro-6-hydroxyphenyl)-2-(((S)-1-methylpyrrolidin-2-yl)methoxy)-6,7-dihydro-5H-pyrano[2,3-d]pyrimidin-4-yl)piperazine-1-carboxylate (Int 3g)

To a solution of (S)-(1-methylpyrrolidin-2-yl)methanol (21.2 mg, 0.184 mmol) in THF (2 mL) was added sodium 2-methylpropan-2-olate (0.046 mL, 0.092 mmol, 2 M solution in THF) at 0° C. under $N_2$ atmosphere. Then (2S)-benzyl 4-(7-(2-acetoxy-6-fluorophenyl)-2-(methylsulfinyl)-6,7-dihydro-5H-pyrano[2,3-d]pyrimidin-4-yl)-2-(cyanomethyl)piperazine-1-carboxylate (Int 3f) (28 mg, 0.046 mmol) in THF (1 mL) was added. The mixture was stirred at 0° C. for 1 h. The mixture was evaporated under reduced pressure to give (2S)-benzyl 2-(cyanomethyl)-4-(7-(2-fluoro-6-hydroxyphenyl)-2-(((S)-1-methylpyrrolidin-2-yl)methoxy)-6,7-dihydro-5H-pyrano[2,3-d]pyrimidin-4-yl) piperazine-1-carboxylate (Int 3g), which was used directly without further purification. MS (ESI) $[M+H]^+$ m/z: 617.

Step H: 2-((2S)-4-(7-(2-fluoro-6-hydroxyphenyl)-2-(((S)-1-methylpyrrolidin-2-yl)methoxy)-6,7-dihydro-5H-pyrano[2,3-d]pyrimidin-4-yl)piperazin-2-yl)acetonitrile (Int 3h)

To a solution of (2S)-benzyl 2-(cyanomethyl)-4-(7-(2-fluoro-6-hydroxyphenyl)-2-(((S)-1-methylpyrrolidin-2-yl) methoxy)-6,7-dihydro-5H-pyrano[2,3-d]pyrimidin-4-yl) piperazine-1-carboxylate (Int 3g) (20 mg, 0.032 mmol), $PdCl_2$ (0.6 mg, 3 μmol) and TEA (0.023 mL, 0.16 mmol) in DCM (3.0 mL) was added triethylsilane (37.7 mg, 0.324 mmol) at 0° C. for 1 min. The mixture was stirred at 0° C. for 10 min. LCMS showed that desired product was formed. The mixture was concentrated in vacuo to give 2-((2S)-4-(7-(2-fluoro-6-hydroxyphenyl)-2-(((S)-1-methylpyrrolidin-2-yl)methoxy)-6,7-dihydro-5H-pyrano[2,3-d]pyrimidin-4-yl)piperazin-2-yl)acetonitrile (Int 3h), which was used directly without further purification. MS (ESI) $[M+H]^+$ m/z: 483.

Step J: 2-((2S)-1-acryloyl-4-(7-(2-fluoro-6-hydroxyphenyl)-2-4(S)-1-methylpyrrolidin-2-yl)methoxy)-6,7-dihydro-5H-pyrano[2,3-d]pyrimidin-4-yl)piperazin-2-yl)acetonitrile (Ex. 3)

To a solution of 2-((2S)-4-(7-(2-fluoro-6-hydroxyphenyl)-2-(((S)-1-methylpyrrolidin-2-yl)methoxy)-6,7-dihydro-5H-pyrano[2,3-d]pyrimidin-4-yl)piperazin-2-yl)acetonitrile (Int 3h) (10 mg, 0.021 mmol) in DCM (2 mL) was added TEA (8.7 μL, 0.062 mmol) and acryloyl chloride (1.7 mg, 0.019 mmol) at 0° C. for 5 min. The mixture was concentrated and the residue was purified by Prep-HPLC (Instrument Method Column: YMC-Actus Triart C18 150 mm×30 mm, 5 um; Condition water (0.1% TFA)-ACN Begin B 26 End B 55 Gradient Time (min) 11 100% B Hold Time (min) 2 FlowRate (mL/min)) to yield 2-((2S)-1-acryloyl-4-(7-(2-fluoro-6-hydroxyphenyl)-2-(((S)-1-methylpyrrolidin-2-yl)methoxy)-6,7-dihydro-5H-pyrano[2,3-d]pyrimidin-4-yl)piperazin-2-yl)acetonitrile (Ex. 3) as a racemic mixture. MS (ESI): $[M+H]^+$ m/z: 537; $^1H$ NMR (500 MHz, Methanol-$d_4$) δ 7.24-7.14 (m, 1H), 6.69 (d, J=8.2 Hz, 1H), 6.64-6.56 (m, 1H), 6.31 (br d, J=17.2 Hz, 1H), 5.89-5.80 (m, 2H), 4.98 (br s, 1H), 4.72 (br d, J=12.7 Hz, 2H), 4.56-4.47 (m, 1H), 4.16-4.02 (m, 2H), 3.84 (br s, 1H), 3.78-3.60 (m, 4H), 3.26-3.13 (m, 2H), 3.06 (br d, J=7.6 Hz, 3H), 2.93 (br d, J=13.0 Hz, 2H), 2.77-2.68 (m, 1H), 2.49-2.32 (m, 2H), 2.24-1.96 (m, 5H).

Example 4a/b: 2-((2S)-1-Acryloyl-4-(7-(5-chloro-6-methyl-1H-indazol-4-yl)-2-(((S)-1-methylpyrrolidin-2-yl)methoxy)-6,7-dihydro-5H-pyrano[2,3-d]pyrimidin-4-yl)piperazin-2-yl)acetonitrile

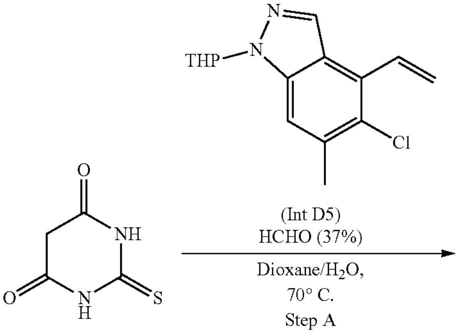

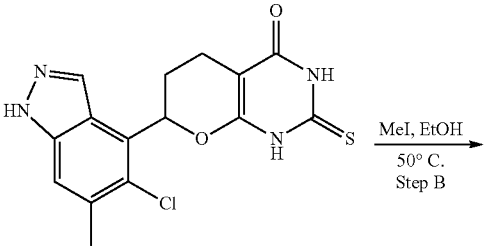

Int 4a

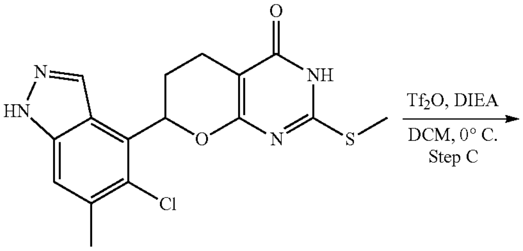

Int 4b

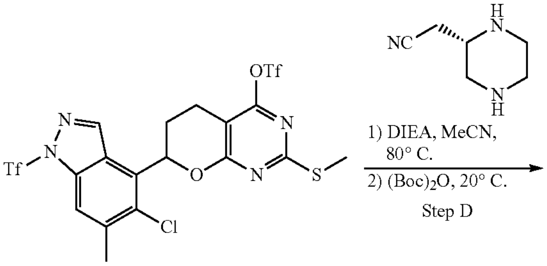

Int 4c

-continued

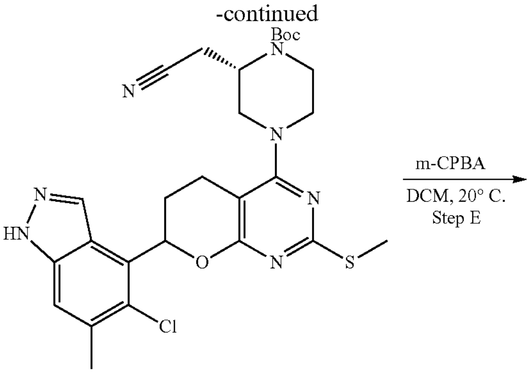

Int 4d

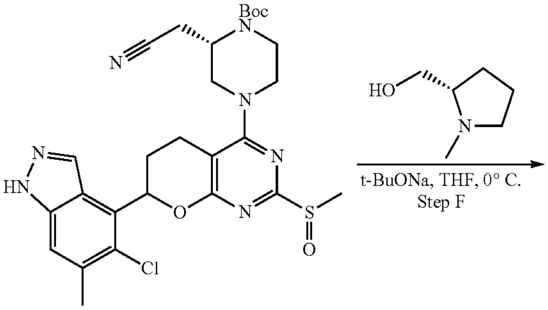

Int 4e

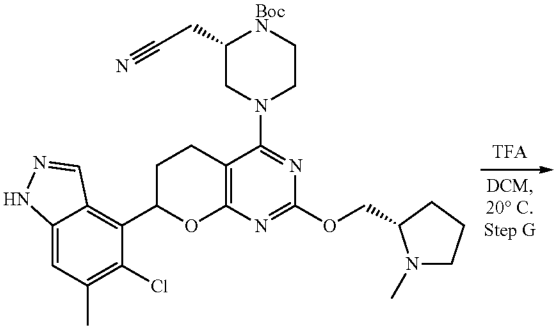

Int 4f

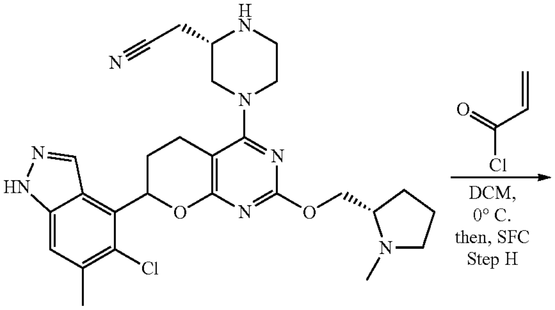

Int 4g

-continued

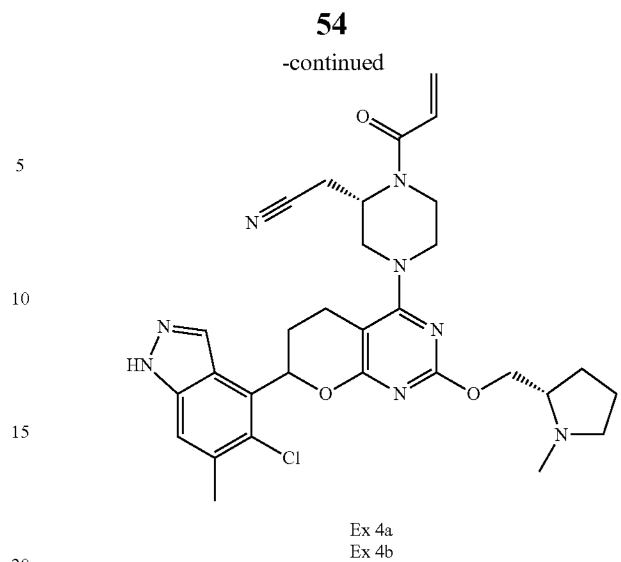

Ex 4a
Ex 4b

Step A: 7-(5-Chloro-6-methyl-1H-indazol-4-yl)-2-thioxo-1,2,3,5,6,7-hexahydro-4H-pyrano[2,3-d]pyrimidin-4-one (Int 4a)

A mixture of 5-chloro-6-methyl-1-(tetrahydro-2H-pyran-2-yl)-4-vinyl-1H-indazole (Int D5) (2.00 g, 7.23 mmol), 2-thioxodihydropyrimidine-4,6(1H,5H)-dione (1.56 g, 10.8 mmol), and formaldehyde (37% in water) (1.08 mL, 14.5 mmol) in water (30 mL) and dioxane (8.0 mL) was stirred at 70° C. for 17 h. The mixture was filtered and the solid was collected and dried in vacuo to give crude 7-(5-chloro-6-methyl-1H-indazol-4-yl)-2-thioxo-1,2,3,5,6,7-hexahydro-4H-pyrano[2,3-d]pyrimidin-4-one (Int 4a). The solid was used directly without further purification. MS (ESI): $[M+H]^+$ m/z: 349.

Step B: 7-(5-Chloro-6-methyl-1H-indazol-4-yl)-2-(methylthio)-6,7-dihydro-3H-pyrano[2,3-d]pyrimidin-4(5H)-one (Int 4b)

A mixture of 7-(5-chloro-6-methyl-1H-indazol-4-yl)-2-thioxo-1,2,3,5,6,7-hexahydro-4H-pyrano[2,3-d]pyrimidin-4-one (2.0 g, 5.7 mmol) (Int 4a) and iodomethane (2.0 g, 0.36 mL, 5.7 mmol) in EtOH (30 mL) was stirred at 50° C. for 17 h. The mixture was concentrated and the residue was purified by flash silica gel chromatography (eluent of 80% ethyl acetate/Pet. ether gradient) to yield 7-(5-chloro-6-methyl-1H-indazol-4-yl)-2-(methylthio)-6,7-dihydro-3H-pyrano[2,3-d]pyrimidin-4(5H)-one (Int 4b). MS (ESI): $[M+H]^+$ m/z: 363.

Step C: 7-(5-Chloro-6-methyl-1-((trifluoromethyl)sulfonyl)-1H-indazol-4-yl)-2-(methylthio)-6,7-dihydro-5H-pyrano[2,3-d]pyrimidin-4-yltrifluoromethanesulfonate (Int 4c)

To a stirred solution of 7-(5-chloro-6-methyl-1H-indazol-4-yl)-2-(methylthio)-6,7-dihydro-3H-pyrano[2,3-d]pyrimidin-4(5H)-one (Int 4b) (170 mg, 0.470 mmol) and DIEA (0.25 mL, 1.4 mmol) in DCM (5 mL) was added $Tf_2O$ (0.237 mL, 1.41 mmol) at 0° C. After addition, the mixture was stirred at 0° C. for 1 h. The solvent was removed under reduced pressure and the residue was dissolved in water (5 mL) and EtOAc (5 mL). The organic layer was separated and the aqueous was re-extracted with EtOAc (5 mL×3), and the combined organic layers were washed with brine (8 mL), dried over anhydrous $Na_2SO_4$, filtered and concentrated under reduced pressure. The residue was purified by Prep-TLC (silica gel, ethyl acetate/Pet. ether=5/1, v/v) to yield 7-(5-chloro-6-methyl-1-((trifluoromethyl)sulfonyl)-1H-indazol-4-yl)-2-(methylthio)-6,7-dihydro-5H-pyrano[2,3-d]pyrimidin-4-yltrifluoromethanesulfonate (Int 4c). MS (ESI): $[M+H]^+$ m/z: 627.

Step D: tert-Butyl (2S)-4-(7-(5-chloro-6-methyl-1H-indazol-4-yl)-2-(methylthio)-6,7-dihydro-5H-pyrano[2,3-d]pyrimidin-4-yl)-2-(cyanomethyl)piperazine-1-carboxylate (Int 4d)

A mixture of (S)-2-(piperazin-2-yl)acetonitrile, 2HCl (95 mg, 0.48 mmol), DIEA (0.21 mL, 1.2 mmol) and 7-(5-chloro-6-methyl-1-((trifluoromethyl)sulfonyl)-1H-indazol-4-yl)-2-(methylthio)-6,7-dihydro-5H-pyrano[2,3-d]pyrimidin-4-yl trifluoromethanesulfonate (Int 4c) (250 mg, 0.400 mmol) in MeCN (2 mL) was stirred at 80° C. for 1 h. To the resulting mixture was added $Boc_2O$ (0.093 mL, 0.40 mmol), and the mixture was stirred at 20° C. for 0.5 h. The mixture was concentrated and the residue was purified by Prep-TLC (silica gel, ethyl acetate/pet. ether=1/3, v/v) to yield tert-butyl (2S)-4-(7-(5-chloro-6-methyl-1H-indazol-4-yl)-2-(methylthio)-6,7-dihydro-5H-pyrano[2,3-d]pyrimidin-4-yl)-2-(cyanomethyl)piperazine-1-carboxylate (Int 4d). MS (ESI): $[M+H]^+$ m/z: 570.

Step E: tert-Butyl (2S)-4-(7-(5-chloro-6-methyl-1H-indazol-4-yl)-2-(methylsulfinyl)-6,7-dihydro-5H-pyrano[2,3-d]pyrimidin-4-yl)-2-(cyanomethyl)piperazine-1-carboxylate (Int 4e)

A mixture of tert-butyl (2S)-4-(7-(5-chloro-6-methyl-1H-indazol-4-yl)-2-(methylthio)-6,7-dihydro-5H-pyrano[2,3-d]pyrimidin-4-yl)-2-(cyanomethyl)piperazine-1-carboxylate (Int 4d) (75 mg, 0.13 mmol) and m-CPBA (43 mg, 0.20 mmol) in DCM (3 mL) was stirred at 20° C. for 1 h. The solvent was removed under reduced pressure and the residue was dissolved in water (5 mL) and EtOAc (5 mL). The organic layer was separated, and the aqueous layer was re-extracted with EtOAc (5 mL×3). The combined organic layers were washed with brine (20 mL), dried over anhydrous $Na_2SO_4$, filtered and concentrated under reduced pressure to yield crude tert-butyl (2S)-4-(7-(5-chloro-6-methyl-1H-indazol-4-yl)-2-(methyl sulfinyl)-6,7-dihydro-5H-pyrano[2,3-d]pyrimidin-4-yl)-2-(cyanomethyl)piperazine-1-carboxylate (Int 4e). The solid was used directly without further purification. MS (ESI): $[M+H]^+$ m/z: 586.

Step F: tert-Butyl (2S)-4-(7-(5-chloro-6-methyl-1H-indazol-4-yl)-2-(((S)-1-methylpyrrolidin-2-yl)methoxy)-6,7-dihydro-5H-pyrano[2,3-d]pyrimidin-4-yl)-2-(cyanomethyl)piperazine-1-carboxylate (Int 4f)

To a solution of (S)-(1-methylpyrrolidin-2-yl)methanol (59 mg, 0.51 mmol) in THF (0.5 mL) was added sodium tert-butoxide (2 M in THF) (0.128 mL, 0.256 mmol) at 0° C. under $N_2$ atmosphere. Then, tert-butyl (2S)-4-(7-(5-chloro-6-methyl-1H-indazol-4-yl)-2-(methylsulfinyl)-6,7-dihydro-5H-pyrano[2,3-d]pyrimidin-4-yl)-2-(cyanomethyl)piperazine-1-carboxylate (Int 4e) (75.0 mg, 0.128 mmol) in THF (0.5 mL) was added. The mixture was stirred at 0° C. for 0.5 h. The reaction mixture was quenched with water (10 mL) and extracted with EtOAc (10 mL×3). The combined organic phases were washed with brine (30 mL), dried over anhydrous $Na_2SO_4$, filtered and concentrated under reduced pressure to give the crude. The residue was purified by Prep-TLC (silica gel, DCM/MeOH=5/1, v/v) to yield tert-butyl (2S)-4-(7-(5-chloro-6-methyl-1H-indazol-4-yl)-2-(((S)-1-methylpyrrolidin-2-yl)methoxy)-6,7-dihydro-5H-pyrano[2,3-d]pyrimidin-4-yl)-2-(cyanomethyl)piperazine-1-carboxylate (Int 4f). MS (ESI): $[M+H]^+$ m/z: 637.

Step G: 2-((2S)-4-(7-(5-Chloro-6-methyl-1H-indazol-4-yl)-2-(((S)-1-methylpyrrolidin-2-yl)methoxy)-6,7-dihydro-5H-pyrano[2,3-d]pyrimidin-4-yl)piperazin-2-yl)acetonitrile (Int 4g)

A mixture of tert-butyl (2S)-4-(7-(5-chloro-6-methyl-1H-indazol-4-yl)-2-(((S)-1-methylpyrrolidin-2-yl)methoxy)-6,7-dihydro-5H-pyrano[2,3-d]pyrimidin-4-yl)-2-(cyanomethyl)piperazine-1-carboxylate (Int 4f) (45 mg, 0.071 mmol) in TFA (0.2 mL) and DCM (1 mL) was stirred at 20° C. for 0.5 h. The mixture was concentrated to give crude 2-((2S)-4-(7-(5-chloro-6-methyl-1H-indazol-4-yl)-2-(((S)-1-methylpyrrolidin-2-yl)methoxy)-6,7-dihydro-5H-pyrano[2,3-d]pyrimidin-4-yl)piperazin-2-yl)acetonitrile, TFA (Int 4g). MS (ESI): $[M+H]^+$ m/z: 537.

Step H: 2-((2S)-1-Acryloyl-4-(7-(5-chloro-6-methyl-1H-indazol-4-yl)-2-(((S)-1-methylpyrrolidin-2-yl)methoxy)-6,7-dihydro-5H-pyrano[2,3-d]pyrimidin-4-yl)piperazin-2-yl)acetonitrile (Ex. 4a/b)

To a mixture of 2-((2S)-4-(7-(5-chloro-6-methyl-1H-indazol-4-yl)-2-(((S)-1-methylpyrrolidin-2-yl)methoxy)-6,7-dihydro-5H-pyrano[2,3-d]pyrimidin-4-yl)piperazin-2-yl)acetonitrile (Int 4g) (45 mg, 0.084 mmol) and TEA (0.035 mL, 0.25 mmol) in THF (0.5 mL) and water (0.5 mL) was added acryloyl chloride (11.4 mg, 0.126 mmol). After addition, the mixture was stirred at 0° C. for 0.5 h. The mixture was concentrated and the residue was purified by Prep-HPLC (Column Agela: DuraShell C18 150 mm×25 mm, 5 um; Condition: water (0.05% $NH_3H_2O$+10 mM $NH_4HCO_3$)-ACN Begin B 37, End B 67; Gradient Time (min): 10; 100% B Hold Time (min): 2; FlowRate (mL/min) 25). The racemic solid was then separated by preparative SFC (Column B; Condition: 0.1% $NH_3H_2O$ in EtOH) to yield 2-((2S)-1-acryloyl-4-(7-(5-chloro-6-methyl-1H-indazol-4-yl)-2-(((S)-1-methylpyrrolidin-2-yl)methoxy)-6,7-dihydro-5H-pyrano[2,3-d]pyrimidin-4-yl)piperazin-2-yl)acetonitrile; Peak 1 (Ex. 4a). MS (ESI): $[M+H]^+$ m/z: 591. $^1$H NMR (500 MHz, Methanol-$d_4$) δ 8.19 (s, 1H), 7.52 (s, 1H), 6.85 (br s, 1H), 6.31 (br d, J=16.2 Hz, 1H), 6.05 (br d, J=10.4 Hz, 1H), 5.85 (br d, J=9.2 Hz, 1H), 4.61 (s, 2H), 4.43 (br s, 1H), 4.19-4.11 (m, 2H), 3.84-3.44 (m, 1H), 3.30-2.98 (m, 7H), 2.91-2.61 (m, 5H), 2.56 (s, 3H), 2.44 (br d, J=8.2 Hz, 1H), 2.22-2.13 (m, 1H), 2.08-1.97 (m, 2H), 1.90 (br s, 2H), 1.81 (br d, J=14.3 Hz, 1H); and 2-((2S)-1-acryloyl-4-(7-(5-chloro-6-methyl-1H-indazol-4-yl)-2-(((S)-1-methylpyrrolidin-2-yl)methoxy)-6,7-dihydro-5H-pyrano[2,3-d]pyrimidin-4-yl)piperazin-2-yl)acetonitrile; Peak 2 (Ex. 4b). MS (ESI): $[M+H]^+$ m/z: 591. $^1$H NMR (500 MHz, Methanol-$d_4$) δ 8.24 (s, 1H), 7.58 (s, 1H), 6.91 (br s, 1H), 6.38 (br d, J=17.5 Hz, 1H), 6.15-6.08 (m, 1H), 5.93 (br d, J=10.1 Hz, 1H), 4.70-4.45 (m, 2H), 4.44-4.11 (m, 2H), 4.10-3.40 (m, 2H), 3.32-3.04 (m, 6H), 2.80 (br s, 5H), 2.62 (s, 3H), 2.51 (br d, J=11.9 Hz, 1H), 2.33-2.23 (m, 1H), 2.17-2.03 (m, 2H), 2.01-1.93 (m, 3H), 1.91 (br s, 1H).

Examples 5-8 were prepared using methods similar to those described in Example 4 from the indicated alkene precursor.

| Ex. | Alkene Precursor | Structure | Compound Name | $[M + H]^+$ Found | SFC Conditions |
|---|---|---|---|---|---|
| 5a | Int E1 | 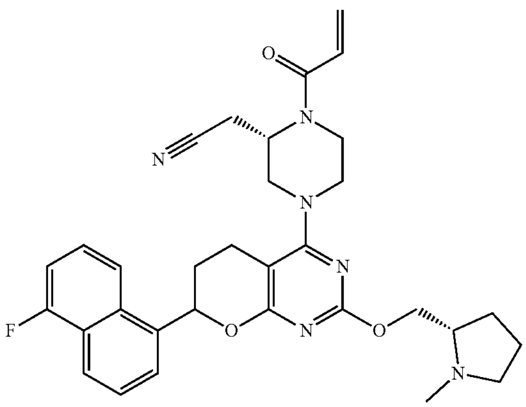 Peak 1 | 2-((2S)-1-acryloyl-4-(7-(5-fluoronaphthalen-1-yl)-2-(((S)-1-methylpyrrolidin-2-yl)methoxy-6,7-dihydro-5H-pyrano[2,3-d]pyrimidin-4-yl)piperazin-2-yl)acetonitrile | 571 | Column C, Condition: 0.1% $NH_3H_2O$/IPA |
| 5b | Int E1 | 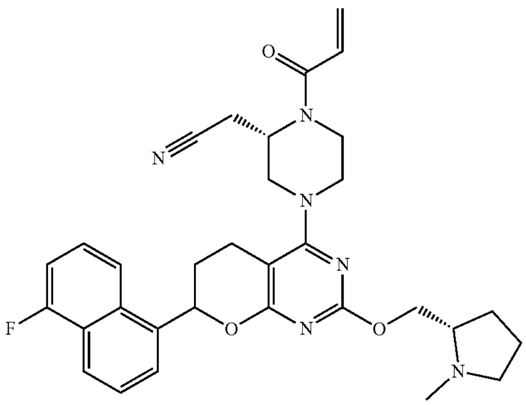 Peak 2 | 2-((2S)-1-acryloyl-4-(7-(5-fluoronapthalen-1-yl)-2-(((S)-1-methylpyrrolidin-2-yl)methoxy)-6,7-dihydro-5H-pyrano[2,3-d]pyrimidin-4-yl)piperazin-2-yl)acetonitrile | 571 | Same as Ex 5a |
| 6 | Int F1 | 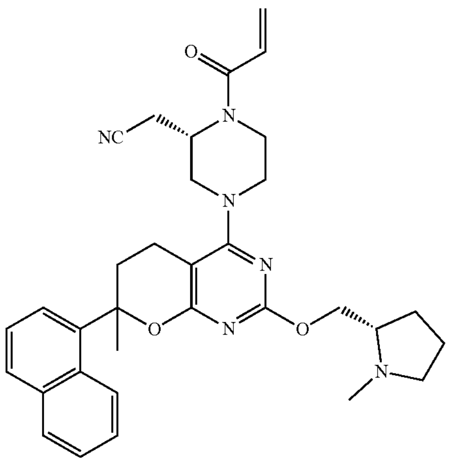 [SMILES: C=CC(=O)N1CCN(c2nc(OC[C@@H]3CCCN3C)nc3c2CCC(C)(c2cccc4ccccc24)O3)C[C@@H]1CC#N] | 2-((2S)-1-acryloyl-4-(7-methyl-2-(((S)-1-methylpyrrolidin-2-yl)methoxy)-7-(naphthalen-1-yl)-6,7-dihydro-5H-pyrano[2,3-d]pyrimidin-4-yl)piperazin-2-yl)acetonitrile | 567 | NA |

-continued

| Ex. | Alkene Precursor | Structure | Compound Name | $[M + H]^+$ Found | SFC Conditions |
|---|---|---|---|---|---|
| 7a | Int G1 | 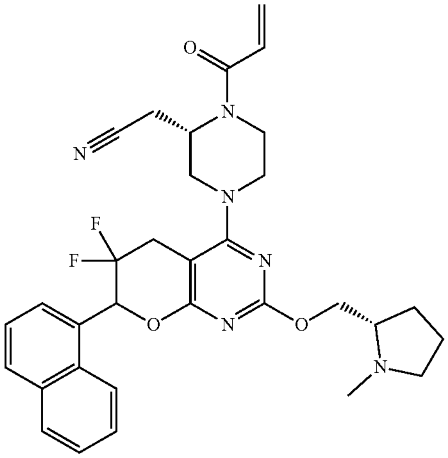 Peak 1 | 2-((2S)-1-acryloyl-4-(6,6-difluoro-2-(((S)-1-methylpyrrolidin-2-yl)methoxy)-7-(naphthalen-1-yl)-6,7-dihydro-5H-pyrano[2,3-d]pyrimidin-4-yl)piperazin-2-yl)acetonitrile | 589 | Column D; Condition: 0.1% $NH_3•H_2O$ EtOH |
| 7b | Int G1 | 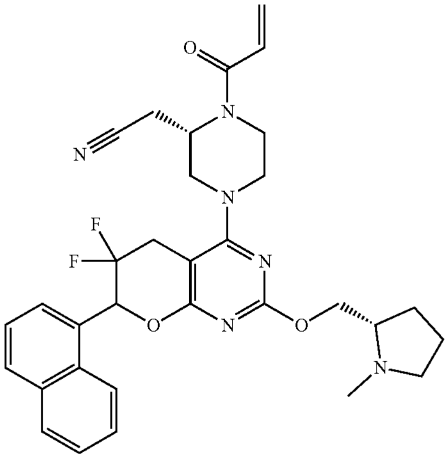 Peak 2 | 2-((2S)-1-acryloyl-4-(6,6-difluoro-2-(((S)-1-methylpyrrolidin-2-yl)methoxy)-7-(naphthalen-1-yl)-6,7-dihydro-5H-pyrano[2,3-d]pyrimidin-4-yl)piperazin-2-yl)acetonitrile | 589 | Same as Ex 7a |
| 8a | Int H4 | 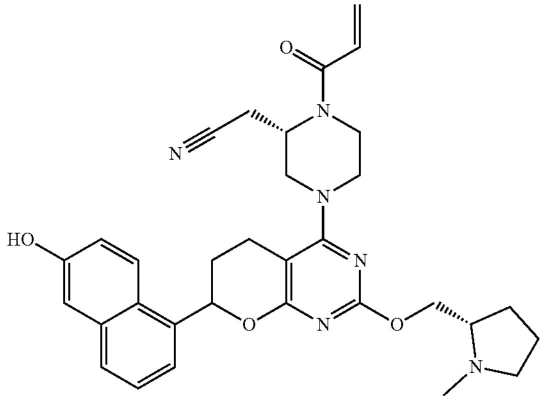 Peak 1 | 2-((2S)-1-acryloyl-4-(7-(6-hydroxynaphthalen-1-yl)-2-(((S)-1-methylpyrrolidin-2-yl)methoxy)-6,7-dihydro-5H-pyrano[2,3-d]pyrimidin-4-yl)piperazin-2-yl)acetonitrile | 569 | Column B Condition: 0.1% $NH_3H_2O$ EtOH |

Example 9a/b: 2-((2S)-1-Acryloyl-4-(6-methyl-2-4 (S)-1-methylpyrrolidin-2-yl)methoxy)-7-(naphthalen-1-yl)-6,7-dihydro-5H-pyrano[2,3-d]pyrimidin-4-yl)piperazin-2-yl)acetonitrile
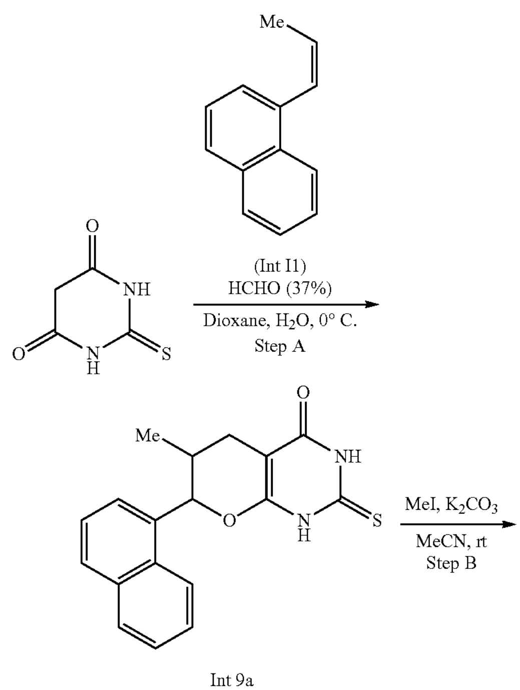
Int 9a
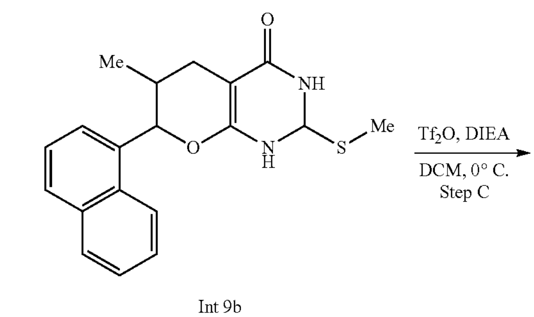
Int 9b
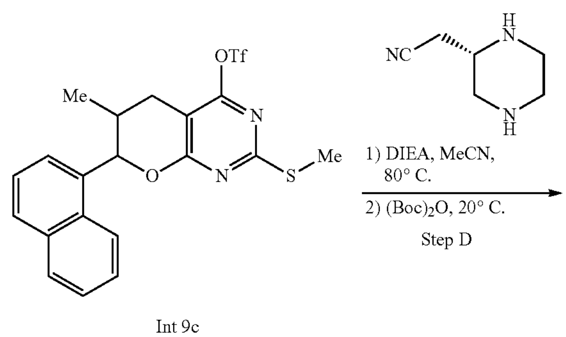
Int 9c
-continued
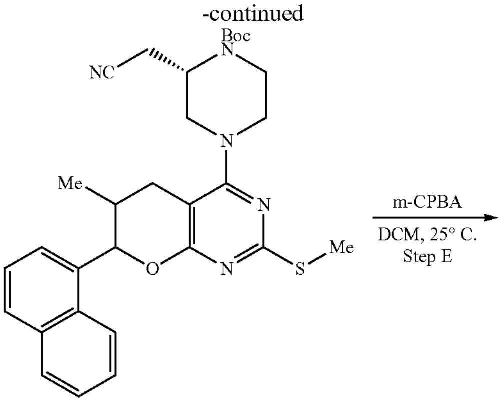
Int 9d
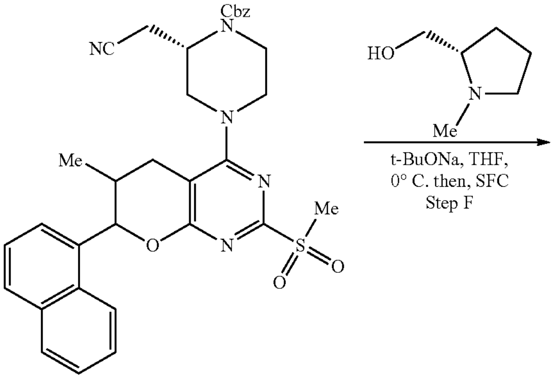
Int 9e
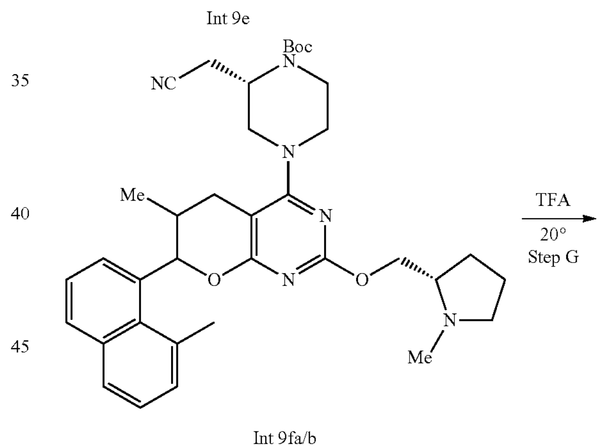
Int 9fa/b
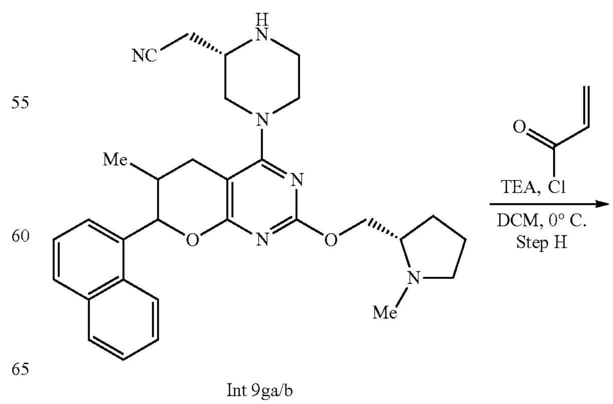
Int 9ga/b -continued

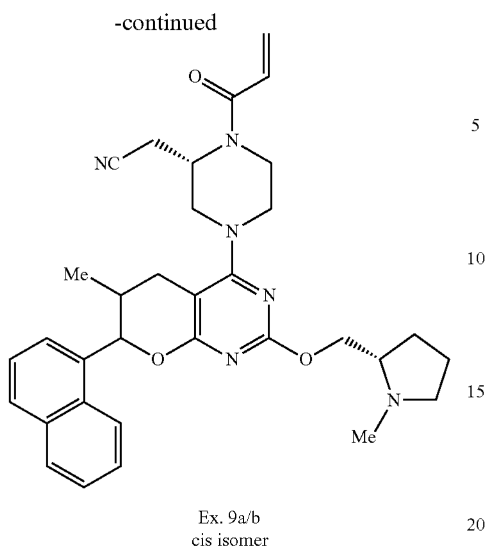

Ex. 9a/b
cis isomer

Step A: 6-Methyl-7-(naphthalen-1-yl)-2-thioxo-1,2,3,5,6,7-hexahydro-4H-pyrano[2,3-d]pyrimidin-4-one (Int 9a)

A mixture of 1-(prop-1-en-1-yl)naphthalene (Int I1) (3.00 g, 17.8 mmol), 2-thioxodihydropyrimidine-4,6(1H,5H)-dione (3.86 g, 26.7 mmol) and formaldehyde (37% in water) (2.66 mL, 35.7 mmol) in water (30 mL) and dioxane (30 mL) was stirred at 70° C. for 17 h. The mixture was filtered and the solid was collected and dried in vacuo to yield crude 6-methyl-7-(naphthalen-1-yl)-2-thioxo-1,2,3,5,6,7-hexahydro-4H-pyrano[2,3-d]pyrimidin-4-one (Int 9a). The solid was used directly without further purification. MS (ESI): $[M+H]^+$ m/z: 325.

Step B: 6-Methyl-2-(methylthio)-7-(naphthalen-1-yl)-3,5,6,7-tetrahydro-4H-pyrano[2,3-d]pyrimidin-4-one (Int 9b)

A mixture of 6-methyl-7-(naphthalen-1-yl)-2-thioxo-1,2,3,5,6,7-hexahydro-4H-pyrano[2,3-d]pyrimidin-4-one (Int 9a) (5.00 g, 14.8 mmol), potassium carbonate (3.1 g, 22 mmol) and iodomethane (0.92 mL, 14.8 mmol) in MeCN (100 mL) was stirred at 25° C. for 1 h. The reaction mixture was quenched with water (50 mL), and extracted with DCM/MeOH=10/1 (3×50 mL). The combined organic layers were washed with brine (100 mL), dried over $Na_2SO_4$, filtered and the solvent was evaporated under reduced pressure to yield 6-methyl-2-(methylthio)-7-(naphthalen-1-yl)-3,5,6,7-tetrahydro-4H-pyrano[2,3-d]pyrimidin-4-one (Int 9b). Crude product was used directly without further purification. MS (ESI): $[M+H]^+$ m/z: 339.

Step C: 6-Methyl-2-(methylthio)-7-(naphthalen-1-yl)-6,7-dihydro-5H-pyrano[2,3-d]pyrimidin-4-yl trifluoromethanesulfonate (Int 9c)

To a mixture of 6-methyl-2-(methylthio)-7-(naphthalen-1-yl)-3,5,6,7-tetrahydro-4H-pyrano[2,3-d]pyrimidin-4-one (Int 9b) (1.50 g, 4.43 mmol) and DIPEA (2.3 mL, 13 mmol) in DCM (30 mL) was added $Tf_2O$ (1.1 mL, 6.7 mmol) at 0° C. After addition, the mixture was stirred at 0° C. for 1 h. The solvent was removed under reduced pressure and the residue was dissolved in water (50 mL) and EtOAc (50 mL). The organic layer was separated, and the aqueous layer was re-extracted with EtOAc (50 mL×3), and the combined organic layers were washed with brine (80 mL), dried over anhydrous $Na_2SO_4$, filtered and concentrated under reduced pressure. The crude material was chromatographed on silica gel (EtOAc/Pet. ether, 0:100 to 2:98) to yield 6-methyl-2-(methylthio)-7-(naphthalen-1-yl)-6,7-dihydro-5H-pyrano[2,3-d]pyrimidin-4-yl trifluoromethanesulfonate (Int 9c). MS (ESI): $[M+H]^+$ m/z: 471.

Step D: tert-Butyl (2S)-2-(cyanomethyl)-4-(6-methyl-2-(methylthio)-7-(naphthalen-1-yl)-6,7-dihydro-5H-pyrano[2,3-d]pyrimidin-4-yl)piperazine-1-carboxylate (Int 9d)

A mixture of 6-methyl-2-(methylthio)-7-(naphthalen-1-yl)-6,7-dihydro-5H-pyrano[2,3-d]pyrimidin-4-yl trifluoromethanesulfonate (Int 9c) (1.60 g, 3.40 mmol), (S)-2-(piperazin-2-yl)acetonitrile, 2HCl (0.876 g, 4.42 mmol) and DIEA (2.97 mL, 17.0 mmol) in MeCN (30 mL) was stirred at 80° C. for 1 h. To the resulting mixture was added $Boc_2O$ (1.58 mL, 6.80 mmol), and the mixture was stirred at 20° C. for 0.5 h. The mixture was concentrated and the residue was purified on silica gel (EtOAc/Pet. ether, 5:95 to 15:85) to yield tert-butyl (2S)-2-(cyanomethyl)-4-(6-methyl-2-(methylthio)-7-(naphthalen-1-yl)-6,7-dihydro-5H-pyrano[2,3-d]pyrimidin-4-yl)piperazine-1-carboxylate (Int 9d). $^1H$ NMR (400 MHz, $CDCl_3$) δ 8.14-7.41 (m, 7H), 6.16-5.56 (m, 1H), 4.69-4.30 (m, 2H), 4.06-3.67 (m, 4H), 3.49-3.14 (m, 2H), 3.11-2.96 (m, 2H), 2.58-2.39 (m, 5H), 1.47 (s, 9H), 1.00-0.60 (m, 3H).

Step E: tert-Butyl (2S)-2-(cyanomethyl)-4-(6-methyl-2-(methylsulfonyl)-7-(naphthalen-1-yl)-6,7-dihydro-5H-pyrano[2,3-d]pyrimidin-4-yl)piperazine-1-carboxylate (Int 9e)

A mixture of tert-butyl (2S)-2-(cyanomethyl)-4-(6-methyl-2-(methylthio)-7-(naphthalen-1-yl)-6,7-dihydro-5H-pyrano[2,3-d]pyrimidin-4-yl)piperazine-1-carboxylate (Int 9d) (800 mg, 1.47 mmol) and m-CPBA (696 mg, 3.23 mmol) in DCM (15 mL) was stirred at 25° C. for 1 h. The solvent was removed under reduced pressure, and the residue was dissolved in water (20 mL) and EtOAc (20 mL). The organic layer was separated and the aqueous layer was re-extracted with EtOAc (20 mL×3) and the combined organic layers were washed with brine (60 mL), dried over anhydrous $Na_2SO_4$, filtered and concentrated under reduced pressure to yield crude tert-butyl (2S)-2-(cyanomethyl)-4-(6-methyl-2-(methylsulfonyl)-7-(naphthalen-1-yl)-6,7-dihydro-5H-pyrano[2,3-d]pyrimidin-4-yl)piperazine-1-carboxylate (Int 9e). The solid was used directly without further purification. MS (ESI): $[M+H]^+$ m/z: 578.

Step F: tert-Butyl (2S)-2-(cyanomethyl)-4-(6-methyl-2-(((S)-1-methylpyrrolidin-2-yl)methoxy)-7-(naphthalen-1-yl)-6,7-dihydro-5H-pyrano[2,3-d]pyrimidin-4-yl)piperazine-1-carboxyl ate (Int 9f)

To a solution of (S)-(1-methylpyrrolidin-2-yl)methanol (319 mg, 2.77 mmol) in THF (5.0 mL) was added sodium tert-butoxide (2M in THF) (0.69 mL, 1.39 mmol) at 0° C. under $N_2$ atmosphere. Then tert-butyl (2S)-2-(cyanomethyl)-4-(6-methyl-2-(methylsulfonyl)-7-(naphthalen-1-yl)-6,7-dihydro-5H-pyrano[2,3-d]pyrimidin-4-yl)piperazine-1-carboxylate (Int 9e) (400 mg, 0.692 mmol) in THF (5 mL) was added. The mixture was stirred at 0° C. for 0.5 h. The reaction mixture was quenched with water (15 mL) and extracted with EtOAc (15 mL×3). The combined organic phases were washed with brine (40 mL), dried over anhydrous $Na_2SO_4$, filtered and concentrated under reduced pressure. The crude was purified by flash silica gel chromatography (eluent of 15% MeOH/DCM) to yield racemic product. MS (ESI): $[M+H]^+$ m/z: 613. The racemate was separated by preparative SFC (Column E, 40% iso-propanol (0.05% DEA) in $CO_2$) to yield tert-butyl (2S)-2-(cyanomethyl)-4-(6-methyl-2-(((S)-1-methylpyrrolidin-2-yl)methoxy)-7-(naphthalen-1-yl)-6,7-dihydro-5H-pyrano[2,3-d]pyrimidin-4-yl)piperazine-1-carboxylate, Peak 1 (Int 9fa) and Peak 2 (Int 9fb).

Step G: 2-((2S)-4-(6-Methyl-2-(((S)-1-methylpyrrolidin-2-yl)methoxy)-7-(naphthalen-1-yl)-6,7-dihydro-5H-pyrano[2,3-d]pyrimidin-4-yl)piperazin-2-yl)acetonitrile (Int 9ga)

A mixture of tert-butyl (2S)-2-(cyanomethyl)-4-(6-methyl-2-(((S)-1-methylpyrrolidin-2-yl)methoxy)-7-(naphthalen-1-yl)-6,7-dihydro-5H-pyrano[2,3-d]pyrimidin-4-yl)piperazine-1-carboxylate (Int 9fa) (25 mg, 0.041 mmol) in TFA (0.2 mL) and DCM (1 mL) was stirred at 20° C. for 0.5 h to give a yellow mixture. The mixture was concentrated to give crude 2-((2S)-4-(6-methyl-2-(((S)-1-methylpyrrolidin-2-yl)methoxy)-7-(naphthalen-1-yl)-6,7-dihydro-5H-pyrano[2,3-d]pyrimidin-4-yl)piperazin-2-yl)acetonitrile, TFA (Int 9ga). The solid was used directly without further purification. MS (ESI): $[M+H]^+$ m/z: 513.

Step H: 2-((2S)-1-Acryloyl-4-(6-methyl-2-(((S)-1-methylpyrrolidin-2-yl)methoxy)-7-(naphthalen-1-yl)-6,7-dihydro-5H-pyrano[2,3-d]pyrimidin-4-yl)piperazin-2-yl)acetonitrile (Ex 9a)

To a mixture of 2-((2S)-4-(6-methyl-2-(((S)-1-methylpyrrolidin-2-yl)methoxy)-7-(naphthalen-1-yl)-6,7-dihydro-5H-pyrano[2,3-d]pyrimidin-4-yl)piperazin-2-yl)acetonitrile (Int 9ga) (25 mg, 0.049 mmol) and TEA (0.020 mL, 0.15 mmol) in DCM (0.5 mL) was added acryloyl chloride (6.6 mg, 0.073 mmol). After addition, the mixture was stirred at 0° C. for 0.5 h to give a yellow mixture. The mixture was concentrated and the residue was purified by Prep-HPLC (Column: Agela DuraShell C18 150 mm×25 mm, 5 um; Condition: water (0.05% $NH_3H_2O$+10 mM $NH_4HCO_3$)-ACN; Begin B 38 End B 68; Gradient Time (min) 10; 100% B Hold Time (min) 2; FlowRate (mL/min) 25) to yield 2-((2S)-1-acryloyl-4-(6-methyl-2-(((S)-1-methylpyrrolidin-2-yl)methoxy)-7-(naphthalen-1-yl)-6,7-dihydro-5H-pyrano[2,3-d]pyrimidin-4-yl)piperazin-2-yl)acetonitrile (Ex 9a). MS (ESI): $[M+H]^+$ m/z: 567. $^1$H NMR (400 MHz, $CDCl_3$) δ 7.92-7.87 (m, 1H), 7.84-7.78 (m, 3H), 7.55-7.46 (m, 3H), 6.57 (br d, J=10.8 Hz, 1H), 6.43-6.34 (m, 1H), 6.10 (s, 1H), 5.82 (br d, J=10.5 Hz, 1H), 5.10 (br s, 1H), 4.37 (br dd, J=4.9, 10.5 Hz, 1H), 4.23 (dd, J=6.1, 10.5 Hz, 1H), 4.15-3.79 (m, 3H), 3.40 (br s, 1H), 3.28-3.10 (m, 4H), 2.85-2.66 (m, 3H), 2.48 (s, 3H), 2.47-2.19 (m, 3H), 2.10-2.00 (m, 1H), 1.92-1.77 (m, 3H), 0.68 (d, J=7.1 Hz, 3H).

Example 9b was prepared in a similar manner to Example 9a, using Int 9fb (Peak 2) as an intermediate to ultimately yield 2-((2S)-1-acryloyl-4-(6-methyl-2-(((S)-1-methylpyrrolidin-2-yl)methoxy)-7-(naphthalen-1-yl)-6,7-dihydro-5H-pyrano[2,3-d]pyrimidin-4-yl)piperazin-2-yl)acetonitrile (Ex 9b). MS (ESI): $[M+H]^+$ m/z: 567. $^1$H NMR (400 MHz, $CDCl_3$) δ 7.93-7.75 (m, 4H), 7.56-7.45 (m, 3H), 6.57 (br s, 1H), 6.42-6.33 (m, 1H), 6.11 (s, 1H), 5.81 (br d, J=10.5 Hz, 1H), 5.01 (br s, 1H), 4.43 (br dd, J=5.4, 10.3 Hz, 1H), 4.29-3.79 (m, 3H), 3.76-3.57 (m, 1H), 3.56-2.96 (m, 5H), 2.86-2.69 (m, 3H), 2.52 (s, 3H), 2.48-2.25 (m, 3H), 2.13-2.04 (m, 1H), 2.00-1.81 (m, 3H), 0.67 (d, J=7.1 Hz, 3H).

The examples in the table below were prepared in a similar manner to Ex. 9, using Int J2 as the trans olefin precursor.

| Ex. | Structure | Compound Name | $[M+H]^+$ Found | SFC Conditions (for step F) |
|---|---|---|---|---|
| 10a | 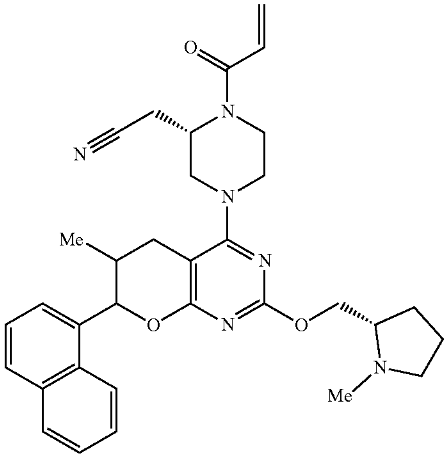 trans isomer Peak 1 | 2-((2S)-1-acryloyl-4-(6-methyl-2-(((S)-1-methylpyrrolidin-2-yl)methoxy)-7-(naphthalen-1-yl)-6,7-dihydro-5H-pyrano[2,3-d]pyrimidin-4-yl)piperazin-2-yl)acetonitrile | 567 | Column D Condition: 0.1% $NH_4OH$/IPA |

-continued

| Ex. | Structure | Compound Name | $[M + H]^+$ Found | SFC Conditions (for step F) |
|---|---|---|---|---|
| 10b | 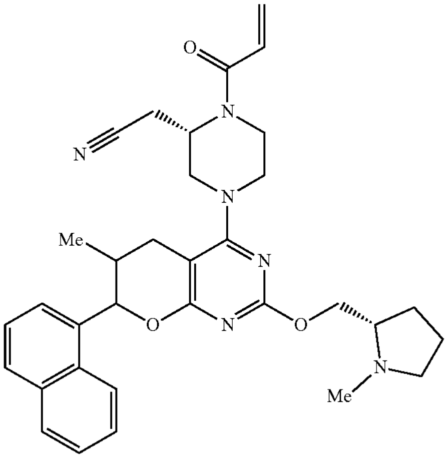 trans isomer Peak 2 | 2-((2S)-1-acryloyl-4-(6-methyl-2-(((S)-1-methylpyrrolidin-2-yl)methoxy)-7-(naphthalen-1-yl)-6,7-dihydro-5H-pyrano[2,3-d]pyrimidin-4-yl)piperazin-2-yl)acetonitrile | 567 | Same conditions as Ex 10a |

Example 11: 4-((S)-4-Acryloyl-3-(cyanomethyl) piperazin-1-yl)-N—((R)-1-(dimethylamino)propan-2-yl)-7-(naphthalen-1-yl)-6,7-dihydro-5H-pyrano[2,3-d]pyrimidine-2-carboxamide

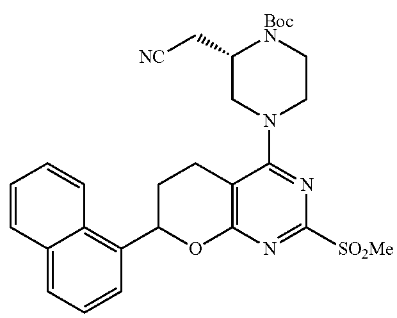

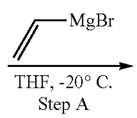

-continued

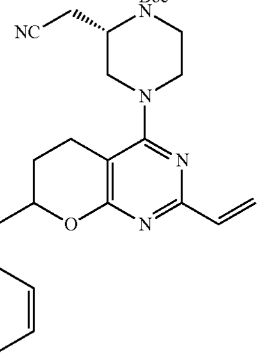

Int 11b

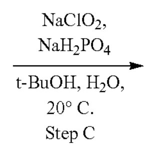

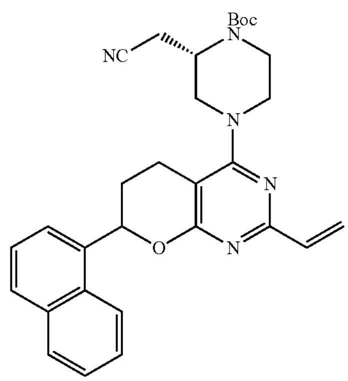

Int 11a

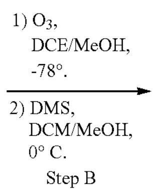

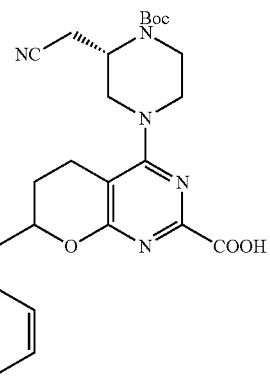

Int 11c

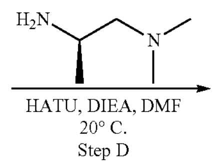

-continued

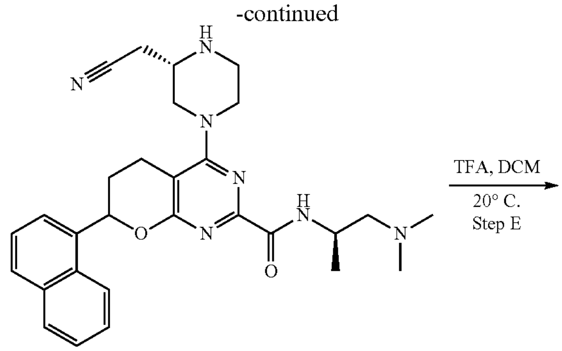

Int 11d

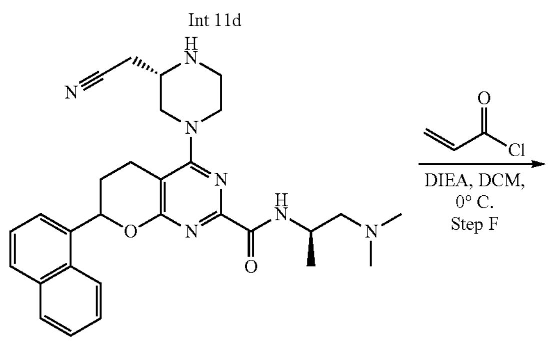

Int 11e

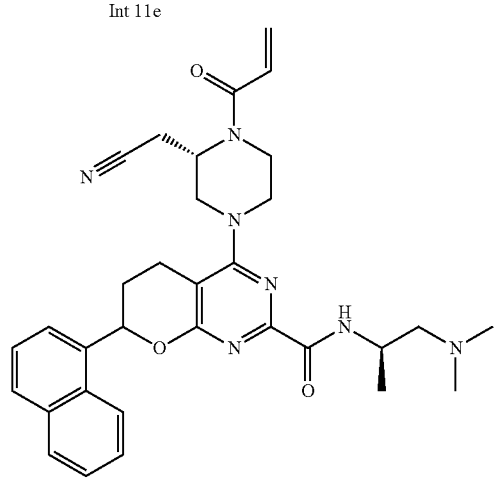

Ex. 11

Step A: (2S)-tert-Butyl 2-(cyanomethyl)-4-(7-(naphthalen-1-yl)-2-vinyl-6,7-dihydro-5H-pyrano[2,3-d]pyrimidin-4-yl)piperazine-1-carboxylate (Int 11a)

To a solution of tert-butyl (2S)-2-(cyanomethyl)-4-(2-(methylsulfonyl)-7-(naphthalen-1-yl)-6,7-dihydro-5H-pyrano[2,3-d]pyrimidin-4-yl)piperazine-1-carboxylate (400 mg, 0.710 mmol) in THF (8 mL) was added vinylmagnesium bromide (0.887 mL, 1.42 mmol, 1.6 M in Me-THF) at −20° C. under $N_2$ atmosphere. The mixture was stirred at −20° C. for 1 h. The mixture was quenched with saturated $NH_4Cl$ solution (15 mL), extracted with ethyl acetate (30 mL), dried over $Na_2SO_4$, filtered and the solvent was evaporated under reduced pressure to give the crude product. The crude product was purified by flash silica gel chromatography (eluent of 0~30% EtOAc/Pet. ether) to give (2S)-tert-butyl 2-(cyanomethyl)-4-(7-(naphthalen-1-yl)-2-vinyl-6,7-dihydro-5H-pyrano[2,3-d]pyrimidin-4-yl)piperazine-1-carboxylate (Int 11a). MS (ESI) $[M+H]^+$ m/z: 512.

Step B: (2S)-tert-Butyl 2-(cyanomethyl)-4-(2-formyl-7-(naphthalen-1-yl)-6,7-dihydro-5H-pyrano[2,3-d]pyrimidin-4-yl)piperazine-1-carboxylate (Int 11b)

An ozone-enriched stream of oxygen was bubbled through a −78° C. solution of (2S)-tert-butyl 2-(cyanomethyl)-4-(7-(naphthalen-1-yl)-2-vinyl-6,7-dihydro-5H-pyrano[2,3-d]pyrimidin-4-yl)piperazine-1-carboxylate (Int 11a) (200 mg, 0.391 mmol) in DCM (10 mL) and MeOH (1 mL) until it turned light blue. The solution was purged with argon for 10 min to remove excess $O_3$. Then the reaction mixture was quenched with DMS (1 mL, 13.52 mmol) and stirred at 0° C. for 0.5 h. 10 mL water was added and the mixture was extracted with EtOAc (10 mL×3). The combined organic phases were washed with brine (10 mL), dried over anhydrous $Na_2SO_4$, filtered and concentrated under reduced pressure to give crude (2S)-tert-butyl 2-(cyanomethyl)-4-(2-formyl-7-(naphthalen-1-yl)-6,7-dihydro-5H-pyrano[2,3-d]pyrimidin-4-yl)piperazine-1-carboxylate (Int 11b). MS (ESI) $[M+H]^+$ m/z: 514.

Step D: 4-((S)-4-(tert-Butoxycarbonyl)-3-(cyanomethyl)piperazin-1-yl)-7-(naphthalen-1-yl)-6,7-dihydro-5H-pyrano[2,3-d]pyrimidine-2-carboxylic acid (Int 11c)

A mixture of (2S)-tert-butyl 2-(cyanomethyl)-4-(2-formyl-7-(naphthalen-1-yl)-6,7-dihydro-5H-pyrano[2,3-d]pyrimidin-4-yl)piperazine-1-carboxylate (Int 11b) (30 mg, 0.058 mmol) and 2-methyl-2-butene (0.124 mL, 1.17 mmol) in t-BuOH (1 mL) was added to a solution of sodium chlorite (15.9 mg, 0.175 mmol) and sodium dihydrogen phosphate (6.5 mg, 0.047 mmol) in water (0.2 mL). After being allowed to stir at 20° C. for 3 h, the reaction mixture was added to aq. KOH (2 M, 2 mL) and extracted with EtOAc (10 mL). The aqueous layer was adjusted to pH 6 by addition of aqueous HCl (0.5 M), and then extracted with EtOAc (10 mL). The organic phases were washed with brine (10 mL), dried over anhydrous $Na_2SO_4$, filtered and concentrated under reduced pressure to afford the crude 4-((S)-4-(tert-butoxycarbonyl)-3-(cyanomethyl)piperazin-1-yl)-7-(naphthalen-1-yl)-6,7-dihydro-5H-pyrano[2,3-d]pyrimidine-2-carboxylic acid (Int 11c). MS (ESI) $[M+H]^+$ m/z: 530.

Step D: (2S)-tert-Butyl 2-(cyanomethyl)-4-(2-(((R)-1-(dimethylamino)propan-2-yl)carbamoyl)-7-(naphthalen-1-yl)-6,7-dihydro-5H-pyrano[2,3-d]pyrimidin-4-yl)piperazine-1-carboxylate (Int 11d)

A mixture of (R)—$N^1$,$N^1$-dimethylpropane-1,2-diamine (15 mg, 0.15 mmol), 44(S)-4-(tert-butoxycarbonyl)-3-(cyanomethyl)piperazin-1-yl)-7-(naphthalen-1-yl)-6,7-dihydro-5H-pyrano[2,3-d]pyrimidine-2-carboxylic acid (Int 11c) (30 mg, 0.057 mmol), HATU (43.1 mg, 0.113 mmol) and DIEA (0.020 mL, 0.11 mmol) in DMF (0.5 mL) was stirred at 20° C. for 1 h. The mixture was dissolved in water (10 mL) and EtOAc (10 mL). The organic layer was separated and the aqueous was re-extracted with EtOAc (10 mL×3), and the combined organic layers were washed with brine (20 mL), dried over anhydrous $Na_2SO_4$, filtered and concentrated under reduced pressure to give crude (2S)-tert-butyl 2-(cyanomethyl)-4-(2-(((R)-1-(dimethylamino)propan-2-yl)carbamoyl)-7-(naphthalen-1-yl)-6,7-dihydro-5H-pyrano[2,3-d]pyrimidin-4-yl)piperazine-1-carboxylate (Int 11d). MS (ESI) $[M+H]^+$ m/z: 614.

Step E: 4-((S)-3-(Cyanomethyl)piperazin-1-yl)-N—((R)-1-(dimethylamino)propan-2-yl)-7-(naphthalen-1-yl)-6,7-dihydro-5H-pyrano[2,3-d]pyrimidine-2-carboxamide (Int 11e)

A mixture of (2S)-tert-butyl 2-(cyanomethyl)-4-(2-(((R)-1-(dimethylamino)propan-2-yl)carbamoyl)-7-(naphthalen-1-yl)-6,7-dihydro-5H-pyrano[2,3-d]pyrimidin-4-yl)piperazine-1-carboxylate (Int 11d) (30 mg, 0.049 mmol) in DCM (1 mL) and TFA (1.9 11.1, 0.024 mmol) was stirred at 15° C. for 0.5 h. The mixture was concentrated in vacuo to give crude 4-((S)-3-(cyanomethyl)piperazin-1-yl)-N—((R)-1-(dimethylamino)propan-2-yl)-7-(naphthalen-1-yl)-6,7-dihydro-5H-pyrano[2,3-d]pyrimidine-2-carboxamide (Int 11e). MS (ESI) $[M+H]^+$ m/z: 514.

Step F: 4-((S)-4-Acryloyl-3-(cyanomethyl)piperazin-1-yl)-N—((R)-1-(dimethyl amino)propan-2-yl)-7-(naphthalen-1-yl)-6,7-dihydro-5H-pyrano[2,3-d]pyrimidine-2-carboxamide (Ex 11)

To a mixture of 44(S)-3-(cyanomethyl)piperazin-1-yl)-N—((R)-1-(dimethylamino)propan-2-yl)-7-(naphthalen-1-yl)-6,7-dihydro-5H-pyrano[2,3-d]pyrimidine-2-carboxamide (Int 11e) (25 mg, mmol) and DIEA (0.026 mL, 0.15 mmol) in DCM (0.5 mL) was added acryloyl chloride (5.3 mg, 0.058 mmol) at 0° C. After addition, the mixture was stirred at 0° C. for 0.5 h. The mixture was concentrated and the residue was purified by Prep-HPLC (Column: Agela DuraShell C18 150 mm×mm, 5 um; Condition: water (0.04% $NH_3H_2O$+10 mM $NH_4HCO_3$)-ACN; Begin B 37 End B 67; Gradient Time (min) 10; 100% B Hold Time (min) 2; FlowRate (mL/min) 25) to give 4-((S)-4-acryloyl-3-(cyanomethyl)piperazin-1-yl)-N—((R)-1-(dimethyl amino)propan-2-yl)-7-(naphthalen-1-yl)-6,7-dihydro-5H-pyrano[2,3-d]pyrimidine-2-carboxamide (Ex. 11) as a racemic mixture. MS (ESI) $[M+H]^+$ m/z: 568. $^1H$ NMR (500 MHz, $CDCl_3$) δ 8.01-7.85 (m, 4H), 7.75-7.64 (m, 1H), 7.59-7.51 (m, 3H), 6.59 (br s, 1H), 6.39 (br d, J=16.6 Hz, 1H), 6.18-6.07 (m, 1H), 5.82 (br d, J=10.4 Hz, 1H), 5.19-4.42 (m, 1H), 4.27 (br s, 2H), 4.06-3.58 (m, 2H), 3.28 (br d, J=9.9 Hz, 1H), 3.22-2.86 (m, 3H), 2.84-2.49 (m, 5H), 2.30 (br s, 6H), 2.26-2.06 (m, 2H), 1.29-1.24 (m, 3H).

Example 12: 242S)-4-(7-(3H-Benzo[e]indazol-9-yl)-2-4(S)-1-methylpyrrolidin-2-yl)methoxy)-6,7-dihydro-5H-pyrano[2,3-d]pyrimidin-4-yl)-1-acryloylpiperazin-2-yl)acetonitrile

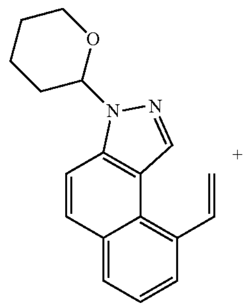

Int K5

+

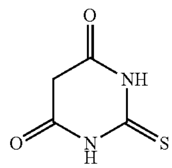

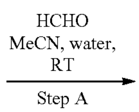

-continued

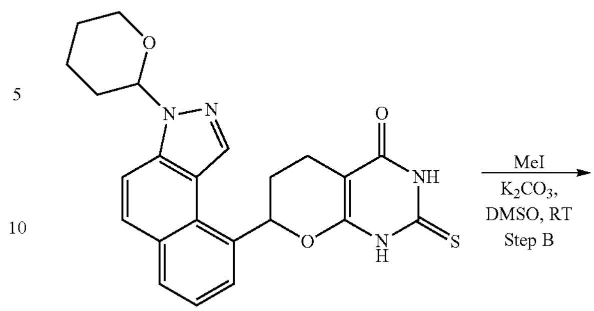

Int 12a

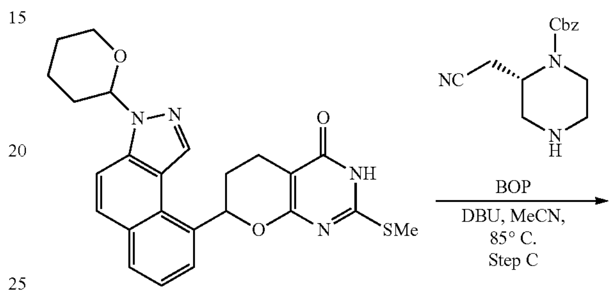

Int 12b

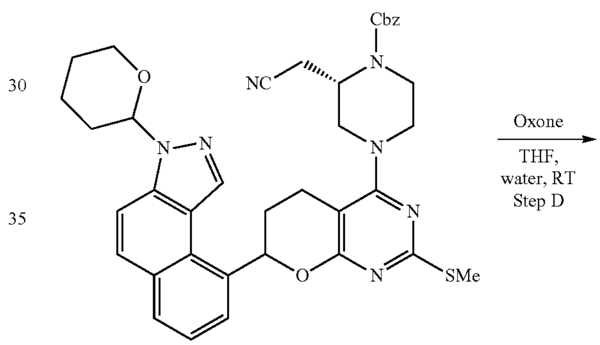

Int 12c

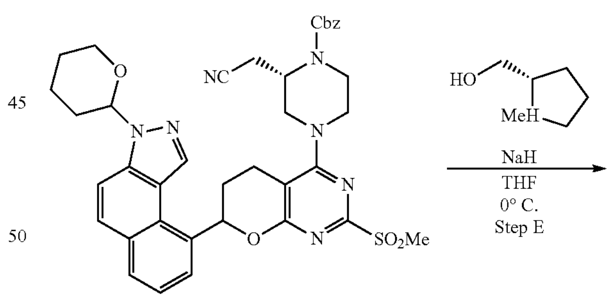

Int 12d

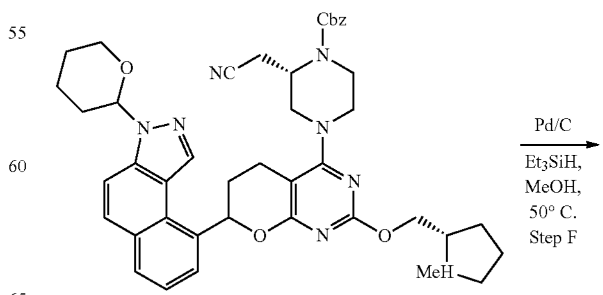

Int 12e

-continued

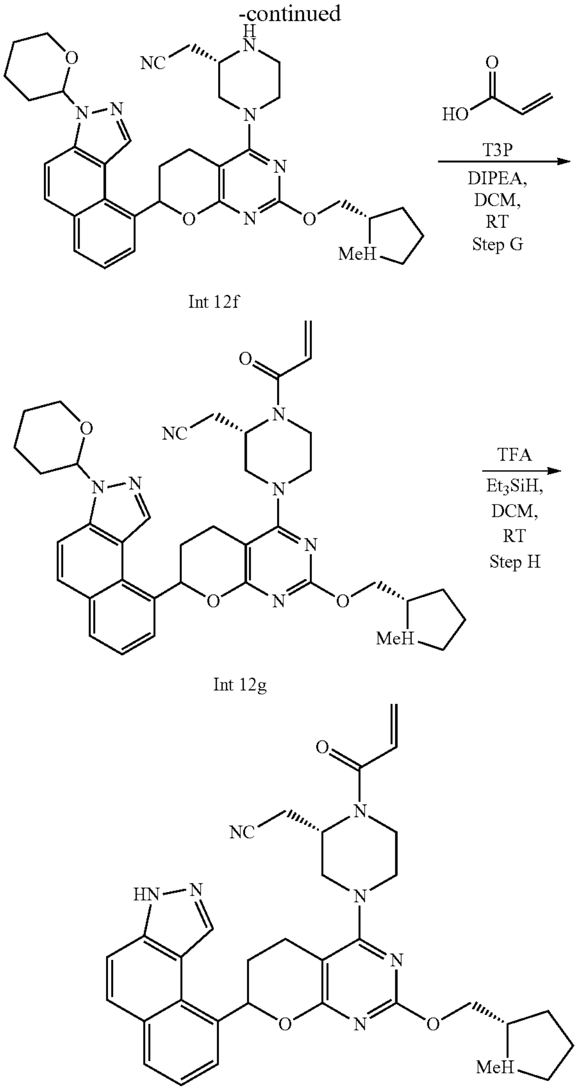

Int 12f

Int 12g

Ex. 12

Step A: 7-(3-(Tetrahydro-2H-pyran-2-yl)-3H-benzo[e]indazol-9-yl)-2-thioxo-1,2,3,5,6,7-hexahydro-4H-pyrano[2,3-d]pyrimidin-4-one (Int 12a)

2-Thioxodihydropyrimidine-4,6(1H,5H)-dione (168 mg, 1.16 mmol) was added to a suspension of 3-(tetrahydro-2H-pyran-2-yl)-9-vinyl-3H-benzo[e]indazole (Int K5) (216 mg, 0.776 mmol) and HCHO (37% in water, 0.12 mL, 1.6 mmol) in water (1.56 mL) and MeCN (1.56 mL). The reaction stirred vigorously at room temperature for 16 h. The reaction was diluted with MeCN (5 mL) and lyophilized overnight to provide 7-(3-(tetrahydro-2H-pyran-2-yl)-3H-benzo[e]indazol-9-yl)-2-thioxo-1,2,3,5,6,7-hexahydro-4H-pyrano[2,3-d]pyrimidin-4-one (Int 12a), which was used in the subsequent step without further purification. MS (ESI) $[M+H]^+$ m/z: 435.

Step B: 2-(Methylthio)-7-(3-(tetrahydro-2H-pyran-2-yl)-3H-benzo[e]indazol-9-yl)-3,5,6,7-tetrahydro-4H-pyrano[2,3-d]pyrimidin-4-one (Int 12b)

DMSO (2.59 mL) was added to a mixture of 7-(3-(tetrahydro-2H-pyran-2-yl)-3H-benzo[e]indazol-9-yl)-2-thioxo-1,2,3,5,6,7-hexahydro-4H-pyrano[2,3-d]pyrimidin-4-one (Int 12a) (337 mg, 0.776 mmol) and $K_2CO_3$ (118 mg, 0.853 mmol). The reaction stirred vigorously at room temperature for 45 min. MeI (51 μL, 0.82 mmol) was added, and the reaction stirred vigorously at room temperature for 15 min. The reaction was diluted with water (10 mL), filtered, and washed with water (3×5 mL) and ether (3×5 mL). The resulting solid was dried under reduced pressure to provide 2-(methylthio)-7-(3-(tetrahydro-2H-pyran-2-yl)-3H-benzo[e]indazol-9-yl)-3,5,6,7-tetrahydro-4H-pyrano[2,3-d]pyrimidin-4-one (Int 12b), which was used in the subsequent step without further purification. MS (ESI) $[M+H]^+$ m/z: 449.

Step C: Benzyl (2S)-2-(cyanomethyl)-4-(2-(methylthio)-7-(3-(tetrahydro-2H-pyran-2-yl)-3H-benzo[e]indazol-9-yl)-6,7-dihydro-5H-pyrano[2,3-d]pyrimidin-4-yl)piperazine-1-carboxylate (Int 12c)

DBU (0.200 mL, 1.34 mmol) was added to a suspension of 2-(methylthio)-7-(3-(tetrahydro-2H-pyran-2-yl)-3H-benzo[e]indazol-9-yl)-3,5,6,7-tetrahydro-4H-pyrano[2,3-d]pyrimidin-4-one (Int 12b) (0.200 g, 0.446 mmol), BOP (256 mg, 0.580 mmol) and benzyl (S)-2-(cyanomethyl)piperazine-1-carboxylate (231 mg, 0.892 mmol) in MeCN (1.78 mL). The reaction stirred vigorously at 85° C. for 16 h. The reaction was cooled to room temperature, diluted with water (10 mL), and extracted with EtOAc (3×10 mL). The combined organic layers were dried over anhydrous $MgSO_4$, filtered, and concentrated under reduced pressure. The crude residue was purified by silica gel chromatography (gradient elution: 0-75% EtOAc/Hexanes) to provide benzyl (2S)-2-(cyanomethyl)-4-(2-(methylthio)-7-(3-(tetrahydro-2H-pyran-2-yl)-3H-benzo[e]indazol-9-yl)-6,7-dihydro-5H-pyrano[2,3-d]pyrimidin-4-yl)piperazine-1-carboxylate (Int 12c). MS (ESI) $[M+H]^+$ m/z: 690.

Step D: Benzyl (2S)-2-(cyanomethyl)-4-(2-(methylsulfonyl)-7-(3-(tetrahydro-2H-pyran-2-yl)-3H-benzo[e]indazol-9-yl)-6,7-dihydro-5H-pyrano[2,3-d]pyrimidin-4-yl)piperazine-1-carboxylate (Int 12d)

Oxone (179 mg, 0.291 mmol) was added to a solution of benzyl (2S)-2-(cyanomethyl)-4-(2-(methylthio)-7-(3-(tetrahydro-2H-pyran-2-yl)-3H-benzo[e]indazol-9-yl)-6,7-dihydro-5H-pyrano[2,3-d]pyrimidin-4-yl)piperazine-1-carboxylate (Int 12c) (67 mg, 0.097 mmol) in THF (0.97 mL) and water (0.97 mL). The reaction was stirred vigorously at room temperature for 16 h. The reaction was diluted with water (10 mL) and extracted with 3:1 $CHCl_3$/IPA (3×10 mL). The combined organic layers were dried over anhydrous $MgSO_4$, filtered, and concentrated under reduced pressure to provide benzyl (2S)-2-(cyanomethyl)-4-(2-(methylsulfonyl)-7-(3-(tetrahydro-2H-pyran-2-yl)-3H-benzo[e]indazol-9-yl)-6,7-dihydro-5H-pyrano[2,3-d]pyrimidin-4-yl)piperazine-1-carboxylate (Int 12d), which was used in the next step without further purification. MS (ESI) $[M+H]^+$ m/z: 722.

Step E: Benzyl (2S)-2-(cyanomethyl)-4-(2-(((S)-1-methylpyrrolidin-2-yl)methoxy)-7-(3-(tetrahydro-2H-pyran-2-yl)-3H-benzo[e]indazol-9-yl)-6,7-dihydro-5H-pyrano[2,3-d]pyrimidin-4-yl)piperazine-1-carboxylate (Int 12e)

NaH (60 wt % in mineral oil, 19.4 mg, 0.485 mmol) was added to a solution of (S)-(1-methylpyrrolidin-2-yl)methanol (13 μL, 0.11 mmol) in THF (0.65 mL) at 0° C. The reaction was stirred vigorously at 0° C. for 30 min. A solution of benzyl (2S)-2-(cyanomethyl)-4-(2-(methylsulfonyl)-7-(3-(tetrahydro-2H-pyran-2-yl)-3H-benzo[e]indazol-9-yl)-6,7-dihydro-5H-pyrano[2,3-d]pyrimidin-4-yl)piperazine-1-carboxylate (Int 12d) (70 mg, 0.097 mmol) in THF (1.3 mL) was added at 0° C., and the reaction was stirred vigorously at 0° C. for 2 h. The reaction was diluted with water (10 mL) and extracted with EtOAc (3×10 mL). The combined organic layers were dried over anhydrous $MgSO_4$, filtered, and concentrated under reduced pressure to provide benzyl (2S)-2-(cyanomethyl)-4-(2-(((S)-1-methylpyrrolidin-2-yl)methoxy)-7-(3-(tetrahydro-2H-pyran-2-yl)-3H-benzo[e]indazol-9-yl)-6,7-dihydro-5H-pyrano[2,3-d]pyrimidin-4-yl)piperazine-1-carboxylate (Int 12e), which was used in the next step without further purification. MS (ESI) $[M+H]^+$ m/z: 757.

Step F: 2-((2S)-4-(2-(((S)-1-Methylpyrrolidin-2-yl)methoxy)-7-(3-(tetrahydro-2H-pyran-2-yl)-3H-benzo[e]indazol-9-yl)-6,7-dihydro-5H-pyrano[2,3-d]pyrimidin-4-yl)piperazin-2-yl)acetonitrile (Int 12f)

Pd/C (10 wt %, 30 mg, 0.28 mmol) was added to a solution of benzyl (2S)-2-(cyanomethyl)-4-(2-(((S)-1-methylpyrrolidin-2-yl)methoxy)-7-(3-(tetrahydro-2H-pyran-2-yl)-3H-benzo[e]indazol-9-yl)-6,7-dihydro-5H-pyrano[2,3-d]pyrimidin-4-yl)piperazine-1-carboxylate (74 mg, 0.098 mmol) (Int 12e) in MeOH (0.98 mL) The reaction stirred vigorously at 50° C. for 16 h under an atmosphere of $H_2$. The reaction was cooled to room temperature, filtered through Celite®, and washed with MeOH (3×5 mL). The resulting filtrate was concentrated under reduced pressure to provide 2-((2S)-4-(2-(((S)-1-methylpyrrolidin-2-yl)methoxy)-7-(3-(tetrahydro-2H-pyran-2-yl)-3H-benzo[e]indazol-9-yl)-6,7-dihydro-5H-pyrano[2,3-d]pyrimidin-4-yl)piperazin-2-yl)acetonitrile (Int 12f), which was used in the subsequent step without further purification. MS (ESI) $[M+H]^+$ m/z: 623.

Step G: 2-((2S)-1-Acryloyl-4-(2-4(S)-1-methylpyrrolidin-2-yl)methoxy)-7-(3-(tetrahydro-2H-pyran-2-yl)-3H-benzo[e]indazol-9-yl)-6,7-dihydro-5H-pyrano[2,3-d]pyrimidin-4-yl)piperazin-2-yl)acetonitrile (Int 12g)

T3P® (50% weight in EtOAc, 58 μL, 0.20 mmol) was added to a solution of 2-((2S)-4-(2-(((S)-1-methylpyrrolidin-2-yl)methoxy)-7-(3-(tetrahydro-2H-pyran-2-yl)-3H-benzo[e]indazol-9-yl)-6,7-dihydro-5H-pyrano[2,3-d]pyrimidin-4-yl)piperazin-2-yl)acetonitrile (61 mg, 0.098 mmol) (Int 12f, acrylic acid (7.4 μL, 0.11 mmol), and DIPEA (51 μL, 0.30 mmol) in DCM (0.98 mL). The reaction stirred vigorously at room temperature for 30 min. The reaction was quenched with 1 N HCl (0.49 mL), diluted with water (10 mL) and extracted with 3:1 $CHCl_3$/IPA (3×10 mL). The combined organic layers were dried over anhydrous $MgSO_4$, filtered, and concentrated under reduced pressure to provide 2-((2S)-1-acryloyl-4-(2-(((S)-1-methylpyrrolidin-2-yl)methoxy)-7-(3-(tetrahydro-2H-pyran-2-yl)-3H-benzo[e]indazol-9-yl)-6,7-dihydro-5H-pyrano[2,3-d]pyrimidin-4-yl)piperazin-2-yl)acetonitrile (Int 12g), which was used in the subsequent step without further purification. MS (ESI) $[M+H]^+$ m/z: 677.

Step H: 2-42S)-4-(7-(3H-Benzo[e]indazol-9-yl)-2-(((S)-1-methylpyrrolidin-2-yl)methoxy)-6,7-dihydro-5H-pyrano[2,3-d]pyrimidin-4-yl)-1-acryloylpiperazin-2-yl)acetonitrile (Ex. 12)

TFA (76 μL, 0.99 mmol) was added to a solution of 2-((2S)-1-acryloyl-4-(2-(((S)-1-methylpyrrolidin-2-yl)methoxy)-7-(3-(tetrahydro-2H-pyran-2-yl)-3H-benzo[e]indazol-9-yl)-6,7-dihydro-5H-pyrano[2,3-d]pyrimidin-4-yl)piperazin-2-yl)acetonitrile (Int 12g) (66 mg, 0.098 mmol)) and $Et_3SiH$ (39 μL, 0.25 mmol) in DCM (0.98 mL). The reaction was stirred vigorously at room temperature for 1 h. The reaction was concentrated under reduced pressure and the crude residue was purified by reversed-phase HPLC to provide 2-((2S)-4-(7-(3H-benzo[e]indazol-9-yl)-2-(((S)-1-methylpyrrolidin-2-yl)methoxy)-6,7-dihydro-5H-pyrano[2,3-d]pyrimidin-4-yl)-1-acryloylpiperazin-2-yl)acetonitrile (Ex. 12) as a racemic mixture. MS (ESI): $[M+H]^+$ m/z: 593; $^1$H NMR (600 MHz, DMSO-$d_6$) δ 13.62 (s, 1H), 8.36 (s, 1H), 8.05 (s, 1H), 7.87 (dd, J=33.6, 7.2 Hz, 1H), 7.75 (d, J=8.9 Hz, 1H), 7.67-7.53 (m, 1H), 6.86 (s, 1H), 6.30 (dd, J=22.3, 9.3 Hz, 1H), 6.20 (dd, J=16.6, 2.1 Hz, 1H), 5.79 (dd, J=10.5, 2.0 Hz, 1H), 4.99 (app br s, 1H), 4.78 (app br s, 1H), 4.44 (app br s, 1H), 4.29-4.15 (m, 1H), 4.13-3.99 (m, 2H), 3.95-3.80 (m, 1H), 3.70-3.60 (m, 1H), 3.28-3.13 (m, 2H), 3.10-2.97 (m, 2H), 2.95 (dt, J=9.2, 4.5 Hz, 1H), 2.82 (app br s, 1H), 2.72 (app br s, 1H), 2.34 (s, 3H), 2.17 (q, J=8.8 Hz, 1H), 2.00-1.86 (m, 2H), 1.72-1.63 (m, 2H), 1.63-1.50 (m, 1H).

BIOLOGICAL ASSAYS

Procedure for SOS-Catalyzed Nucleotide Exchange Assay

The SOS-catalyzed nucleotide exchange assay utilizes a preformed complex of recombinant biotinylated KRAS protein containing G12C/C51S/C80L/C118S mutations (183 amino acids; biotin on K10; leader sequence which is an AviTag; referred to as SEQ ID NO: 1 or "Biotinylated KRAS G12C protein" hereafter), Bodipy-GDP, and Terbium-streptavidin. Compounds are added to this complex and then after 60 minutes, the mixture is treated with recombinant SOS protein and unlabeled GTP. Small molecule inhibitors stabilize the Bodipy-GDP complex whereas the untreated protein rapidly exchanges Bodipy-GDP for unlabeled GTP resulting in reduced TR-FRET signal.

Biotinylated KRAS G12C protein (SEQ ID NO: 1) is diluted to 2 μM in an EDTA buffer (20 mM HEPES, 150 mM sodium chloride, 10 mM EDTA, and 0.01% Tween) and incubated at room temperature for one hour. This mixture is then further diluted to 90 nM in an assay buffer (20 mM HEPES, 150 mM sodium chloride, 10 mM magnesium chloride, and 0.005% Tween) containing 15 nM of Terbium-Streptavidin (Invitrogen, catalog #PV3577) and 900 nM of Bodipy-GDP and incubated at room temperature for six hours. This solution is referred to as Biotinylated KRAS G12C mixture.

Each test compound (10 mM stock in DMSO) is diluted in DMSO to make a 10-point, 3-fold dilution series in a 384-well low dead volume microplate (Labcyte, catalog #LP-0200). Once titrations are made, 10 nL of the diluted compounds is acoustically dispensed into a 384-well plate (Corning, catalog #3820) using an Echo 550 (Labcyte).

Each well of the plate receives 3 μL Biotinylated KRAS G12C mixture that had been incubating for six hours and 3 μL of assay buffer using a BioRAPTR (Beckman Coulter) and is incubated at room temperature for 60 minutes. Each well then receives 3 μL of 240 nM recombinant human SOS protein and 9 mM GTP (Sigma, G8877) in assay buffer and is incubated at room temperature for 60 minutes.

The time-resolved fluorescence resonance energy transfer signal of the plate is measured on an Envision (PerkinElmer) plate reader: Excitation filter=340 nm; emission1=495 nm;

emission2=520 nm; dichroic mirror=D400/D505; delay time=100 μs. The signal of each well is determined as the ratio of the emission at 520 nm to that at 495 nm. Percent effect of each well is determined after normalization to control wells containing DMSO (no effect) or a saturating concentration of inhibitor (max effect). The apparent effect as a function of compound concentration is fit to a four parameter logistic equation.

Procedure for Cellular Phospho-ERK Assay

NCI-H358 cells (ATCC® CRL-5807™) were cultured in T150 flask in growth medium (RPMI medium 1640-GlutaMAX™—I (ThermoFisher Scientific 61870) containing 10% fetal bovine serum (ThermoFisher Scientific 10091148)). The cells were harvested in growth medium after TrypLE (ThermoFisher scientific 12604021) digestion and were seeded in 384-well collagen coated cell culture plate (Corning 356702) at a density of 15,000 cells/well, and incubated at 37° C., 5% $CO_2$ overnight. The compound dose-response titrations were prepared and appropriate amounts of compounds were dispensed in a 384-well intermediate plate using an Echo 550 liquid handler. RPMI medium 1640-GluiaMAX™—I were added to the intermediate plate and transferred to 384-well cell culture plate, which was incubated at 37° C., 5% $CO_2$ for 2 hours. After removal of medium from the plate, cells were lysed in lysis buffer from Alpha SureFire® Ultra™ Multiplex p-Erk and total Erk assay kit (PerkinElmer MPSU-PIERK) containing Halt™ Protease and Phosphotase inhibitor cocktail (ThermoFisher Scientific 78446) at room temperature with constant shaking at 300 rpm for 30 minutes. The cell lysates were then transferred to OptiPlate-384 plate (PerkinElmer 6005620) and the phosphorylation of Erk and total Erk levels were detected by Alpha SureFire Ultra Multiplex p-Erk kit (PerkinElmer MPSU-PIERK) following the manufacturer's protocol. Assay plates were read on an EnVision Multimode Plate Reader (PerkinElmer), and the ratio of p-Erk vs total Erk in each well was used as the final readout. Dose response curves were analyzed using a 4-parameter logistic model to calculate $IC_{50}$ values using spotfire software.

TABLE 1

In vitro apparent potency ($IC_{50}$) in the SOS-catalyzed nucleotide exchange assay with a preincubation time of 60 minutes prior to addition of SOS. In vitro potency in the cellular phospho-ERK assay after 2 hour incubation.

| Compound | $IC_{50}$ (nM) at 60 min (SOS) | $IC_{50}$ (nM) pERK (Cell) |
|---|---|---|
| 1a | 11.41 | 578.5 |
| 1b | 395 | 9021 |
| 2 | 17.5 | 500.8 |
| 3 | 792.5 | 15720 |
| 4a | 104.4 | 19250 |
| 4b | 2690 | 30000 |
| 5a | 88.6 | 6354 |
| 5b | 195 | 10270 |
| 6 | 631.9 | 24060 |
| 7a | 13.8 | 394 |
| 7b | 84.8 | 2376 |
| 8a | 817 | 26240 |
| 9a | 259.2 | 13230 |
| 9b | 2129 | 21330 |
| 10a | 12.87 | 704 |
| 10b | 153.3 | 5228 |
| 11 | 1413 | 21690 |
| 12 | 87.1 | 18480 |

Protein Sequence

Biotinylated KRAS G12C Protein

```
                                    (SEQ ID NO: 1)
GLNDIFEAQKIEWHETEYKLVVVGACGVGKSALTIQLIQNHFVD

EYDPTIEDSYRKQVVIDGETSLLDILDTAGQEEYSAMRDQYMRT

GEGFLLVFAINNTKSFEDIHHYREQIKRVKDSEDVPMVLVGNKS

DLPSRTVDTKQAQDLARSYGIPFIETSAKTRQGVDDAFYTLVRE

IRKHKEK
```

We claim:

1. A compound of the Formula (I)

(I)

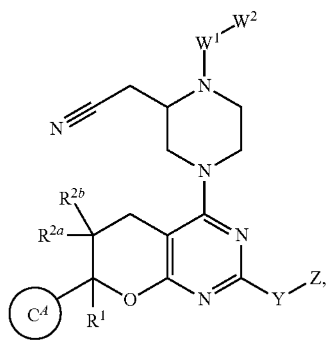

wherein:

ring $C^A$ is (i) naphthyl;

(ii) phenyl;

(iii) a bicyclic 9- or 10-membered heteroaryl containing 1 to 3 ring atoms selected from N, O, or S; or (iv) a tricyclic 13- or 14-membered heteroaryl containing 1 to 3 ring atoms selected from N, O, or S;

wherein ring $C^A$ is unsubstituted or substituted by 1 to 4 $R^{CA}$ substituents which are halo, $C_1$-$C_3$ alkyl, $C_1$-$C_3$ fluoroalkyl, $C_1$-$C_3$ alkoxy, hydroxy or cyano;

$R^1$ is H or $C_1$-$C_3$ alkyl;

$R^{2a}$ and $R^{2b}$ are independently H, F, $C_1$-$C_3$ alkyl, or $C_1$-$C_3$ fluoroalkyl;

$W^1$ is —C(O)— or —$S(O)_2$—;

$W^2$ is a group of the formula:

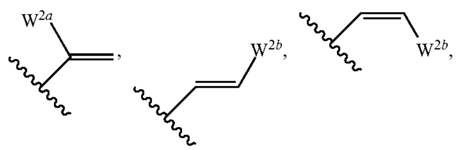

-continued

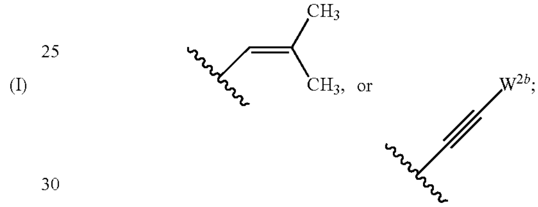

wherein $W^{2a}$ is H, $CH_3$, F, cyano, $CH_2OH$, $CH_2CH_2OH$, or $CH_2Br$;

$W^{2b}$ is $CH_3$, $CH_2NH_2$, $CH_2N(H)$ $CH_3$, $CH_2N(CH_3)_2$, $CH_2$—NH-cyclopropyl,

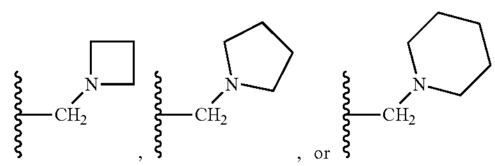

Y is —$O(C(R^y)$ $2)_m$— or —C(O)—N(H)—$(C(R^y)_2)_m$—;

each $R^y$ is independently H or $C_1$-$C_3$ alkyl, or alternatively two $R^y$ together with the carbon atom to which they are attached form a cyclopropyl, cyclobutyl, cyclopentyl or cyclohexyl ring;

the subscript m is 1, 2, or 3;

Z is (a)

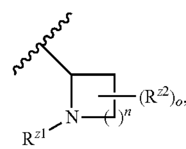

wherein $R^{z1}$ is $C_1$-$C_3$ alkyl;

each $R^{z2}$ is independently fluoro or $C_1$-$C_3$ alkyl;

the subscript n is 1, 2, or 3;

the subscript o is 0, 1, or 2; or (b) —$N(R^{z3})_2$, wherein each $R^{z3}$ is independently H or $C_1$-$C_3$ alkyl; or alternatively, two $R^{z3}$, together with the nitrogen atom to which they are attached, form an aziridinyl, azetidinyl, pyrrolidinyl, piperidinyl, or azepinyl ring, or a pharmaceutically acceptable salt thereof.

2. The compound of claim 1 or the pharmaceutically acceptable salt thereof, wherein the group —$W^1$-$W^2$ is —C(O)—C(H)=$CH_2$.

3. The compound of claim 1 or the pharmaceutically acceptable salt thereof, wherein ring $C^A$ is unsubstituted or substituted naphthyl, phenyl, indazolyl, or benzo[e]indazolyl.

4. The compound of claim 3 or the pharmaceutically acceptable salt thereof, wherein ring $C^A$ is

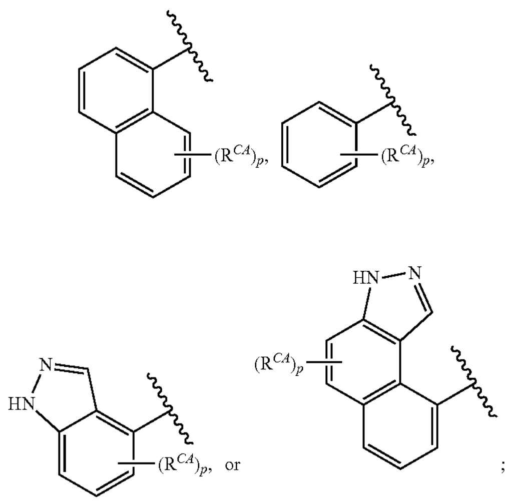

and the subscript p is 0, 1, or 2.

5. The compound of claim 1 or the pharmaceutically acceptable salt thereof, wherein Y is —$OC(R^y)_2$—.

6. The compound of claim 5 or the pharmaceutically acceptable salt thereof, wherein Z is

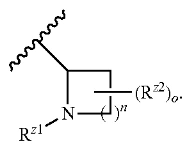

7. The compound of claim 6 or the pharmaceutically acceptable salt thereof, wherein the subscript n is 2.

8. The compound of claim 1 or the pharmaceutically acceptable salt thereof, wherein Y is —C(O)—N(H)—$(C(R^y)_2)_m$—.

9. The compound of claim 8 or the pharmaceutically acceptable salt thereof, wherein Z is —$N(R^{z3})_2$.

10. The compound of claim 9 or the pharmaceutically acceptable salt thereof, wherein —Y—Z is

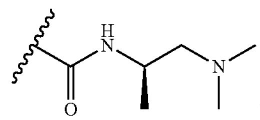

11. The compound of claim 1 or the pharmaceutically acceptable salt thereof, wherein $R^1$ is H or methyl.

12. The compound of claim 1 or the pharmaceutically acceptable salt thereof, wherein $R^{2a}$ and $R^{2b}$ are independently H, F, or methyl.

13. The compound of claim 1 which is:

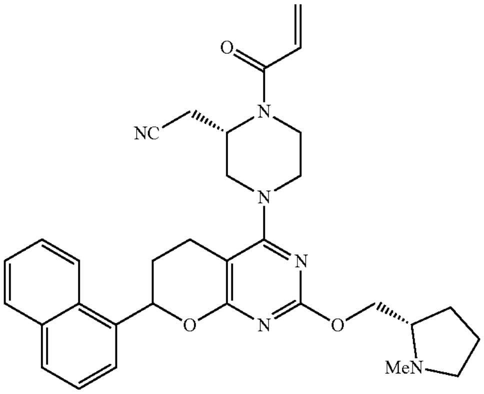

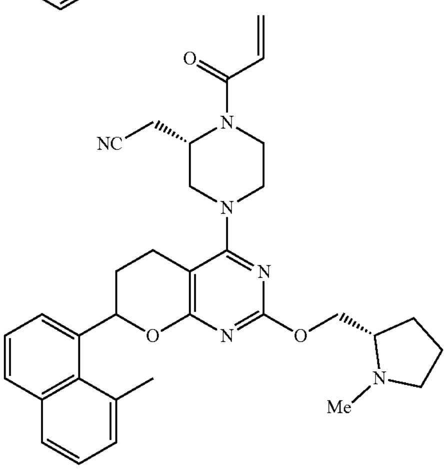

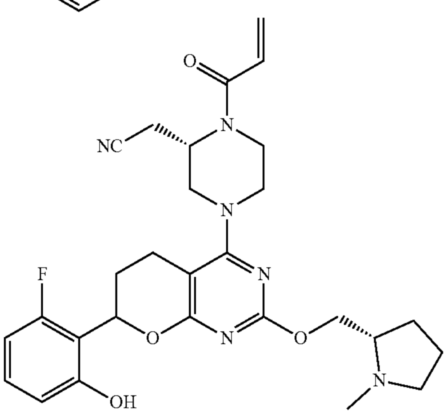

-continued
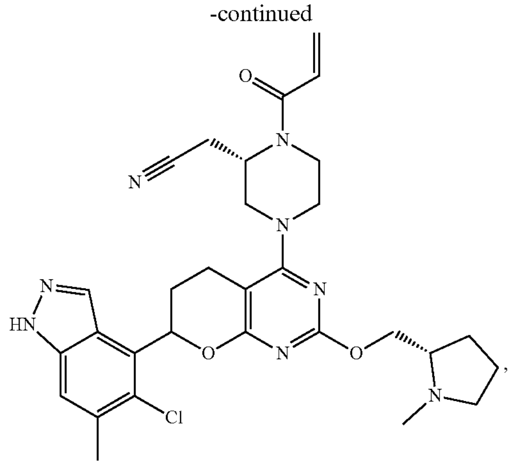
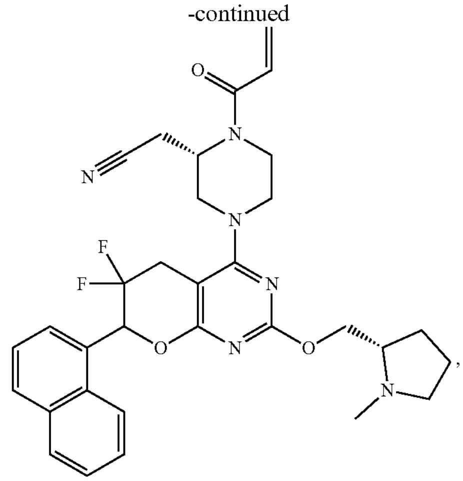
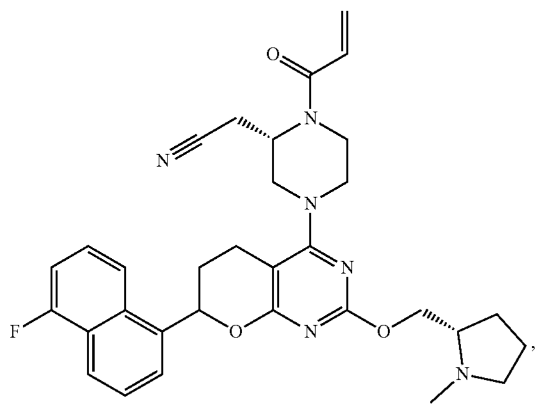
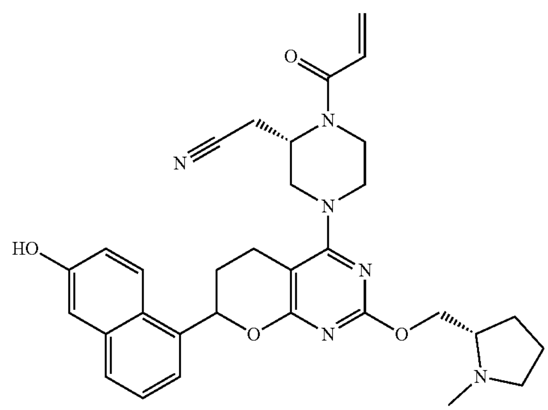
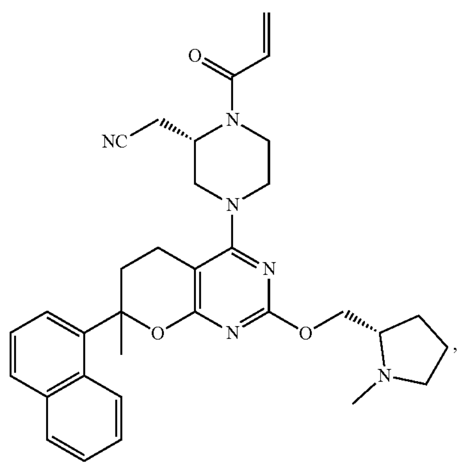
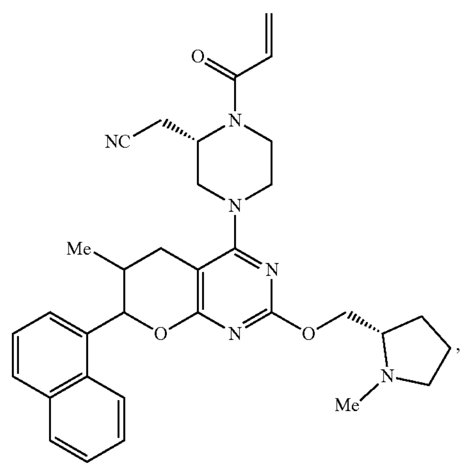

-continued

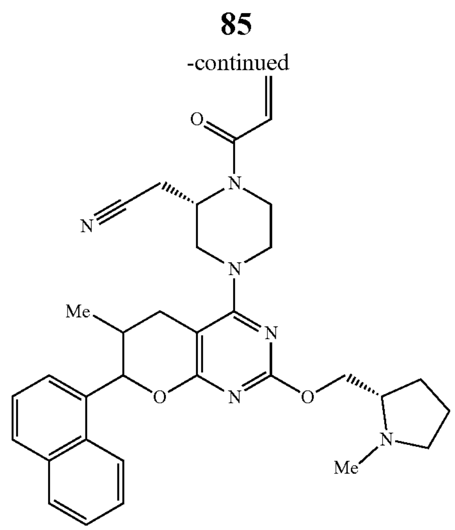

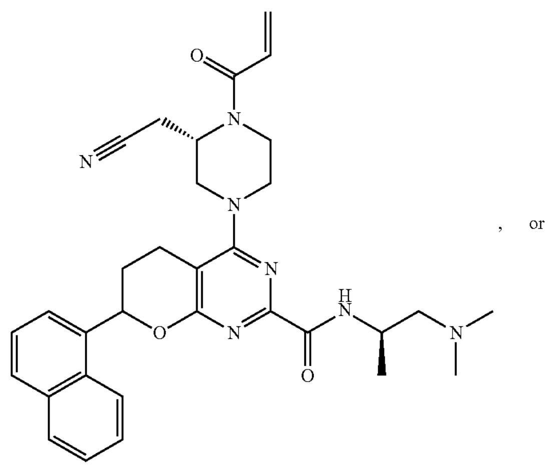

, or

-continued

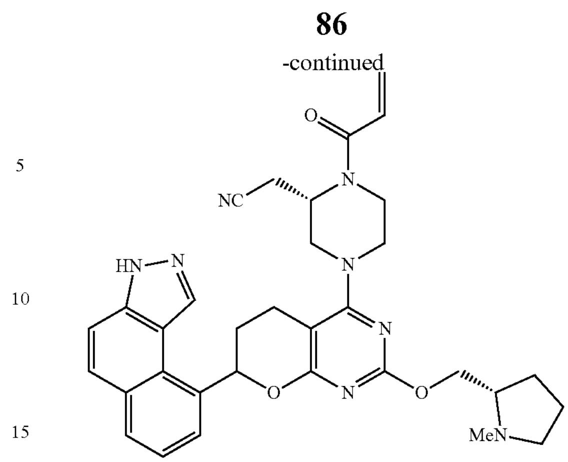

or the pharmaceutically acceptable salt thereof.

14. A pharmaceutical composition comprising the compound of claim 1 or the pharmaceutically acceptable salt thereof, and a pharmaceutically acceptable carrier.

15. A method of inhibiting KRAS G12C protein comprising contacting KRAS G12C protein with the compound of claim 1, or the pharmaceutically acceptable salt thereof, to inhibit the activity of the KRAS G12C protein.

16. A method of treating cancer comprising administering a therapeutically effective amount of the compound of claim 1, or the pharmaceutically acceptable salt thereof, to a subject in need of such treatment, wherein the cancer comprises a KRAS G12C mutation.

17. The method of claim 16, further comprising administering an additional active agent to the subject, wherein the additional active agent is an anti-cancer agent.

18. The pharmaceutical composition of claim 14, wherein the pharmaceutical composition further comprises an additional active agent, wherein the additional active agent is an anti-cancer agent.

* * * * *

SEQUENCE LISTING

```
<160> NUMBER OF SEQ ID NOS: 1

<210> SEQ ID NO 1
<211> LENGTH: 183
<212> TYPE: PRT
<213> ORGANISM: Artificial
<220> FEATURE:
<223> OTHER INFORMATION: Synthetic Protein
<220> FEATURE:
<221> NAME/KEY: biotin
<222> LOCATION: (10)..(10)

<400> SEQUENCE: 1

Gly Leu Asn Asp Ile Phe Glu Ala Gln Lys Ile Glu Trp His Glu Thr
1               5                   10                  15

Glu Tyr Lys Leu Val Val Val Gly Ala Cys Gly Val Gly Lys Ser Ala
            20                  25                  30

Leu Thr Ile Gln Leu Ile Gln Asn His Phe Val Asp Glu Tyr Asp Pro
        35                  40                  45

Thr Ile Glu Asp Ser Tyr Arg Lys Gln Val Val Ile Asp Gly Glu Thr
    50                  55                  60

Ser Leu Leu Asp Ile Leu Asp Thr Ala Gly Gln Glu Glu Tyr Ser Ala
65                  70                  75                  80
```

-continued

```
Met Arg Asp Gln Tyr Met Arg Thr Gly Glu Gly Phe Leu Leu Val Phe
                85                  90                  95

Ala Ile Asn Asn Thr Lys Ser Phe Glu Asp Ile His His Tyr Arg Glu
            100                 105                 110

Gln Ile Lys Arg Val Lys Asp Ser Glu Asp Val Pro Met Val Leu Val
        115                 120                 125

Gly Asn Lys Ser Asp Leu Pro Ser Arg Thr Val Asp Thr Lys Gln Ala
    130                 135                 140

Gln Asp Leu Ala Arg Ser Tyr Gly Ile Pro Phe Ile Glu Thr Ser Ala
145                 150                 155                 160

Lys Thr Arg Gln Gly Val Asp Asp Ala Phe Tyr Thr Leu Val Arg Glu
                165                 170                 175

Ile Arg Lys His Lys Glu Lys
            180
```